United States Patent
Harrison et al.

(10) Patent No.: US 8,048,985 B2
(45) Date of Patent: Nov. 1, 2011

(54) DIPHTHERIA TOXIN VARIANT

(75) Inventors: Robert J. Harrison, Medfield, MA (US); Johanna C. Vanderspek, Worcester, MA (US)

(73) Assignee: Anjin Group, Inc., Cockeysville, MD (US)

(*) Notice: Subject to any disclaimer, the term of this patent is extended or adjusted under 35 U.S.C. 154(b) by 0 days.

(21) Appl. No.: 12/368,254

(22) Filed: Feb. 9, 2009

(65) Prior Publication Data

US 2009/0156502 A1  Jun. 18, 2009

Related U.S. Application Data

(63) Continuation of application No. 10/995,338, filed on Nov. 24, 2004, now Pat. No. 7,585,942.

(60) Provisional application No. 60/524,615, filed on Nov. 25, 2003, now abandoned.

(51) Int. Cl.
  *A61K 38/02*  (2006.01)
  *A61K 39/02*  (2006.01)
  *A61K 39/05*  (2006.01)

(52) U.S. Cl. .................. 530/350; 424/832; 424/236.1; 424/238.1

(58) Field of Classification Search .................. None
See application file for complete search history.

(56) References Cited

U.S. PATENT DOCUMENTS

| | | | |
|---|---|---|---|
| 4,675,382 A | 6/1987 | Murphy | |
| 4,830,962 A | 5/1989 | Gelfand et al. | |
| 5,080,898 A | 1/1992 | Murphy | |
| 5,208,021 A | 5/1993 | Johnson et al. | |
| 5,352,447 A | 10/1994 | Johnson et al. | |
| 5,510,105 A | 4/1996 | Strom | |
| 5,607,675 A | 3/1997 | Strom | |
| 5,614,191 A | 3/1997 | Puri et al. | |
| 5,616,482 A | 4/1997 | Williams | |
| 5,677,148 A | 10/1997 | Williams | |
| 5,681,810 A | 10/1997 | Villemez et al. | |
| 5,703,039 A | 12/1997 | Williams et al. | |
| 5,763,250 A | 6/1998 | Williams et al. | |
| 5,827,934 A | 10/1998 | Villemez et al. | |
| 5,830,478 A | 11/1998 | Raso et al. | |
| 5,843,462 A | 12/1998 | Conti-Fine | |
| 5,843,711 A | 12/1998 | Collier et al. | |
| 5,863,891 A | 1/1999 | Williams et al. | |
| 5,932,471 A | 8/1999 | Williams et al. | |
| 6,022,950 A | 2/2000 | Murphy | |
| 6,099,842 A | 8/2000 | Pastan et al. | |
| 6,566,500 B1 | 5/2003 | Vitetta et al. | |
| 2003/0017979 A1 | 1/2003 | Mack et al. | |
| 2003/0124147 A1 | 7/2003 | Vallera et al. | |
| 2003/0143193 A1 | 7/2003 | Vitetta | |
| 2003/0176331 A1 | 9/2003 | Rosenblum | |
| 2004/0009148 A1 | 1/2004 | Vitetta et al. | |

FOREIGN PATENT DOCUMENTS

| | | |
|---|---|---|
| WO | WO 00/58456 A2 | 10/2000 |
| WO | WO 00/58456 A3 | 10/2000 |

OTHER PUBLICATIONS

Wells et al. Biochemistry 29(37): 8509-8517, 1990.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Baluna et al., "Evidence for a structural motif in toxins and interleukin-2 that may be responsible for binding to endothelial cells and initiating vascular leak syndrome", *Proc. Natl. Acad. Sci. USA.*, 96(7):3957-3962 (1999).
Database Registry, RN 301412-09-9. Sequence No. 20224 from EP 1033405.
Foss et al., "Biological correlates of acute hypersensitivity events with DAB(398)IL-2 (denileukin diftitox, ONTAK) in cutaneous T-cell lymphoma: decreased frequency and severity with steroid premedication", *Clinical Lymphoma*, 1(4):298-302 (2001). Abstract.
Kaczorek et al., "Nucleotide Sequence and Expression of the Diphtheria *tox*228 Gene in *Escherichia coli*", *Science*, vol. 221(4613), pp. 855-868, (1983).
Sequence Alignment from UniProt Database, Accession No. P005689, Jul. 21, 1986.

* cited by examiner

*Primary Examiner* — Michael Borin
(74) *Attorney, Agent, or Firm* — DLA Piper LLP (US)

(57) ABSTRACT

The present invention relates to methods and compositions of modified variants of diphtheria toxin (DT) that reduce binding to vascular endothelium or vascular endothelial cells, and therefore, reduce the incidence of Vascular Leak Syndrome. One aspect of the present invention relates to a polypeptide toxophore from a modified DT, wherein the mutation is the substitution or deletion at least one amino acid residue at the amino acid residues 6-8, 28-30 or 289-291 of native DT. Another aspect of the present invention relates to a fusion protein which comprises a modified DT and a non-DT fragment. Another aspect of the present invention relates to the use of modified DT for the treatment of cancer.

15 Claims, 14 Drawing Sheets

| catalytic domain | transmembrane domain | flexible |
| of DT | of DT | linker |

△ △ / △ / ___ Cys

FIG. 1

| 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|----|----|----|----|----|----|----|----|----|
| met | gly | ala | asp | asp | val | val | asp | ser | ser | lys | ser | phe | val | met | glu | asn | phe |
| atg | ggc | gct | gat | gat | gtt | gtt | gat | tct | tct | aaa | tct | ttt | gtg | atg | gaa | aac | ttt |
|  |  |  |  |  |  | V7A | D8S |  |  |  |  |  |  |  |  |  |  |
|  |  |  |  |  |  | ala | ser |  |  |  |  |  |  |  |  |  |  |
|  |  |  |  |  |  | gct | tct |  |  |  |  |  |  |  |  |  |  |
|  |  |  |  |  |  | V7S | D8E |  |  |  |  |  |  |  |  |  |  |
|  |  |  |  |  |  | Ser | glu |  |  |  |  |  |  |  |  |  |  |
|  |  |  |  |  |  | tct | gaa |  |  |  |  |  |  |  |  |  |  |
|  |  |  |  |  |  |  | Δ8 |  |  |  |  |  |  |  |  |  |  |

| 19 | 20 | 21 | 22 | 23 | 24 | 25 | 26 | 27 | 28 | 29 | 30 | 31 | 32 | 33 | 34 | 35 | 36 |
|----|----|----|----|----|----|----|----|----|----|----|----|----|----|----|----|----|----|
| ser | ser | tyr | his | gly | thr | lys | pro | gly | tyr | val | asp | ser | ile | gln | lys | gly | ile |
| tct | tcg | tac | cac | ggg | act | aaa | cct | ggt | tat | gta | gat | tcc | att | caa | aaa | ggt | ata |
|  |  |  |  |  |  |  |  |  |  | V29A |  |  |  |  |  |  |  |
|  |  |  |  |  |  |  |  |  |  | ala |  |  |  |  |  |  |  |
|  |  |  |  |  |  |  |  |  |  | gca |  |  |  |  |  |  |  |

| 283 | 284 | 285 | 286 | 287 | 288 | 289 | 290 | 291 | 292 | 293 | 294 | 295 | 296 | 297 | 298 | 299 | 300 |
|-----|-----|-----|-----|-----|-----|-----|-----|-----|-----|-----|-----|-----|-----|-----|-----|-----|-----|
| ala | val | asn | val | ala | gln | val | ile | asp | ser | glu | thr | ala | asp | asn | leu | glu | lys |
| gca | gta | aac | gtt | gct | cag | gtt | atc | gat | agc | gaa | act | gct | gat | aac | ctg | gaa | aaa |
|  |  |  |  |  |  |  |  | D291E |  |  |  |  |  |  |  |  |  |
|  |  |  |  |  |  |  |  | glu |  |  |  |  |  |  |  |  |  |
|  |  |  |  |  |  |  |  | gaa |  |  |  |  |  |  |  |  |  |
|  |  |  |  |  |  |  |  | D291S |  |  |  |  |  |  |  |  |  |
|  |  |  |  |  |  |  |  | ser |  |  |  |  |  |  |  |  |  |
|  |  |  |  |  |  |  |  | tct |  |  |  |  |  |  |  |  |  |

FIG. 3

Lane 1: DAB(8S,29A) 387 linker EGF
Lane 2: DAB389 EGF
Lane 3: DAB387 linker EGF
Lane 4: DAB(8E,29A) 387 linker EGF
Lane 5: DAB(8E,29A,291E) 387 linker EGF
Lane 6: DAB(7A,29A) 387 linker EGF
Lane 7: DAB(29A) 387 linker EGF 1  2  3  4  5  6  7  8  9  10

SEQUENCE LISTING

<160> NUMBER OF SEQ ID NOS: 120

<210> SEQ ID NO 1
<211> LENGTH: 536
<212> TYPE: PRT
<213> ORGANISM: Corynephage omega

<400> SEQUENCE: 1

Ala Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

```
Phe Gln Val Val His Asn Ser Tyr Asn Arg Pro Ala Tyr Ser Pro Gly
    370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
        435                 440                 445

Thr His Ile Ser Val Asn Gly Arg Lys Ile Arg Met Arg Cys Arg Ala
    450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Lys Leu
        515                 520                 525

Ser Leu Phe Phe Glu Ile Lys Ser
    530                 535

<210> SEQ ID NO 2
<211> LENGTH: 387
<212> TYPE: PRT
<213> ORGANISM: Artificial Sequence
<220> FEATURE:
<223> OTHER INFORMATION: Corynephage omega: Trucked Native DT sequence

<400> SEQUENCE: 2

Ala Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190
```

-continued

```
Arg Arg Ser Val Gly Ser Ser Leu Ser Cys Ile Asn Leu Asp Trp Asp
    195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr
385

<210> SEQ ID NO 3
<211> LENGTH: 1140
<212> TYPE: DNA
<213> ORGANISM: Artificial sequence
<220> FEATURE:
<223> OTHER INFORMATION: Corynephage omega: DT380
<220> FEATURE:
<221> NAME/KEY: CDS
<222> LOCATION: (1)..(1140)

<400> SEQUENCE: 3 atg ggc gct gat gat gtt gtt gat tct tct aaa tct ttt gtg atg gaa    48
Met Gly Ala Asp Asp Val Val Asp Ser Ser Lys Ser Phe Val Met Glu
1               5                   10                  15 aac ttt tct tcg tac cac ggg act aaa cct ggt tat gta gat tcc att    96
Asn Phe Ser Ser Tyr His Gly Thr Lys Pro Gly Tyr Val Asp Ser Ile
                20                  25                  30 caa aaa ggt ata caa aag cca aaa tct ggt aca caa gga aat tat gac    144
Gln Lys Gly Ile Gln Lys Pro Lys Ser Gly Thr Gln Gly Asn Tyr Asp
            35                  40                  45 gat gat tgg aaa ggg ttt tat agt acc gac aat aaa tac gac gct gcg    192
Asp Asp Trp Lys Gly Phe Tyr Ser Thr Asp Asn Lys Tyr Asp Ala Ala
        50                  55                  60 gga tac tct gta gat aat gaa aac ccg ctc tct gga aaa gct gga ggc    240
Gly Tyr Ser Val Asp Asn Glu Asn Pro Leu Ser Gly Lys Ala Gly Gly
65                  70                  75                  80 gtg gtc aaa gtg acg tat cca gga ctg acg aag gtt ctc gca cta aaa    288
Val Val Lys Val Thr Tyr Pro Gly Leu Thr Lys Val Leu Ala Leu Lys
                85                  90                  95 gtg gat aat gcc gaa act att aag aaa gag tta ggt tta agt ctc act    336
Val Asp Asn Ala Glu Thr Ile Lys Lys Glu Leu Gly Leu Ser Leu Thr
                100                 105                 110
```

```
gaa ccg ttg atg gag caa gtc gga acg gaa gag ttt atc aaa agg ttc      384
Glu Pro Leu Met Glu Gln Val Gly Thr Glu Glu Phe Ile Lys Arg Phe
        115                 120                 125 ggt gat ggt gct tcg cgt gta gtg ctc agc ctt ccc ttc gct gag ggg      432
Gly Asp Gly Ala Ser Arg Val Val Leu Ser Leu Pro Phe Ala Glu Gly
130                 135                 140 agt tct agc gtt gaa tat att aat aac tgg gaa cag gcg aaa gcg tta      480
Ser Ser Ser Val Glu Tyr Ile Asn Asn Trp Glu Gln Ala Lys Ala Leu
145                 150                 155                 160 agc gta gaa ctt gag att aat ttt gaa acc cgt gga aaa cgt ggc caa      528
Ser Val Glu Leu Glu Ile Asn Phe Glu Thr Arg Gly Lys Arg Gly Gln
                165                 170                 175 gat gcg atg tat gag tat atg gct caa gcc tgt gca gga aat cgt gtc      576
Asp Ala Met Tyr Glu Tyr Met Ala Gln Ala Cys Ala Gly Asn Arg Val
            180                 185                 190 agg cga tca gta ggt agc tca ttg tca tgc atc aac ctg gat tgg gat      624
Arg Arg Ser Val Gly Ser Ser Leu Ser Cys Ile Asn Leu Asp Trp Asp
        195                 200                 205 gtt atc cgt gat aaa act aaa act aag atc gaa tct ctg aaa gaa cac      672
Val Ile Arg Asp Lys Thr Lys Thr Lys Ile Glu Ser Leu Lys Glu His
210                 215                 220 ggt ccg atc aaa aac aaa atg agc gaa agc ccg aac aaa act gta tct      720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg      768
Glu Glu Lys Ala Lys Gln Tyr Leu Glu Glu Phe His Gln Thr Ala Leu
                245                 250                 255 gaa cac ccg gaa ctg tct gaa ctt aag acc gtt act ggt acc aac ccg      816
Glu His Pro Glu Leu Ser Glu Leu Lys Thr Val Thr Gly Thr Asn Pro
            260                 265                 270 gta ttc gct ggt gct aac tac gct gct tgg gca gta aac gtt gct cag      864
Val Phe Ala Gly Ala Asn Tyr Ala Ala Trp Ala Val Asn Val Ala Gln
        275                 280                 285 gtt atc gat agc gaa act gct gat aac ctg gaa aaa act acc gcg gct      912
Val Ile Asp Ser Glu Thr Ala Asp Asn Leu Glu Lys Thr Thr Ala Ala
290                 295                 300 ctg tct atc ctg ccg ggt atc ggt agc gta atg ggc atc gca gac ggc      960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg     1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt     1056
Ser Ser Leu Met Val Ala Gln Ala Ile Pro Leu Val Gly Glu Leu Val
            340                 345                 350 gat atc ggt ttc gct gca tac aac ttc gtt gaa agc atc atc aac ctg     1104
Asp Ile Gly Phe Ala Ala Tyr Asn Phe Val Glu Ser Ile Ile Asn Leu
        355                 360                 365 ttc cag gtt gtt cac aac tct tac aac cgc ccg gct                     1140
Phe Gln Val Val His Asn Ser Tyr Asn Arg Pro Ala
        370                 375                 380

<210> SEQ ID NO 4
<211> LENGTH: 380
<212> TYPE: PRT
<213> ORGANISM: Artificial sequence
<220> FEATURE:
<223> OTHER INFORMATION: Corynephage omega: DT380

<400> SEQUENCE: 4

Met Gly Ala Asp Asp Val Val Asp Ser Ser Lys Ser Phe Val Met Glu
1               5                   10                  15
```

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Trp Lys Gly Phe Tyr Ser Thr Asp Asn Lys Tyr Asp Ala Ala
50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
            115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala
370                 375                 380

<210> SEQ ID NO 5
<211> LENGTH: 1167
<212> TYPE: DNA
<213> ORGANISM: Artificial sequence
<220> FEATURE:
<223> OTHER INFORMATION: Corynephage omega: DT387/DAB389
<220> FEATURE:
<221> NAME/KEY: CDS
<222> LOCATION: (1)..(1167)

<400> SEQUENCE: 5

```
atg ggc gct gat gat gtt gtt gat tct tct aaa tct ttt gtg atg gaa      48
Met Gly Ala Asp Asp Val Val Asp Ser Ser Lys Ser Phe Val Met Glu
1               5                   10                  15 aac ttt tct tcg tac cac ggg act aaa cct ggt tat gta gat tcc att      96
Asn Phe Ser Ser Tyr His Gly Thr Lys Pro Gly Tyr Val Asp Ser Ile
            20                  25                  30 caa aaa ggt ata caa aag cca aaa tct ggt aca caa gga aat tat gac     144
Gln Lys Gly Ile Gln Lys Pro Lys Ser Gly Thr Gln Gly Asn Tyr Asp
        35                  40                  45 gat gat tgg aaa ggg ttt tat agt acc gac aat aaa tac gac gct gcg     192
Asp Asp Trp Lys Gly Phe Tyr Ser Thr Asp Asn Lys Tyr Asp Ala Ala
    50                  55                  60 gga tac tct gta gat aat gaa aac ccg ctc tct gga aaa gct gga ggc     240
Gly Tyr Ser Val Asp Asn Glu Asn Pro Leu Ser Gly Lys Ala Gly Gly
65                  70                  75                  80 gtg gtc aaa gtg acg tat cca gga ctg acg aag gtt ctc gca cta aaa     288
Val Val Lys Val Thr Tyr Pro Gly Leu Thr Lys Val Leu Ala Leu Lys
                85                  90                  95 gtg gat aat gcc gaa act att aag aaa gag tta ggt tta agt ctc act     336
Val Asp Asn Ala Glu Thr Ile Lys Lys Glu Leu Gly Leu Ser Leu Thr
            100                 105                 110 gaa ccg ttg atg gag caa gtc gga acg gaa gag ttt atc aaa agg ttc     384
Glu Pro Leu Met Glu Gln Val Gly Thr Glu Glu Phe Ile Lys Arg Phe
        115                 120                 125 ggt gat ggt gct tcg cgt gta gtg ctc agc ctt ccc ttc gct gag ggg     432
Gly Asp Gly Ala Ser Arg Val Val Leu Ser Leu Pro Phe Ala Glu Gly
    130                 135                 140 agt tct agc gtt gaa tat att aat aac tgg gaa cag gcg aaa gcg tta     480
Ser Ser Ser Val Glu Tyr Ile Asn Asn Trp Glu Gln Ala Lys Ala Leu
145                 150                 155                 160 agc gta gaa ctt gag att aat ttt gaa acc cgt gga aaa cgt ggc caa     528
Ser Val Glu Leu Glu Ile Asn Phe Glu Thr Arg Gly Lys Arg Gly Gln
                165                 170                 175 gat gcg atg tat gag tat atg gct caa gcc tgt gca gga aat cgt gtc     576
Asp Ala Met Tyr Glu Tyr Met Ala Gln Ala Cys Ala Gly Asn Arg Val
            180                 185                 190 agg cga tca gta ggt agc tca ttg tca tgc atc aac ctg gat tgg gat     624
Arg Arg Ser Val Gly Ser Ser Leu Ser Cys Ile Asn Leu Asp Trp Asp
        195                 200                 205 gtt atc cgt gat aaa act aaa act aag atc gaa tct ctg aaa gaa cac     672
Val Ile Arg Asp Lys Thr Lys Thr Lys Ile Glu Ser Leu Lys Glu His
    210                 215                 220 ggt ccg atc aaa aac aaa atg agc gaa agc ccg aac aaa act gta tct     720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg     768
Glu Glu Lys Ala Lys Gln Tyr Leu Glu Glu Phe His Gln Thr Ala Leu
                245                 250                 255 gaa cac ccg gaa ctg tct gaa ctt aag acc gtt act ggt acc aac ccg     816
Glu His Pro Glu Leu Ser Glu Leu Lys Thr Val Thr Gly Thr Asn Pro
            260                 265                 270 gta ttc gct ggt gct aac tac gct gct tgg gca gta aac gtt gct cag     864
Val Phe Ala Gly Ala Asn Tyr Ala Ala Trp Ala Val Asn Val Ala Gln
        275                 280                 285 gtt atc gat agc gaa act gct gat aac ctg gaa aaa act acc gcg gct     912
Val Ile Asp Ser Glu Thr Ala Asp Asn Leu Glu Lys Thr Thr Ala Ala
    290                 295                 300 ctg tct atc ctg ccg ggt atc ggt agc gta atg ggc atc gca gac ggc     960
```

```
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg    1008
Ala Val His His Asn Thr Glu Glu Ile Val Ala Gln Ser Ile Ala Leu
                    325                 330                 335 agc tct ctg atg gtt gct cag gcc atc ccg ctg gta ggt gaa ctg gtt    1056
Ser Ser Leu Met Val Ala Gln Ala Ile Pro Leu Val Gly Glu Leu Val
                340                 345                 350 gat atc ggt ttc gct gca tac aac ttc gtt gaa agc atc atc aac ctg    1104
Asp Ile Gly Phe Ala Ala Tyr Asn Phe Val Glu Ser Ile Ile Asn Leu
            355                 360                 365 ttc cag gtt gtt cac aac tct tac aac cgc ccg gct tac tct ccg ggt    1152
Phe Gln Val Val His Asn Ser Tyr Asn Arg Pro Ala Tyr Ser Pro Gly
        370                 375                 380 cac aag acg cat gca                                                1167
His Lys Thr His Ala
385

<210> SEQ ID NO 6
<211> LENGTH: 389
<212> TYPE: PRT
<213> ORGANISM: Artificial sequence
<220> FEATURE:
<223> OTHER INFORMATION: Corynephage omega: DT387/DAB389

<400> SEQUENCE: 6

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255
```

-continued

```
Glu His Pro Glu Leu Ser Glu Leu Lys Thr Val Thr Gly Thr Asn Pro
        260                 265                 270

Val Phe Ala Gly Ala Asn Tyr Ala Ala Trp Ala Val Asn Val Ala Gln
    275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
            325                 330                 335

Ser Ser Leu Met Val Ala Gln Ala Ile Pro Leu Val Gly Glu Leu Val
        340                 345                 350

Asp Ile Gly Phe Ala Ala Tyr Asn Phe Val Glu Ser Ile Ile Asn Leu
    355                 360                 365

Phe Gln Val Val His Asn Ser Tyr Asn Arg Pro Ala Tyr Ser Pro Gly
370                 375                 380

His Lys Thr His Ala
385
```

<210> SEQ ID NO 7
<211> LENGTH: 1365
<212> TYPE: DNA
<213> ORGANISM: Artificial sequence
<220> FEATURE:
<223> OTHER INFORMATION: Corynephage omega: DT387/DAB389 Linker
<220> FEATURE:
<221> NAME/KEY: CDS
<222> LOCATION: (1)..(1215)

<400> SEQUENCE: 7

```
atg ggc gct gat gat gtt gtt gat tct tct aaa tct ttt gtg atg gaa        48
Met Gly Ala Asp Asp Val Val Asp Ser Ser Lys Ser Phe Val Met Glu
1               5                   10                  15 aac ttt tct tcg tac cac ggg act aaa cct ggt tat gta gat tcc att        96
Asn Phe Ser Ser Tyr His Gly Thr Lys Pro Gly Tyr Val Asp Ser Ile
                20                  25                  30 caa aaa ggt ata caa aag cca aaa tct ggt aca caa gga aat tat gac       144
Gln Lys Gly Ile Gln Lys Pro Lys Ser Gly Thr Gln Gly Asn Tyr Asp
            35                  40                  45 gat gat tgg aaa ggg ttt tat agt acc gac aat aaa tac gac gct gcg       192
Asp Asp Trp Lys Gly Phe Tyr Ser Thr Asp Asn Lys Tyr Asp Ala Ala
        50                  55                  60 gga tac tct gta gat aat gaa aac ccg ctc tct gga aaa gct gga ggc       240
Gly Tyr Ser Val Asp Asn Glu Asn Pro Leu Ser Gly Lys Ala Gly Gly
65                  70                  75                  80 gtg gtc aaa gtg acg tat cca gga ctg acg aag gtt ctc gca cta aaa       288
Val Val Lys Val Thr Tyr Pro Gly Leu Thr Lys Val Leu Ala Leu Lys
                85                  90                  95 gtg gat aat gcc gaa act att aag aaa gag tta ggt tta agt ctc act       336
Val Asp Asn Ala Glu Thr Ile Lys Lys Glu Leu Gly Leu Ser Leu Thr
                100                 105                 110 gaa ccg ttg atg gag caa gtc gga acg gaa gag ttt atc aaa agg ttc       384
Glu Pro Leu Met Glu Gln Val Gly Thr Glu Glu Phe Ile Lys Arg Phe
            115                 120                 125 ggt gat ggt gct tcg cgt gta gtg ctc agc ctt ccc ttc gct gag ggg       432
Gly Asp Gly Ala Ser Arg Val Val Leu Ser Leu Pro Phe Ala Glu Gly
        130                 135                 140 agt tct agc gtt gaa tat att aat aac tgg gaa cag gcg aaa gcg tta       480
Ser Ser Ser Val Glu Tyr Ile Asn Asn Trp Glu Gln Ala Lys Ala Leu
145                 150                 155                 160
```

```
agc gta gaa ctt gag att aat ttt gaa acc cgt gga aaa cgt ggc caa       528
Ser Val Glu Leu Glu Ile Asn Phe Glu Thr Arg Gly Lys Arg Gly Gln
            165                 170                 175 gat gcg atg tat gag tat atg gct caa gcc tgt gca gga aat cgt gtc       576
Asp Ala Met Tyr Glu Tyr Met Ala Gln Ala Cys Ala Gly Asn Arg Val
        180                 185                 190 agg cga tca gta ggt agc tca ttg tca tgc atc aac ctg gat tgg gat       624
Arg Arg Ser Val Gly Ser Ser Leu Ser Cys Ile Asn Leu Asp Trp Asp
    195                 200                 205 gtt atc cgt gat aaa act aaa act aag atc gaa tct ctg aaa gaa cac       672
Val Ile Arg Asp Lys Thr Lys Thr Lys Ile Glu Ser Leu Lys Glu His
210                 215                 220 ggt ccg atc aaa aac aaa atg agc gaa agc ccg aac aaa act gta tct       720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg       768
Glu Glu Lys Ala Lys Gln Tyr Leu Glu Glu Phe His Gln Thr Ala Leu
                245                 250                 255 gaa cac ccg gaa ctg tct gaa ctt aag acc gtt act ggt acc aac ccg       816
Glu His Pro Glu Leu Ser Glu Leu Lys Thr Val Thr Gly Thr Asn Pro
            260                 265                 270 gta ttc gct ggt gct aac tac gct gct tgg gca gta aac gtt gct cag       864
Val Phe Ala Gly Ala Asn Tyr Ala Ala Trp Ala Val Asn Val Ala Gln
        275                 280                 285 gtt atc gat agc gaa act gct gat aac ctg gaa aaa act acc gcg gct       912
Val Ile Asp Ser Glu Thr Ala Asp Asn Leu Glu Lys Thr Thr Ala Ala
    290                 295                 300 ctg tct atc ctg ccg ggt atc ggt agc gta atg ggc atc gca gac ggc       960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg      1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt      1056
Ser Ser Leu Met Val Ala Gln Ala Ile Pro Leu Val Gly Glu Leu Val
            340                 345                 350 gat atc ggt ttc gct gca tac aac ttc gtt gaa agc atc atc aac ctg      1104
Asp Ile Gly Phe Ala Ala Tyr Asn Phe Val Glu Ser Ile Ile Asn Leu
        355                 360                 365 ttc cag gtt gtt cac aac tct tac aac cgc ccg gct tac tct ccg ggt      1152
Phe Gln Val Val His Asn Ser Tyr Asn Arg Pro Ala Tyr Ser Pro Gly
    370                 375                 380 cac aag acg cat gca tct agc gga ggt ggc tct agc ggt gga gga tcc      1200
His Lys Thr His Ala Ser Ser Gly Gly Gly Ser Ser Gly Gly Gly Ser
385                 390                 395                 400 gca cct act tct agc tctaccaaga aacccagct gcagtcgag cacctgctgc        1255
Ala Pro Thr Ser Ser
                405 tggatttcca gatgatcctg aacggtatca acaattacaa gaacccgaaa ctgacgcgta    1315 tgctgacctt caagttctac atgccgaaga aggccaccga actgaaacac               1365

<210> SEQ ID NO 8
<211> LENGTH: 405
<212> TYPE: PRT
<213> ORGANISM: Artificial sequence
<220> FEATURE:
<223> OTHER INFORMATION: Corynephage omega: DT387/DAB389 Linker

<400> SEQUENCE: 8

Met Gly Ala Asp Asp Val Val Asp Ser Ser Lys Ser Phe Val Met Glu
```

-continued

```
              1               5              10              15
            Asn Phe Ser Ser Tyr His Gly Thr Lys Pro Gly Tyr Val Asp Ser Ile
                             20                  25                  30

Gln Lys Gly Ile Gln Lys Pro Lys Ser Gly Thr Gln Gly Asn Tyr Asp
                             35                  40                  45

Asp Trp Lys Gly Phe Tyr Ser Thr Asp Asn Lys Tyr Asp Ala Ala
             50                  55                  60

Gly Tyr Ser Val Asp Asn Glu Asn Pro Leu Ser Gly Lys Ala Gly Gly
             65                  70                  75                  80

Val Val Lys Val Thr Tyr Pro Gly Leu Thr Lys Val Leu Ala Leu Lys
                             85                  90                  95

Val Asp Asn Ala Glu Thr Ile Lys Lys Glu Leu Gly Leu Ser Leu Thr
                            100                 105                 110

Glu Pro Leu Met Glu Gln Val Gly Thr Glu Glu Phe Ile Lys Arg Phe
                            115                 120                 125

Gly Asp Gly Ala Ser Arg Val Val Leu Ser Leu Pro Phe Ala Glu Gly
                            130                 135                 140

Ser Ser Ser Val Glu Tyr Ile Asn Asn Trp Glu Gln Ala Lys Ala Leu
            145                 150                 155                 160

Ser Val Glu Leu Glu Ile Asn Phe Glu Thr Arg Gly Lys Arg Gly Gln
                            165                 170                 175

Asp Ala Met Tyr Glu Tyr Met Ala Gln Ala Cys Ala Gly Asn Arg Val
                            180                 185                 190

Arg Arg Ser Val Gly Ser Ser Leu Ser Cys Ile Asn Leu Asp Trp Asp
                            195                 200                 205

Val Ile Arg Asp Lys Thr Lys Thr Lys Ile Glu Ser Leu Lys Glu His
                            210                 215                 220

Gly Pro Ile Lys Asn Lys Met Ser Glu Ser Pro Asn Lys Thr Val Ser
            225                 230                 235                 240

Glu Glu Lys Ala Lys Gln Tyr Leu Glu Glu Phe His Gln Thr Ala Leu
                            245                 250                 255

Glu His Pro Glu Leu Ser Glu Leu Lys Thr Val Thr Gly Thr Asn Pro
                            260                 265                 270

Val Phe Ala Gly Ala Asn Tyr Ala Ala Trp Ala Val Asn Val Ala Gln
                            275                 280                 285

Val Ile Asp Ser Glu Thr Ala Asp Asn Leu Glu Lys Thr Thr Ala Ala
                            290                 295                 300

Leu Ser Ile Leu Pro Gly Ile Gly Ser Val Met Gly Ile Ala Asp Gly
            305                 310                 315                 320

Ala Val His His Asn Thr Glu Glu Ile Val Ala Gln Ser Ile Ala Leu
                            325                 330                 335

Ser Ser Leu Met Val Ala Gln Ala Ile Pro Leu Val Gly Glu Leu Val
                            340                 345                 350

Asp Ile Gly Phe Ala Ala Tyr Asn Phe Val Glu Ser Ile Ile Asn Leu
                            355                 360                 365

Phe Gln Val Val His Asn Ser Tyr Asn Arg Pro Ala Tyr Ser Pro Gly
                            370                 375                 380

His Lys Thr His Ala Ser Ser Gly Gly Ser Ser Gly Gly Gly Ser
            385                 390                 395                 400

Ala Pro Thr Ser Ser
                            405

<210> SEQ ID NO 9
            <211> LENGTH: 1173
```

<212> TYPE: DNA
<213> ORGANISM: Artificial sequence
<220> FEATURE:
<223> OTHER INFORMATION: Corynephage omega: DT380 linker
<220> FEATURE:
<221> NAME/KEY: CDS
<222> LOCATION: (1)..(1173)

<400> SEQUENCE: 9

| | | | | | | | | | | | | | | | | |
|---|---|---|---|---|---|---|---|---|---|---|---|---|---|---|---|---|
| atg | ggc | gct | gat | gat | gtt | gtt | gat | tct | tct | aaa | tct | ttt | gtg | atg | gaa | 48 |
| Met | Gly | Ala | Asp | Asp | Val | Val | Asp | Ser | Ser | Lys | Ser | Phe | Val | Met | Glu | |
| 1 | | | | 5 | | | | | 10 | | | | | 15 | | |
| aac | ttt | tct | tcg | tac | cac | ggg | act | aaa | cct | ggt | tat | gta | gat | tcc | att | 96 |
| Asn | Phe | Ser | Ser | Tyr | His | Gly | Thr | Lys | Pro | Gly | Tyr | Val | Asp | Ser | Ile | |
| | | | | 20 | | | | | 25 | | | | | 30 | | |
| caa | aaa | ggt | ata | caa | aag | cca | aaa | tct | ggt | aca | caa | gga | aat | tat | gac | 144 |
| Gln | Lys | Gly | Ile | Gln | Lys | Pro | Lys | Ser | Gly | Thr | Gln | Gly | Asn | Tyr | Asp | |
| | | | 35 | | | | | 40 | | | | | 45 | | | |
| gat | gat | tgg | aaa | ggg | ttt | tat | agt | acc | gac | aat | aaa | tac | gac | gct | gcg | 192 |
| Asp | Asp | Trp | Lys | Gly | Phe | Tyr | Ser | Thr | Asp | Asn | Lys | Tyr | Asp | Ala | Ala | |
| 50 | | | | | 55 | | | | | 60 | | | | | | |
| gga | tac | tct | gta | gat | aat | gaa | aac | ccg | ctc | tct | gga | aaa | gct | gga | ggc | 240 |
| Gly | Tyr | Ser | Val | Asp | Asn | Glu | Asn | Pro | Leu | Ser | Gly | Lys | Ala | Gly | Gly | |
| 65 | | | | | 70 | | | | | 75 | | | | | 80 | |
| gtg | gtc | aaa | gtg | acg | tat | cca | gga | ctg | acg | aag | gtt | ctc | gca | cta | aaa | 288 |
| Val | Val | Lys | Val | Thr | Tyr | Pro | Gly | Leu | Thr | Lys | Val | Leu | Ala | Leu | Lys | |
| | | | | 85 | | | | | 90 | | | | | 95 | | |
| gtg | gat | aat | gcc | gaa | act | att | aag | aaa | gag | tta | ggt | tta | agt | ctc | act | 336 |
| Val | Asp | Asn | Ala | Glu | Thr | Ile | Lys | Lys | Glu | Leu | Gly | Leu | Ser | Leu | Thr | |
| | | | 100 | | | | | 105 | | | | | 110 | | | |
| gaa | ccg | ttg | atg | gag | caa | gtc | gga | acg | gaa | gag | ttt | atc | aaa | agg | ttc | 384 |
| Glu | Pro | Leu | Met | Glu | Gln | Val | Gly | Thr | Glu | Glu | Phe | Ile | Lys | Arg | Phe | |
| | | | 115 | | | | | 120 | | | | | 125 | | | |
| ggt | gat | ggt | gct | tcg | cgt | gta | gtg | ctc | agc | ctt | ccc | ttc | gct | gag | ggg | 432 |
| Gly | Asp | Gly | Ala | Ser | Arg | Val | Val | Leu | Ser | Leu | Pro | Phe | Ala | Glu | Gly | |
| | | 130 | | | | | 135 | | | | | 140 | | | | |
| agt | tct | agc | gtt | gaa | tat | att | aat | aac | tgg | gaa | cag | gcg | aaa | gcg | tta | 480 |
| Ser | Ser | Ser | Val | Glu | Tyr | Ile | Asn | Asn | Trp | Glu | Gln | Ala | Lys | Ala | Leu | |
| 145 | | | | | 150 | | | | | 155 | | | | | 160 | |
| agc | gta | gaa | ctt | gag | att | aat | ttt | gaa | acc | cgt | gga | aaa | cgt | ggc | caa | 528 |
| Ser | Val | Glu | Leu | Glu | Ile | Asn | Phe | Glu | Thr | Arg | Gly | Lys | Arg | Gly | Gln | |
| | | | | 165 | | | | | 170 | | | | | 175 | | |
| gat | gcg | atg | tat | gag | tat | atg | gct | caa | gcc | tgt | gca | gga | aat | cgt | gtc | 576 |
| Asp | Ala | Met | Tyr | Glu | Tyr | Met | Ala | Gln | Ala | Cys | Ala | Gly | Asn | Arg | Val | |
| | | | 180 | | | | | 185 | | | | | 190 | | | |
| agg | cga | tca | gta | ggt | agc | tca | ttg | tca | tgc | atc | aac | ctg | gat | tgg | gat | 624 |
| Arg | Arg | Ser | Val | Gly | Ser | Ser | Leu | Ser | Cys | Ile | Asn | Leu | Asp | Trp | Asp | |
| | | | 195 | | | | | 200 | | | | | 205 | | | |
| gtt | atc | cgt | gat | aaa | act | aaa | act | aag | atc | gaa | tct | ctg | aaa | gaa | cac | 672 |
| Val | Ile | Arg | Asp | Lys | Thr | Lys | Thr | Lys | Ile | Glu | Ser | Leu | Lys | Glu | His | |
| | | 210 | | | | | 215 | | | | | 220 | | | | |
| ggt | ccg | atc | aaa | aac | aaa | atg | agc | gaa | agc | ccg | aac | aaa | act | gta | tct | 720 |
| Gly | Pro | Ile | Lys | Asn | Lys | Met | Ser | Glu | Ser | Pro | Asn | Lys | Thr | Val | Ser | |
| 225 | | | | | 230 | | | | | 235 | | | | | 240 | |
| gaa | gaa | aaa | gct | aaa | cag | tac | ctg | gaa | gaa | ttc | cac | cag | act | gca | ctg | 768 |
| Glu | Glu | Lys | Ala | Lys | Gln | Tyr | Leu | Glu | Glu | Phe | His | Gln | Thr | Ala | Leu | |
| | | | | 245 | | | | | 250 | | | | | 255 | | |
| gaa | cac | ccg | gaa | ctg | tct | gaa | ctt | aag | acc | gtt | act | ggt | acc | aac | ccg | 816 |
| Glu | His | Pro | Glu | Leu | Ser | Glu | Leu | Lys | Thr | Val | Thr | Gly | Thr | Asn | Pro | |
| | | | 260 | | | | | 265 | | | | | 270 | | | |
| gta | ttc | gct | ggt | gct | aac | tac | gct | gct | tgg | gca | gta | aac | gtt | gct | cag | 864 |
| Val | Phe | Ala | Gly | Ala | Asn | Tyr | Ala | Ala | Trp | Ala | Val | Asn | Val | Ala | Gln | |

```
                  275                 280                 285
gtt atc gat agc gaa act gct gat aac ctg gaa aaa act acc gcg gct        912
Val Ile Asp Ser Glu Thr Ala Asp Asn Leu Glu Lys Thr Thr Ala Ala
    290                 295                 300 ctg tct atc ctg ccg ggt atc ggt agc gta atg ggc atc gca gac ggc        960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg       1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt       1056
Ser Ser Leu Met Val Ala Gln Ala Ile Pro Leu Val Gly Glu Leu Val
            340                 345                 350 gat atc ggt ttc gct gca tac aac ttc gtt gaa agc atc atc aac ctg       1104
Asp Ile Gly Phe Ala Ala Tyr Asn Phe Val Glu Ser Ile Ile Asn Leu
        355                 360                 365 ttc cag gtt gtt cac aac tct tac aac cgc ccg gct tct agc gga ggt       1152
Phe Gln Val Val His Asn Ser Tyr Asn Arg Pro Ala Ser Ser Gly Gly
    370                 375                 380 ggc tct agc ggt gga gga tcc                                           1173
Gly Ser Ser Gly Gly Gly Ser
385                 390

<210> SEQ ID NO 10
<211> LENGTH: 391
<212> TYPE: PRT
<213> ORGANISM: Artificial sequence
<220> FEATURE:
<223> OTHER INFORMATION: Corynephage omega: DT380 linker

<400> SEQUENCE: 10

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
```

```
                     210                 215                 220
Gly Pro Ile Lys Asn Lys Met Ser Glu Ser Pro Asn Lys Thr Val Ser
225                 230                 235                 240

Glu Glu Lys Ala Lys Gln Tyr Leu Glu Phe His Gln Thr Ala Leu
                245                 250                 255

Glu His Pro Glu Leu Ser Glu Leu Lys Thr Val Thr Gly Thr Asn Pro
                260                 265                 270

Val Phe Ala Gly Ala Asn Tyr Ala Ala Trp Ala Val Asn Val Ala Gln
                275                 280                 285

Val Ile Asp Ser Glu Thr Ala Asp Asn Leu Glu Lys Thr Thr Ala Ala
                290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Ser Ser Gly Gly
                370                 375                 380

Gly Ser Ser Gly Gly Gly Ser
385                 390

<210> SEQ ID NO 11
<211> LENGTH: 1326
<212> TYPE: DNA
<213> ORGANISM: Artificial sequence
<220> FEATURE:
<223> OTHER INFORMATION: Corynephage omega: DT387EGF/DAB389EGF
<220> FEATURE:
<221> NAME/KEY: CDS
<222> LOCATION: (1)..(1326)

<400> SEQUENCE: 11 atg ggc gct gat gat gtt gtt gat tct tct aaa tct ttt gtg atg gaa      48
Met Gly Ala Asp Asp Val Val Asp Ser Ser Lys Ser Phe Val Met Glu
1               5                   10                  15 aac ttt tct tcg tac cac ggg act aaa cct ggt tat gta gat tcc att      96
Asn Phe Ser Ser Tyr His Gly Thr Lys Pro Gly Tyr Val Asp Ser Ile
                20                  25                  30 caa aaa ggt ata caa aag cca aaa tct ggt aca caa gga aat tat gac     144
Gln Lys Gly Ile Gln Lys Pro Lys Ser Gly Thr Gln Gly Asn Tyr Asp
            35                  40                  45 gat gat tgg aaa ggg ttt tat agt acc gac aat aaa tac gac gct gcg     192
Asp Asp Trp Lys Gly Phe Tyr Ser Thr Asp Asn Lys Tyr Asp Ala Ala
        50                  55                  60 gga tac tct gta gat aat gaa aac ccg ctc tct gga aaa gct gga ggc     240
Gly Tyr Ser Val Asp Asn Glu Asn Pro Leu Ser Gly Lys Ala Gly Gly
65                  70                  75                  80 gtg gtc aaa gtg acg tat cca gga ctg acg aag gtt ctc gca cta aaa     288
Val Val Lys Val Thr Tyr Pro Gly Leu Thr Lys Val Leu Ala Leu Lys
                85                  90                  95 gtg gat aat gcc gaa act att aag aaa gag tta ggt tta agt ctc act     336
Val Asp Asn Ala Glu Thr Ile Lys Lys Glu Leu Gly Leu Ser Leu Thr
            100                 105                 110 gaa ccg ttg atg gag caa gtc gga acg gaa gag ttt atc aaa agg ttc     384
Glu Pro Leu Met Glu Gln Val Gly Thr Glu Glu Phe Ile Lys Arg Phe
        115                 120                 125
```

```
ggt gat ggt gct tcg cgt gta gtg ctc agc ctt ccc ttc gct gag ggg      432
Gly Asp Gly Ala Ser Arg Val Val Leu Ser Leu Pro Phe Ala Glu Gly
    130             135                 140 agt tct agc gtt gaa tat att aat aac tgg gaa cag gcg aaa gcg tta      480
Ser Ser Ser Val Glu Tyr Ile Asn Asn Trp Glu Gln Ala Lys Ala Leu
145                 150                 155                 160 agc gta gaa ctt gag att aat ttt gaa acc cgt gga aaa cgt ggc caa      528
Ser Val Glu Leu Glu Ile Asn Phe Glu Thr Arg Gly Lys Arg Gly Gln
                165                 170                 175 gat gcg atg tat gag tat atg gct caa gcc tgt gca gga aat cgt gtc      576
Asp Ala Met Tyr Glu Tyr Met Ala Gln Ala Cys Ala Gly Asn Arg Val
            180                 185                 190 agg cga tca gta ggt agc tca ttg tca tgc atc aac ctg gat tgg gat      624
Arg Arg Ser Val Gly Ser Ser Leu Ser Cys Ile Asn Leu Asp Trp Asp
        195                 200                 205 gtt atc cgt gat aaa act aaa act aag atc gaa tct ctg aaa gaa cac      672
Val Ile Arg Asp Lys Thr Lys Thr Lys Ile Glu Ser Leu Lys Glu His
    210                 215                 220 ggt ccg atc aaa aac aaa atg agc gaa agc ccg aac aaa act gta tct      720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg      768
Glu Glu Lys Ala Lys Gln Tyr Leu Glu Glu Phe His Gln Thr Ala Leu
                245                 250                 255 gaa cac ccg gaa ctg tct gaa ctt aag acc gtt act ggt acc aac ccg      816
Glu His Pro Glu Leu Ser Glu Leu Lys Thr Val Thr Gly Thr Asn Pro
            260                 265                 270 gta ttc gct ggt gct aac tac gct gct tgg gca gta aac gtt gct cag      864
Val Phe Ala Gly Ala Asn Tyr Ala Ala Trp Ala Val Asn Val Ala Gln
        275                 280                 285 gtt atc gat agc gaa act gct gat aac ctg gaa aaa act acc gcg gct      912
Val Ile Asp Ser Glu Thr Ala Asp Asn Leu Glu Lys Thr Thr Ala Ala
    290                 295                 300 ctg tct atc ctg ccg ggt atc ggt agc gta atg ggc atc gca gac ggc      960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg     1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt     1056
Ser Ser Leu Met Val Ala Gln Ala Ile Pro Leu Val Gly Glu Leu Val
            340                 345                 350 gat atc ggt ttc gct gca tac aac ttc gtt gaa agc atc atc aac ctg     1104
Asp Ile Gly Phe Ala Ala Tyr Asn Phe Val Glu Ser Ile Ile Asn Leu
        355                 360                 365 ttc cag gtt gtt cac aac tct tac aac cgc ccg gct tac tct ccg ggt     1152
Phe Gln Val Val His Asn Ser Tyr Asn Arg Pro Ala Tyr Ser Pro Gly
    370                 375                 380 cac aag acg cat gca aac agc gat agc gaa tgc ccg ctg agc cat gat     1200
His Lys Thr His Ala Asn Ser Asp Ser Glu Cys Pro Leu Ser His Asp
385                 390                 395                 400 ggc tat tgc ctg cat gat ggc gtg tgc atg tat att gaa gcg ctg gat     1248
Gly Tyr Cys Leu His Asp Gly Val Cys Met Tyr Ile Glu Ala Leu Asp
                405                 410                 415 aaa tat gcg tgc aac tgc gtg gtg ggc tat att ggc gaa cgc tgc cag     1296
Lys Tyr Ala Cys Asn Cys Val Val Gly Tyr Ile Gly Glu Arg Cys Gln
            420                 425                 430 tat cgc gat ctg aaa tgg tgg gaa ctg cgc                             1326
Tyr Arg Asp Leu Lys Trp Trp Glu Leu Arg
        435                 440
```

<210> SEQ ID NO 12
<211> LENGTH: 442
<212> TYPE: PRT
<213> ORGANISM: Artificial sequence
<220> FEATURE:
<223> OTHER INFORMATION: Corynephage omega: DT387EGF/DAB389EGF

<400> SEQUENCE: 12

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val

```
                              370                375               380
His Lys Thr His Ala Asn Ser Asp Ser Glu Cys Pro Leu Ser His Asp
385                390                395                400

Gly Tyr Cys Leu His Asp Gly Val Cys Met Tyr Ile Glu Ala Leu Asp
                405                410                415

Lys Tyr Ala Cys Asn Cys Val Val Gly Tyr Ile Gly Glu Arg Cys Gln
                420                425                430

Tyr Arg Asp Leu Lys Trp Trp Glu Leu Arg
                435                440

<210> SEQ ID NO 13
<211> LENGTH: 1359
<212> TYPE: DNA
<213> ORGANISM: Artificial sequence
<220> FEATURE:
<223> OTHER INFORMATION: Corynephage omega: DT387 linker EGF/DAB389
      linker EGF
<220> FEATURE:
<221> NAME/KEY: CDS
<222> LOCATION: (1)..(1359)

<400> SEQUENCE: 13 atg ggc gct gat gat gtt gtt gat tct tct aaa tct ttt gtg atg gaa        48
Met Gly Ala Asp Asp Val Val Asp Ser Ser Lys Ser Phe Val Met Glu
1               5                   10                  15 aac ttt tct tcg tac cac ggg act aaa cct ggt tat gta gat tcc att        96
Asn Phe Ser Ser Tyr His Gly Thr Lys Pro Gly Tyr Val Asp Ser Ile
                20                  25                  30 caa aaa ggt ata caa aag cca aaa tct ggt aca caa gga aat tat gac       144
Gln Lys Gly Ile Gln Lys Pro Lys Ser Gly Thr Gln Gly Asn Tyr Asp
            35                  40                  45 gat gat tgg aaa ggg ttt tat agt acc gac aat aaa tac gac gct gcg       192
Asp Asp Trp Lys Gly Phe Tyr Ser Thr Asp Asn Lys Tyr Asp Ala Ala
        50                  55                  60 gga tac tct gta gat aat gaa aac ccg ctc tct gga aaa gct gga ggc       240
Gly Tyr Ser Val Asp Asn Glu Asn Pro Leu Ser Gly Lys Ala Gly Gly
65                  70                  75                  80 gtg gtc aaa gtg acg tat cca gga ctc acg aag gtt ctc gca cta aaa       288
Val Val Lys Val Thr Tyr Pro Gly Leu Thr Lys Val Leu Ala Leu Lys
                85                  90                  95 gtg gat aat gcc gaa act att aag aaa gag tta ggt tta agt ctc act       336
Val Asp Asn Ala Glu Thr Ile Lys Lys Glu Leu Gly Leu Ser Leu Thr
                100                 105                 110 gaa ccg ttg atg gag caa gtc gga acg gaa gag ttt atc aaa agg ttc       384
Glu Pro Leu Met Glu Gln Val Gly Thr Glu Glu Phe Ile Lys Arg Phe
            115                 120                 125 ggt gat ggt gct tcg cgt gta gtg ctc agc ctt ccc ttc gct gag ggg       432
Gly Asp Gly Ala Ser Arg Val Val Leu Ser Leu Pro Phe Ala Glu Gly
        130                 135                 140 agt tct agc gtt gaa tat att aat aac tgg gaa cag gcg aaa gcg tta       480
Ser Ser Ser Val Glu Tyr Ile Asn Asn Trp Glu Gln Ala Lys Ala Leu
145                 150                 155                 160 agc gta gaa ctt gag att aat ttt gaa acc cgt gga aaa cgt ggc caa       528
Ser Val Glu Leu Glu Ile Asn Phe Glu Thr Arg Gly Lys Arg Gly Gln
                165                 170                 175 gat gcg atg tat gag tat atg gct caa gcc tgt gca gga aat cgt gtc       576
Asp Ala Met Tyr Glu Tyr Met Ala Gln Ala Cys Ala Gly Asn Arg Val
                180                 185                 190 agg cga tca gta ggt agc tca ttg tca tgc atc aac ctg gat tgg gat       624
Arg Arg Ser Val Gly Ser Ser Leu Ser Cys Ile Asn Leu Asp Trp Asp
            195                 200                 205
```

-continued

```
gtt atc cgt gat aaa act aaa act aag atc gaa tct ctg aaa gaa cac      672
Val Ile Arg Asp Lys Thr Lys Thr Lys Ile Glu Ser Leu Lys Glu His
    210                 215                 220 ggt ccg atc aaa aac aaa atg agc gaa agc ccg aac aaa act gta tct      720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg      768
Glu Glu Lys Ala Lys Gln Tyr Leu Glu Glu Phe His Gln Thr Ala Leu
                245                 250                 255 gaa cac ccg gaa ctg tct gaa ctt aag acc gtt act ggt acc acc ccg      816
Glu His Pro Glu Leu Ser Glu Leu Lys Thr Val Thr Gly Thr Thr Pro
            260                 265                 270 gta ttc gct ggt gct aac tac gct gct tgg gca gta aac gtt gct cag      864
Val Phe Ala Gly Ala Asn Tyr Ala Ala Trp Ala Val Asn Val Ala Gln
        275                 280                 285 gtt atc gat agc gaa act gct gat aac ctg gaa aaa act acc gcg gct      912
Val Ile Asp Ser Glu Thr Ala Asp Asn Leu Glu Lys Thr Thr Ala Ala
    290                 295                 300 ctg tct atc ctg ccg ggt atc ggt agc gta atg ggc atc gca gac ggc      960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg     1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt     1056
Ser Ser Leu Met Val Ala Gln Ala Ile Pro Leu Val Gly Glu Leu Val
            340                 345                 350 gat atc ggt ttc gct gca tac aac ttc gtt gaa agc atc atc aac ctg     1104
Asp Ile Gly Phe Ala Ala Tyr Asn Phe Val Glu Ser Ile Ile Asn Leu
        355                 360                 365 ttc cag gtt gtt cac aac tct tac aac cgc ccg gct tac tct ccg ggt     1152
Phe Gln Val Val His Asn Ser Tyr Asn Arg Pro Ala Tyr Ser Pro Gly
    370                 375                 380 cac aag acg cat gca tct agc gga ggt ggc tct agc ggt gga gga tcc     1200
His Lys Thr His Ala Ser Ser Gly Gly Gly Ser Ser Gly Gly Gly Ser
385                 390                 395                 400 aac agc gat agc gaa tgc ccg ctg agc cat gat ggc tat tgc ctg cat     1248
Asn Ser Asp Ser Glu Cys Pro Leu Ser His Asp Gly Tyr Cys Leu His
                405                 410                 415 gat ggc gtg tgc atg tat att gaa gcg ctg gat aaa tat gcg tgc aac     1296
Asp Gly Val Cys Met Tyr Ile Glu Ala Leu Asp Lys Tyr Ala Cys Asn
            420                 425                 430 tgc gtg gtg ggc tat att ggc gaa cgc tgc cag tat cgc gat ctg aaa     1344
Cys Val Val Gly Tyr Ile Gly Glu Arg Cys Gln Tyr Arg Asp Leu Lys
        435                 440                 445 tgg tgg gaa ctg cgc                                                 1359
Trp Trp Glu Leu Arg
    450

<210> SEQ ID NO 14
<211> LENGTH: 453
<212> TYPE: PRT
<213> ORGANISM: Artificial sequence
<220> FEATURE:
<223> OTHER INFORMATION: Corynephage omega: DT387 linker EGF/DAB389
      linker EGF

<400> SEQUENCE: 14

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30
```

```
Gln Lys Gly Ile Gln Lys Pro Lys Ser Gly Thr Gln Gly Asn Tyr Asp
         35                  40                  45

Asp Asp Trp Lys Gly Phe Tyr Ser Thr Asp Asn Lys Tyr Asp Ala Ala
 50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
             100                 105                 110

Glu Pro Leu Met Glu Gln Val Gly Thr Glu Glu Phe Ile Lys Arg Phe
         115                 120                 125

Gly Asp Gly Ala Ser Arg Val Val Leu Ser Leu Pro Phe Ala Glu Gly
     130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                 165                 170                 175

Asp Ala Met Tyr Glu Tyr Met Ala Gln Ala Cys Ala Gly Asn Arg Val
             180                 185                 190

Arg Arg Ser Val Gly Ser Ser Leu Ser Cys Ile Asn Leu Asp Trp Asp
         195                 200                 205

Val Ile Arg Asp Lys Thr Lys Thr Lys Ile Glu Ser Leu Lys Glu His
     210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                 245                 250                 255

Glu His Pro Glu Leu Ser Glu Leu Lys Thr Val Thr Gly Thr Thr Pro
             260                 265                 270

Val Phe Ala Gly Ala Asn Tyr Ala Ala Trp Ala Val Asn Val Ala Gln
         275                 280                 285

Val Ile Asp Ser Glu Thr Ala Asp Asn Leu Glu Lys Thr Thr Ala Ala
     290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                 325                 330                 335

Ser Ser Leu Met Val Ala Gln Ala Ile Pro Leu Val Gly Glu Leu Val
             340                 345                 350

Asp Ile Gly Phe Ala Ala Tyr Asn Phe Val Glu Ser Ile Ile Asn Leu
         355                 360                 365

Phe Gln Val Val His Asn Ser Tyr Asn Arg Pro Ala Tyr Ser Pro Gly
     370                 375                 380

His Lys Thr His Ala Ser Ser Gly Gly Ser Ser Gly Gly Gly Gly Ser
385                 390                 395                 400

Asn Ser Asp Ser Glu Cys Pro Leu Ser His Asp Gly Tyr Cys Leu His
                 405                 410                 415

Asp Gly Val Cys Met Tyr Ile Glu Ala Leu Asp Lys Tyr Ala Cys Asn
             420                 425                 430

Cys Val Val Gly Tyr Ile Gly Glu Arg Cys Gln Tyr Arg Asp Leu Lys
         435                 440                 445

Trp Trp Glu Leu Arg
```

-continued

<210> SEQ ID NO 15
<211> LENGTH: 1569
<212> TYPE: DNA
<213> ORGANISM: Artificial sequence
<220> FEATURE:
<223> OTHER INFORMATION: Corynephage omega: DT387IL2/DAB389IL-2
<220> FEATURE:
<221> NAME/KEY: CDS
<222> LOCATION: (1)..(1569)

<400> SEQUENCE: 15

| | | | | | | | | | | | | | | | | |
|---|---|---|---|---|---|---|---|---|---|---|---|---|---|---|---|---|
| atg | ggc | gct | gat | gat | gtt | gtt | gat | tct | tct | aaa | tct | ttt | gtg | atg | gaa | 48 |
| Met | Gly | Ala | Asp | Asp | Val | Val | Asp | Ser | Ser | Lys | Ser | Phe | Val | Met | Glu | |
| 1 | | | | 5 | | | | | 10 | | | | | 15 | | |
| aac | ttt | tct | tcg | tac | cac | ggg | act | aaa | cct | ggt | tat | gta | gat | tcc | att | 96 |
| Asn | Phe | Ser | Ser | Tyr | His | Gly | Thr | Lys | Pro | Gly | Tyr | Val | Asp | Ser | Ile | |
| | | | 20 | | | | | 25 | | | | | 30 | | | |
| caa | aaa | ggt | ata | caa | aag | cca | aaa | tct | ggt | aca | caa | gga | aat | tat | gac | 144 |
| Gln | Lys | Gly | Ile | Gln | Lys | Pro | Lys | Ser | Gly | Thr | Gln | Gly | Asn | Tyr | Asp | |
| | | 35 | | | | | 40 | | | | | 45 | | | | |
| gat | gat | tgg | aaa | ggg | ttt | tat | agt | acc | gac | aat | aaa | tac | gac | gct | gcg | 192 |
| Asp | Asp | Trp | Lys | Gly | Phe | Tyr | Ser | Thr | Asp | Asn | Lys | Tyr | Asp | Ala | Ala | |
| 50 | | | | | 55 | | | | | 60 | | | | | | |
| gga | tac | tct | gta | gat | aat | gaa | aac | ccg | ctc | tct | gga | aaa | gct | gga | ggc | 240 |
| Gly | Tyr | Ser | Val | Asp | Asn | Glu | Asn | Pro | Leu | Ser | Gly | Lys | Ala | Gly | Gly | |
| 65 | | | | | 70 | | | | | 75 | | | | | 80 | |
| gtg | gtc | aaa | gtg | acg | tat | cca | gga | ctg | acg | aag | gtt | ctc | gca | cta | aaa | 288 |
| Val | Val | Lys | Val | Thr | Tyr | Pro | Gly | Leu | Thr | Lys | Val | Leu | Ala | Leu | Lys | |
| | | | | 85 | | | | | 90 | | | | | 95 | | |
| gtg | gat | aat | gcc | gaa | act | att | aag | aaa | gag | tta | ggt | tta | agt | ctc | act | 336 |
| Val | Asp | Asn | Ala | Glu | Thr | Ile | Lys | Lys | Glu | Leu | Gly | Leu | Ser | Leu | Thr | |
| | | | 100 | | | | | 105 | | | | | 110 | | | |
| gaa | ccg | ttg | atg | gag | caa | gtc | gga | acg | gaa | gag | ttt | atc | aaa | agg | ttc | 384 |
| Glu | Pro | Leu | Met | Glu | Gln | Val | Gly | Thr | Glu | Glu | Phe | Ile | Lys | Arg | Phe | |
| | | 115 | | | | | 120 | | | | | 125 | | | | |
| ggt | gat | ggt | gct | tcg | cgt | gta | gtg | ctc | agc | ctt | ccc | ttc | gct | gag | ggg | 432 |
| Gly | Asp | Gly | Ala | Ser | Arg | Val | Val | Leu | Ser | Leu | Pro | Phe | Ala | Glu | Gly | |
| | | 130 | | | | | 135 | | | | | 140 | | | | |
| agt | tct | agc | gtt | gaa | tat | att | aat | acc | tgg | gaa | cag | gcg | aaa | gcg | tta | 480 |
| Ser | Ser | Ser | Val | Glu | Tyr | Ile | Asn | Thr | Trp | Glu | Gln | Ala | Lys | Ala | Leu | |
| 145 | | | | | 150 | | | | | 155 | | | | | 160 | |
| agc | gta | gaa | ctt | gag | att | aat | ttt | gaa | acc | cgt | gga | aaa | cgt | ggc | caa | 528 |
| Ser | Val | Glu | Leu | Glu | Ile | Asn | Phe | Glu | Thr | Arg | Gly | Lys | Arg | Gly | Gln | |
| | | | | 165 | | | | | 170 | | | | | 175 | | |
| gat | gcg | atg | tat | gat | tat | atg | gct | caa | gcc | tgt | gca | gga | aat | cgt | gtc | 576 |
| Asp | Ala | Met | Tyr | Asp | Tyr | Met | Ala | Gln | Ala | Cys | Ala | Gly | Asn | Arg | Val | |
| | | | 180 | | | | | 185 | | | | | 190 | | | |
| agg | cga | tca | gta | ggt | agc | tca | ttg | tca | tgc | atc | aac | ctg | gat | tgg | gat | 624 |
| Arg | Arg | Ser | Val | Gly | Ser | Ser | Leu | Ser | Cys | Ile | Asn | Leu | Asp | Trp | Asp | |
| | | 195 | | | | | 200 | | | | | 205 | | | | |
| gtt | atc | cgt | gat | aaa | act | aaa | act | aag | atc | gaa | tct | ctg | aaa | gaa | cac | 672 |
| Val | Ile | Arg | Asp | Lys | Thr | Lys | Thr | Lys | Ile | Glu | Ser | Leu | Lys | Glu | His | |
| | | 210 | | | | | 215 | | | | | 220 | | | | |
| ggt | ccg | atc | aaa | aac | aaa | atg | agc | gaa | agc | ccg | aac | aaa | act | gta | tct | 720 |
| Gly | Pro | Ile | Lys | Asn | Lys | Met | Ser | Glu | Ser | Pro | Asn | Lys | Thr | Val | Ser | |
| 225 | | | | | 230 | | | | | 235 | | | | | 240 | |
| gaa | gaa | aaa | gct | aaa | cag | tac | ctg | gaa | gaa | ttc | cac | cag | act | gca | ctg | 768 |
| Glu | Glu | Lys | Ala | Lys | Gln | Tyr | Leu | Glu | Glu | Phe | His | Gln | Thr | Ala | Leu | |
| | | | | 245 | | | | | 250 | | | | | 255 | | |
| gaa | cac | ccg | gaa | ctg | tct | gaa | ctt | aag | acc | gtt | act | ggt | acc | aac | ccg | 816 |

```
                                                                                  864
gta ttc gct ggt gct aac tac gct gct tgg gca gta aac gtt gct cag
Val Phe Ala Gly Ala Asn Tyr Ala Ala Trp Ala Val Asn Val Ala Gln
        275                 280                 285

912
gtt atc gat agc gaa act gct gat aac ctg gaa aaa act acc gcg gct
Val Ile Asp Ser Glu Thr Ala Asp Asn Leu Glu Lys Thr Thr Ala Ala
        290                 295                 300

960
ctg tct atc ctg ccg ggt atc ggt agc gta atg ggc atc gca gac ggc
Leu Ser Ile Leu Pro Gly Ile Gly Ser Val Met Gly Ile Ala Asp Gly
305                 310                 315                 320

1008
gcc gtt cac cac aac act gaa gaa atc gtt gca cag tct atc gct ctg
Ala Val His His Asn Thr Glu Glu Ile Val Ala Gln Ser Ile Ala Leu
                325                 330                 335

1056
agc tct ctg atg gtt gct cag gcc atc ccg ctg gta ggt gaa ctg gtt
Ser Ser Leu Met Val Ala Gln Ala Ile Pro Leu Val Gly Glu Leu Val
            340                 345                 350

1104
gat atc ggt ttc gct gca tac aac ttc gtt gaa agc atc atc aac ctg
Asp Ile Gly Phe Ala Ala Tyr Asn Phe Val Glu Ser Ile Ile Asn Leu
        355                 360                 365

1152
ttc cag gtt gtt cac aac tct tac aac cgc ccg gct tac tct ccg ggt
Phe Gln Val Val His Asn Ser Tyr Asn Arg Pro Ala Tyr Ser Pro Gly
370                 375                 380

1200
cac aag acg cat gca gca cct act tct agc tct acc aag aaa acc cag
His Lys Thr His Ala Ala Pro Thr Ser Ser Ser Thr Lys Lys Thr Gln
385                 390                 395                 400

1248
ctg cag ctc gag cac ctg ctg ctg gat ttg cag atg atc ctg aac ggt
Leu Gln Leu Glu His Leu Leu Leu Asp Leu Gln Met Ile Leu Asn Gly
                405                 410                 415

1296
atc aac aat tac aag aac ccg aaa ctg acg cgt atg ctg acc ttc aag
Ile Asn Asn Tyr Lys Asn Pro Lys Leu Thr Arg Met Leu Thr Phe Lys
            420                 425                 430

1344
ttc tac atg ccg aag aag gcc acc gaa ctg aaa cac ctg ctg cag tgt
Phe Tyr Met Pro Lys Lys Ala Thr Glu Leu Lys His Leu Leu Gln Cys
        435                 440                 445

1392
cta gaa gaa gaa ctg aaa ccg ctg gag gaa gtt ctg aac ctg gct cag
Leu Glu Glu Glu Leu Lys Pro Leu Glu Glu Val Leu Asn Leu Ala Gln
450                 455                 460

1440
tct aaa aac ttc cac ctg cgg ccg cgt gac ctg atc tct aac atc aac
Ser Lys Asn Phe His Leu Arg Pro Arg Asp Leu Ile Ser Asn Ile Asn
465                 470                 475                 480

1488
gta atc gtt ctg gaa ctg aag ggc tct gaa acc acc ttc atg tgt gaa
Val Ile Val Leu Glu Leu Lys Gly Ser Glu Thr Thr Phe Met Cys Glu
                485                 490                 495

1536
tac gct gat gag acc gca acc atc gta gaa ttc ctg aac cgt tgg atc
Tyr Ala Asp Glu Thr Ala Thr Ile Val Glu Phe Leu Asn Arg Trp Ile
            500                 505                 510

1569
acc ttc tgt cag tct atc atc tct acc ctg acc
Thr Phe Cys Gln Ser Ile Ile Ser Thr Leu Thr
        515                 520
```

<210> SEQ ID NO 16
<211> LENGTH: 523
<212> TYPE: PRT
<213> ORGANISM: Artificial sequence
<220> FEATURE:
<223> OTHER INFORMATION: Corynephage omega: DT387IL2/DAB389IL-2

<400> SEQUENCE: 16

```
Met G

-continued

```
Asn Phe Ser Ser Tyr His Gly Thr Lys Pro Gly Tyr Val Asp Ser Ile
            20                  25                  30
Gln Lys Gly Ile Gln Lys Pro Lys Ser Gly Thr Gln Gly Asn Tyr Asp
            35                  40                  45
Asp Asp Trp Lys Gly Phe Tyr Ser Thr Asp Asn Lys Tyr Asp Ala Ala
 50                  55                  60
Gly Tyr Ser Val Asp Asn Glu Asn Pro Leu Ser Gly Lys Ala Gly Gly
 65                  70                  75                  80
Val Val Lys Val Thr Tyr Pro Gly Leu Thr Lys Val Leu Ala Leu Lys
                    85                  90                  95
Val Asp Asn Ala Glu Thr Ile Lys Glu Leu Gly Leu Ser Leu Thr
                100                 105                 110
Glu Pro Leu Met Glu Gln Val Gly Thr Glu Phe Ile Lys Arg Phe
                115                 120                 125
Gly Asp Gly Ala Ser Arg Val Val Leu Ser Leu Pro Phe Ala Glu Gly
                130                 135                 140
Ser Ser Ser Val Glu Tyr Ile Asn Thr Trp Glu Gln Ala Lys Ala Leu
145                 150                 155                 160
Ser Val Glu Leu Glu Ile Asn Phe Glu Thr Arg Gly Lys Arg Gly Gln
                165                 170                 175
Asp Ala Met Tyr Asp Tyr Met Ala Gln Ala Cys Ala Gly Asn Arg Val
                180                 185                 190
Arg Arg Ser Val Gly Ser Ser Leu Ser Cys Ile Asn Leu Asp Trp Asp
                195                 200                 205
Val Ile Arg Asp Lys Thr Lys Thr Lys Ile Glu Ser Leu Lys Glu His
                210                 215                 220
Gly Pro Ile Lys Asn Lys Met Ser Glu Ser Pro Asn Lys Thr Val Ser
225                 230                 235                 240
Glu Glu Lys Ala Lys Gln Tyr Leu Glu Glu Phe His Gln Thr Ala Leu
                245                 250                 255
Glu His Pro Glu Leu Ser Glu Leu Lys Thr Val Thr Gly Thr Asn Pro
                260                 265                 270
Val Phe Ala Gly Ala Asn Tyr Ala Ala Trp Ala Val Asn Val Ala Gln
                275                 280                 285
Val Ile Asp Ser Glu Thr Ala Asp Asn Leu Glu Lys Thr Thr Ala Ala
                290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
                340                 345                 350
Asp Ile Gly Phe Ala Ala Tyr Asn Phe Val Glu Ser Ile Ile Asn Leu
                355                 360                 365
Phe Gln Val Val His Asn Ser Tyr Asn Arg Pro Ala Tyr Ser Pro Gly
                370                 375                 380
His Lys Thr His Ala Ala Pro Thr Ser Ser Thr Lys Thr Gln
385                 390                 395                 400
Leu Gln Leu Glu His Leu Leu Leu Asp Leu Gln Met Ile Leu Asn Gly
                405                 410                 415
Ile Asn Asn Tyr Lys Asn Pro Lys Leu Thr Arg Met Leu Thr Phe Lys
                420                 425                 430
Phe Tyr Met Pro Lys Lys Ala Thr Glu Leu Lys His Leu Leu Gln Cys
                435                 440                 445
```

```
Leu Glu Glu Leu Lys Pro Leu Glu Val Leu Asn Leu Ala Gln
    450             455             460

Ser Lys Asn Phe His Leu Arg Pro Arg Asp Leu Ile Ser Asn Ile Asn
465             470             475             480

Val Ile Val Leu Glu Leu Lys Gly Ser Glu Thr Thr Phe Met Cys Glu
                485             490             495

Tyr Ala Asp Glu Thr Ala Thr Ile Val Glu Phe Leu Asn Arg Trp Ile
            500             505             510

Thr Phe Cys Gln Ser Ile Ile Ser Thr Leu Thr
            515             520

<210> SEQ ID NO 17
<211> LENGTH: 1602
<212> TYPE: DNA
<213> ORGANISM: Artificial sequence
<220> FEATURE:
<223> OTHER INFORMATION: Corynephage omega: DT387 linker IL2/DAB389
      linker IL2
<220> FEATURE:
<221> NAME/KEY: CDS
<222> LOCATION: (1)..(1602)

<400> SEQUENCE: 17 atg ggc gct gat gat gtt gtt gat tct tct aaa tct ttt gtg atg gaa      48
Met Gly Ala Asp Asp Val Val Asp Ser Ser Lys Ser Phe Val Met Glu
1

```
                195                 200                 205
gtt atc cgt gat aaa act aaa act aag atc gaa tct ctg aaa gaa cac      672
Val Ile Arg Asp Lys Thr Lys Thr Lys Ile Glu Ser Leu Lys Glu His
210                 215                 220 ggt ccg atc aaa aac aaa atg agc gaa agc ccg aac aaa act gta tct      720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg      768
Glu Glu Lys Ala Lys Gln Tyr Leu Glu Glu Phe His Gln Thr Ala Leu
                245                 250                 255 gaa cac ccg gaa ctg tct gaa ctt aag acc gtt act ggt acc aac ccg      816
Glu His Pro Glu Leu Ser Glu Leu Lys Thr Val Thr Gly Thr Asn Pro
        260                 265                 270 gta ttc gct ggt gct aac tac gct gct tgg gca gta aac gtt gct cag      864
Val Phe Ala Gly Ala Asn Tyr Ala Ala Trp Ala Val Asn Val Ala Gln
    275                 280                 285 gtt atc gat agc gaa act gct gat aac ctg gaa aaa act acc gcg gct      912
Val Ile Asp Ser Glu Thr Ala Asp Asn Leu Glu Lys Thr Thr Ala Ala
290                 295                 300 ctg tct atc ctg ccg ggt atc ggt agc gta atg ggc atc gca gac ggc      960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg     1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt     1056
Ser Ser Leu Met Val Ala Gln Ala Ile Pro Leu Val Gly Glu Leu Val
        340                 345                 350 gat atc ggt ttc gct gca tac aac ttc gtt gaa agc atc atc aac ctg     1104
Asp Ile Gly Phe Ala Ala Tyr Asn Phe Val Glu Ser Ile Ile Asn Leu
    355                 360                 365 ttc cag gtt gtt cac aac tct tac aac cgc ccg gct tac tct ccg ggt     1152
Phe Gln Val Val His Asn Ser Tyr Asn Arg Pro Ala Tyr Ser Pro Gly
370                 375                 380 cac aag acg cat gca tct agc gga ggt ggc tct agc ggt gga gga tcc     1200
His Lys Thr His Ala Ser Ser Gly Gly Gly Ser Ser Gly Gly Gly Ser
385                 390                 395                 400 gca cct act tct agc tct acc aag aaa acc cag ctg cag ctc gag cac     1248
Ala Pro Thr Ser Ser Ser Thr Lys Lys Thr Gln Leu Gln Leu Glu His
                405                 410                 415 ctg ctg ctg gat ttg cag atg atc ctg aac ggt atc aac aat tac aag     1296
Leu Leu Leu Asp Leu Gln Met Ile Leu Asn Gly Ile Asn Asn Tyr Lys
        420                 425                 430 aac ccg aaa ctg acg cgt atg ctg acc ttc aag ttc tac atg ccg aag     1344
Asn Pro Lys Leu Thr Arg Met Leu Thr Phe Lys Phe Tyr Met Pro Lys
    435                 440                 445 aag gcc acc gaa ctg aaa cac ctg ctg cag tgt cta gaa gaa gaa ctg     1392
Lys Ala Thr Glu Leu Lys His Leu Leu Gln Cys Leu Glu Glu Glu Leu
450                 455                 460 aaa ccg ctg gag gaa gtt ctg aac ctg gct cag tct aaa aac ttc cac     1440
Lys Pro Leu Glu Glu Val Leu Asn Leu Ala Gln Ser Lys Asn Phe His
465                 470                 475                 480 ctg cgg ccg cgt gac ctg atc tct aac atc aac gta atc gtt ctg gaa     1488
Leu Arg Pro Arg Asp Leu Ile Ser Asn Ile Asn Val Ile Val Leu Glu
                485                 490                 495 ctg aag ggc tct gaa acc acc ttc atg tgt gaa tac gct gat gag acc     1536
Leu Lys Gly Ser Glu Thr Thr Phe Met Cys Glu Tyr Ala Asp Glu Thr
        500                 505                 510 gca acc atc gta gaa ttc ctg aac cgt tgg atc acc ttc tgt cag tct     1584
Ala Thr Ile Val Glu Phe Leu Asn Arg Trp Ile Thr Phe Cys Gln Ser
```

```
                515              520              525
atc atc tct acc ctg acc                                              1602
Ile Ile Ser Thr Leu Thr
    530
```

<210> SEQ ID NO 18
<211> LENGTH: 534
<212> TYPE: PRT
<213> ORGANISM: Artificial sequence
<220> FEATURE:
<223> OTHER INFORMATION: Corynephage omega: DT387 linker IL2/DAB389
      linker IL2

<400> SEQUENCE: 18

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335
```

```
Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
370                 375                 380

His Lys Thr His Ala Ser Ser Gly Gly Gly Ser Ser Gly Gly Gly Ser
385                 390                 395                 400

Ala Pro Thr Ser Ser Ser Thr Lys Lys Thr Gln Leu Gln Leu Glu His
                405                 410                 415

Leu Leu Leu Asp Leu Gln Met Ile Leu Asn Gly Ile Asn Asn Tyr Lys
            420                 425                 430

Asn Pro Lys Leu Thr Arg Met Leu Thr Phe Lys Phe Tyr Met Pro Lys
            435                 440                 445

Lys Ala Thr Glu Leu Lys His Leu Leu Gln Cys Leu Glu Glu Glu Leu
450                 455                 460

Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
                485                 490                 495

Leu Lys Gly Ser Glu Thr Thr Phe Met Cys Glu Tyr Ala Asp Glu Thr
            500                 505                 510

Ala Thr Ile Val Glu Phe Leu Asn Arg Trp Ile Thr Phe Cys Gln Ser
            515                 520                 525

Ile Ile Ser Thr Leu Thr
            530

<210> SEQ ID NO 19
<211> LENGTH: 1602
<212> TYPE: DNA
<213> ORGANISM: Artificial sequence
<220> FEATURE:
<223> OTHER INFORMATION: Corynephage omega: DT387(V7A)linkerIL2
<220> FEATURE:
<221> NAME/KEY: CDS
<222> LOCATION: (1)..(1602)

<400> SEQUENCE: 19 atg ggc gct gat gat gtt gct gat tct tct aaa tct ttt gtg atg gaa     48
Met Gly Ala Asp Asp Val Ala Asp Ser Ser Lys Ser Phe Val Met Glu
1               5                   10                  15 aac ttt tct tcg tac cac ggg act aaa cct ggt tat gta gat tcc att     96
Asn Phe Ser Ser Tyr His Gly Thr Lys Pro Gly Tyr Val Asp Ser Ile
                20                  25                  30 caa aaa ggt ata caa aag cca aaa tct ggt aca caa gga aat tat gac    144
Gln Lys Gly Ile Gln Lys Pro Lys Ser Gly Thr Gln Gly Asn Tyr Asp
            35                  40                  45 gat gat tgg aaa ggg ttt tat agt acc gac aat aaa tac gac gct gcg    192
Asp Asp Trp Lys Gly Phe Tyr Ser Thr Asp Asn Lys Tyr Asp Ala Ala
        50                  55                  60 gga tac tct gta gat aat gaa aac ccg ctc tct gga aaa gct gga ggc    240
Gly Tyr Ser Val Asp Asn Glu Asn Pro Leu Ser Gly Lys Ala Gly Gly
65                  70                  75                  80 gtg gtc aaa gtg acg tat cca gga ctg acg aag gtt ctc gca cta aaa    288
Val Val Lys Val Thr Tyr Pro Gly Leu Thr Lys Val Leu Ala Leu Lys
                85                  90                  95 gtg gat aat gcc gaa act att aag aaa gag tta ggt tta agt ctc act    336
Val Asp Asn Ala Glu Thr Ile Lys Lys Glu Leu Gly Leu Ser Leu Thr
            100                 105                 110
```

| | | |
|---|---|---|
| gaa ccg ttg atg gag caa gtc gga acg gaa gag ttt atc aaa agg ttc<br>Glu Pro Leu Met Glu Gln Val Gly Thr Glu Glu Phe Ile Lys Arg Phe<br>115                       120                     125 | | 384 |
| ggt gat ggt gct tcg cgt gta gtg ctc agc ctt ccc ttc gct gag ggg<br>Gly Asp Gly Ala Ser Arg Val Val Leu Ser Leu Pro Phe Ala Glu Gly<br>    130                   135                   140 | | 432 |
| agt tct agc gtt gaa tat att aat aac tgg gaa cag gcg aaa gcg tta<br>Ser Ser Ser Val Glu Tyr Ile Asn Asn Trp Glu Gln Ala Lys Ala Leu<br>145                     150                   155                   160 | | 480 |
| agc gta gaa ctt gag att aat ttt gaa acc cgt gga aaa cgt ggc caa<br>Ser Val Glu Leu Glu Ile Asn Phe Glu Thr Arg Gly Lys Arg Gly Gln<br>                   165                   170                   175 | | 528 |
| gat gcg atg tat gag tat atg gct caa gcc tgt gca gga aat cgt gtc<br>Asp Ala Met Tyr Glu Tyr Met Ala Gln Ala Cys Ala Gly Asn Arg Val<br>    180                   185                   190 | | 576 |
| agg cga tca gta ggt agc tca ttg tca tgc atc aac ctg gat tgg gat<br>Arg Arg Ser Val Gly Ser Ser Leu Ser Cys Ile Asn Leu Asp Trp Asp<br>195                     200                   205 | | 624 |
| gtt atc cgt gat aaa act aaa act aag atc gaa tct ctg aaa gaa cac<br>Val Ile Arg Asp Lys Thr Lys Thr Lys Ile Glu Ser Leu Lys Glu His<br>    210                   215                   220 | | 672 |
| ggt ccg atc aaa aac aaa atg agc gaa agc ccg aac aaa act gta tct<br>Gly Pro Ile Lys Asn Lys Met Ser Glu Ser Pro Asn Lys Thr Val Ser<br>225                     230                   235                   240 | | 720 |
| gaa gaa aaa gct aaa cag tac ctg gaa gaa ttc cac cag act gca ctg<br>Glu Glu Lys Ala Lys Gln Tyr Leu Glu Glu Phe His Gln Thr Ala Leu<br>                   245                   250                   255 | | 768 |
| gaa cac ccg gaa ctg tct gaa ctt aag acc gtt act ggt acc aac ccg<br>Glu His Pro Glu Leu Ser Glu Leu Lys Thr Val Thr Gly Thr Asn Pro<br>    260                   265                   270 | | 816 |
| gta ttc gct ggt gct aac tac gct gct tgg gca gta aac gtt gct cag<br>Val Phe Ala Gly Ala Asn Tyr Ala Ala Trp Ala Val Asn Val Ala Gln<br>275                     280                   285 | | 864 |
| gtt atc gat agc gaa act gct gat aac ctg gaa aaa act acc gcg gct<br>Val Ile Asp Ser Glu Thr Ala Asp Asn Leu Glu Lys Thr Thr Ala Ala<br>    290                   295                   300 | | 912 |
| ctg tct atc ctg ccg ggt atc ggt agc gta atg ggc atc gca gac ggc<br>Leu Ser Ile Leu Pro Gly Ile Gly Ser Val Met Gly Ile Ala Asp Gly<br>305                     310                   315                   320 | | 960 |
| gcc gtt cac cac aac act gaa gaa atc gtt gca cag tct atc gct ctg<br>Ala Val His His Asn Thr Glu Glu Ile Val Ala Gln Ser Ile Ala Leu<br>                   325                   330                   335 | | 1008 |
| agc tct ctg atg gtt gct cag gcc atc ccg ctg gta ggt gaa ctg gtt<br>Ser Ser Leu Met Val Ala Gln Ala Ile Pro Leu Val Gly Glu Leu Val<br>    340                   345                   350 | | 1056 |
| gat atc ggt ttc gct gca tac aac ttc gtt gaa agc atc atc aac ctg<br>Asp Ile Gly Phe Ala Ala Tyr Asn Phe Val Glu Ser Ile Ile Asn Leu<br>355                     360                   365 | | 1104 |
| ttc cag gtt gtt cac aac tct tac aac cgc ccg gct tac tct ccg ggt<br>Phe Gln Val Val His Asn Ser Tyr Asn Arg Pro Ala Tyr Ser Pro Gly<br>    370                   375                   380 | | 1152 |
| cac aag acg cat gca tct agc gga ggt ggc tct agc ggt gga gga tcc<br>His Lys Thr His Ala Ser Ser Gly Gly Gly Ser Ser Gly Gly Gly Ser<br>385                     390                   395                   400 | | 1200 |
| gca cct act tct agc tct acc aag aaa acc cag ctg cag ctc gag cac<br>Ala Pro Thr Ser Ser Ser Thr Lys Lys Thr Gln Leu Gln Leu Glu His<br>                   405                   410                   415 | | 1248 |
| ctg ctg ctg gat ttg cag atg atc ctg aac ggt atc aac aat tac aag<br>Leu Leu Leu Asp Leu Gln Met Ile Leu Asn Gly Ile Asn Asn Tyr Lys<br>    420                   425                   430 | | 1296 |

```
aac ccg aaa ctg acg cgt atg ctg acc ttc aag ttc tac atg ccg aag     1344
Asn Pro Lys Leu Thr Arg Met Leu Thr Phe Lys Phe Tyr Met Pro Lys
        435                 440                 445 aag gcc acc gaa ctg aaa cac ctg ctg cag tgt cta gaa gaa gaa ctg     1392
Lys Ala Thr Glu Leu Lys His Leu Leu Gln Cys Leu Glu Glu Glu Leu
    450                 455                 460 aaa ccg ctg gag gaa gtt ctg aac ctg gct cag tct aaa aac ttc cac     1440
Lys Pro Leu Glu Glu Val Leu Asn Leu Ala Gln Ser Lys Asn Phe His
465                 470                 475                 480 ctg cgg ccg cgt gac ctg atc tct aac atc aac gta atc gtt ctg gaa     1488
Leu Arg Pro Arg Asp Leu Ile Ser Asn Ile Asn Val Ile Val Leu Glu
                485                 490                 495 ctg aag ggc tct gaa acc acc ttc atg tgt gaa tac gct gat gag acc     1536
Leu Lys Gly Ser Glu Thr Thr Phe Met Cys Glu Tyr Ala Asp Glu Thr
            500                 505                 510 gca acc atc gta gaa ttc ctg aac cgt tgg atc acc ttc tgt cag tct     1584
Ala Thr Ile Val Glu Phe Leu Asn Arg Trp Ile Thr Phe Cys Gln Ser
        515                 520                 525 atc atc tct acc ctg acc                                              1602
Ile Ile Ser Thr Leu Thr
        530

<210> SEQ ID NO 20
<211> LENGTH: 534
<212> TYPE: PRT
<213> ORGANISM: Artificial sequence
<220> FEATURE:
<223> OTHER INFORMATION: Corynephage omega: DT387(V7A)linkerIL2

<400> SEQUENCE: 20

Met Gly Ala Asp Asp Val Ala Asp Ser Ser Lys Ser Phe Val Met Glu
1               5                   10                  15

Asn Phe Ser

```
Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
            245                 250                 255

Glu His Pro Glu Leu Ser Glu Leu Lys Thr Val Thr Gly Thr Asn Pro
        260                 265                 270

Val Phe Ala Gly Ala Asn Tyr Ala Ala Trp Ala Val Asn Val Ala Gln
    275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
            325                 330                 335

Ser Ser Leu Met Val Ala Gln Ala Ile Pro Leu Val Gly Glu Leu Val
        340                 345                 350

Asp Ile Gly Phe Ala Ala Tyr Asn Phe Val Glu Ser Ile Ile Asn Leu
    355                 360                 365

Phe Gln Val Val His Asn Ser Tyr Asn Arg Pro Ala Tyr Ser Pro Gly
370                 375                 380

His Lys Thr His Ala Ser Ser Gly Gly Ser Ser Gly Gly Ser
385                 390                 395                 400

Ala Pro Thr Ser Ser Ser Thr Lys Lys Thr Gln Leu Gln Leu Glu His
            405                 410                 415

Leu Leu Leu Asp Leu Gln Met Ile Leu Asn Gly Ile Asn Asn Tyr Lys
        420                 425                 430

Asn Pro Lys Leu Thr Arg Met Leu Thr Phe Lys Phe Tyr Met Pro Lys
    435                 440                 445

Lys Ala Thr Glu Leu Lys His Leu Leu Gln Cys Leu Glu Glu Glu Leu
450                 455                 460

Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
            485                 490                 495

Leu Lys Gly Ser Glu Thr Thr Phe Met Cys Glu Tyr Ala Asp Glu Thr
        500                 505                 510

Ala Thr Ile Val Glu Phe Leu Asn Arg Trp Ile Thr Phe Cys Gln Ser
    515                 520                 525

Ile Ile Ser Thr Leu Thr
    530
```

<210> SEQ ID NO 21
<211> LENGTH: 1602
<212> TYPE: DNA
<213> ORGANISM: Artificial sequence
<220> FEATURE:
<223> OTHER INFORMATION: Corynephage omega: DT387(D8S)linkerIL2
<220> FEATURE:
<221> NAME/KEY: CDS
<222> LOCATION: (1)..(1602)

<400> SEQUENCE: 21

```
atg ggc gct gat gat gtt gtt tct tct tct aaa tct ttt gtg atg gaa    48
Met Gly Ala Asp Asp Val Val Ser Ser Ser Lys Ser Phe Val Met Glu
1               5                   10                  15 aac ttt tct tcg tac cac ggg act aaa cct ggt tat gta gat tcc att    96
Asn Phe Ser Ser Tyr His Gly Thr Lys Pro Gly Tyr Val Asp Ser Ile
            20                  25                  30
```

| | | |
|---|---|---|
| caa aaa ggt ata caa aag cca aaa tct ggt aca caa gga aat tat gac<br>Gln Lys Gly Ile Gln Lys Pro Lys Ser Gly Thr Gln Gly Asn Tyr Asp<br>             35                   40                  45 | | 144 |
| gat gat tgg aaa ggg ttt tat agt acc gac aat aaa tac gac gct gcg<br>Asp Asp Trp Lys Gly Phe Tyr Ser Thr Asp Asn Lys Tyr Asp Ala Ala<br> 50                         55                      60 | | 192 |
| gga tac tct gta gat aat gaa aac ccg ctc tct gga aaa gct gga ggc<br>Gly Tyr Ser Val Asp Asn Glu Asn Pro Leu Ser Gly Lys Ala Gly Gly<br>65                    70                    75                    80 | | 240 |
| gtg gtc aaa gtg acg tat cca gga ctg acg aag gtt ctc gca cta aaa<br>Val Val Lys Val Thr Tyr Pro Gly Leu Thr Lys Val Leu Ala Leu Lys<br>                   85                   90                  95 | | 288 |
| gtg gat aat gcc gaa act att aag aaa gag tta ggt tta agt ctc act<br>Val Asp Asn Ala Glu Thr Ile Lys Lys Glu Leu Gly Leu Ser Leu Thr<br>             100                  105               110 | | 336 |
| gaa ccg ttg atg gag caa gtc gga acg gaa gag ttt atc aaa agg ttc<br>Glu Pro Leu Met Glu Gln Val Gly Thr Glu Glu Phe Ile Lys Arg Phe<br>       115                  120                  125 | | 384 |
| ggt gat ggt gct tcg cgt gta gtg ctc agc ctt ccc ttc gct gag ggg<br>Gly Asp Gly Ala Ser Arg Val Val Leu Ser Leu Pro Phe Ala Glu Gly<br>130                    135                  140 | | 432 |
| agt tct agc gtt gaa tat att aat aac tgg gaa cag gcg aaa gcg tta<br>Ser Ser Ser Val Glu Tyr Ile Asn Asn Trp Glu Gln Ala Lys Ala Leu<br>145                    150                  155               160 | | 480 |
| agc gta gaa ctt gag att aat ttt gaa acc cgt gga aaa cgt ggc caa<br>Ser Val Glu Leu Glu Ile Asn Phe Glu Thr Arg Gly Lys Arg Gly Gln<br>                   165                  170               175 | | 528 |
| gat gcg atg tat gag tat atg gct caa gcc tgt gca gga aat cgt gtc<br>Asp Ala Met Tyr Glu Tyr Met Ala Gln Ala Cys Ala Gly Asn Arg Val<br>                      180                  185               190 | | 576 |
| agg cga tca gta ggt agc tca ttg tca tgc atc aac ctg gat tgg gat<br>Arg Arg Ser Val Gly Ser Ser Leu Ser Cys Ile Asn Leu Asp Trp Asp<br>             195                  200               205 | | 624 |
| gtt atc cgt gat aaa act aaa act aag atc gaa tct ctg aaa gaa cac<br>Val Ile Arg Asp Lys Thr Lys Thr Lys Ile Glu Ser Leu Lys Glu His<br>      210                  215                  220 | | 672 |
| ggt ccg atc aaa aac aaa atg agc gaa agc ccg aac aaa act gta tct<br>Gly Pro Ile Lys Asn Lys Met Ser Glu Ser Pro Asn Lys Thr Val Ser<br>225                    230                  235               240 | | 720 |
| gaa gaa aaa gct aaa cag tac ctg gaa gaa ttc cac cag act gca ctg<br>Glu Glu Lys Ala Lys Gln Tyr Leu Glu Glu Phe His Gln Thr Ala Leu<br>                      245                  250               255 | | 768 |
| gaa cac ccg gaa ctg tct gaa ctt aag acc gtt act ggt acc aac ccg<br>Glu His Pro Glu Leu Ser Glu Leu Lys Thr Val Thr Gly Thr Asn Pro<br>             260                  265               270 | | 816 |
| gta ttc gct ggt gct aac tac gct gct tgg gca gta aac gtt gct cag<br>Val Phe Ala Gly Ala Asn Tyr Ala Ala Trp Ala Val Asn Val Ala Gln<br>       275                  280                  285 | | 864 |
| gtt atc gat agc gaa act gct gat aac ctg gaa aaa act acc gcg gct<br>Val Ile Asp Ser Glu Thr Ala Asp Asn Leu Glu Lys Thr Thr Ala Ala<br>290                    295                  300 | | 912 |
| ctg tct atc ctg ccg ggt atc ggt agc gta atg ggc atc gca gac ggc<br>Leu Ser Ile Leu Pro Gly Ile Gly Ser Val Met Gly Ile Ala Asp Gly<br>305                    310                  315               320 | | 960 |
| gcc gtt cac cac aac act gaa gaa atc gtt gca cag tct atc gct ctg<br>Ala Val His His Asn Thr Glu Glu Ile Val Ala Gln Ser Ile Ala Leu<br>                      325                  330               335 | | 1008 |
| agc tct ctg atg gtt gct cag gcc atc ccg ctg gta ggt gaa ctg gtt<br>Ser Ser Leu Met Val Ala Gln Ala Ile Pro Leu Val Gly Glu Leu Val<br>             340                  345               350 | | 1056 |

| | | | | | | | | | | | | | | | | |
|---|---|---|---|---|---|---|---|---|---|---|---|---|---|---|---|---|
| gat | atc | ggt | ttc | gct | gca | tac | aac | ttc | gtt | gaa | agc | atc | atc | aac | ctg | 1104 |
| Asp | Ile | Gly | Phe | Ala | Ala | Tyr | Asn | Phe | Val | Glu | Ser | Ile | Ile | Asn | Leu | |
| | 355 | | | | | 360 | | | | | 365 | | | | | |
| ttc | cag | gtt | gtt | cac | aac | tct | tac | aac | cgc | ccg | gct | tac | tct | ccg | ggt | 1152 |
| Phe | Gln | Val | Val | His | Asn | Ser | Tyr | Asn | Arg | Pro | Ala | Tyr | Ser | Pro | Gly | |
| 370 | | | | | 375 | | | | | 380 | | | | | | |
| cac | aag | acg | cat | gca | tct | agc | gga | ggt | ggc | tct | agc | ggt | gga | gga | tcc | 1200 |
| His | Lys | Thr | His | Ala | Ser | Ser | Gly | Gly | Gly | Ser | Ser | Gly | Gly | Gly | Ser | |
| 385 | | | | | 390 | | | | | 395 | | | | | 400 | |
| gca | cct | act | tct | agc | tct | acc | aag | aaa | acc | cag | ctg | cag | ctc | gag | cac | 1248 |
| Ala | Pro | Thr | Ser | Ser | Ser | Thr | Lys | Lys | Thr | Gln | Leu | Gln | Leu | Glu | His | |
| | | | | 405 | | | | | 410 | | | | | 415 | | |
| ctg | ctg | ctg | gat | ttg | cag | atg | atc | ctg | aac | ggt | atc | aac | aat | tac | aag | 1296 |
| Leu | Leu | Leu | Asp | Leu | Gln | Met | Ile | Leu | Asn | Gly | Ile | Asn | Asn | Tyr | Lys | |
| | | | 420 | | | | | 425 | | | | | 430 | | | |
| aac | ccg | aaa | ctg | acg | cgt | atg | ctg | acc | ttc | aag | ttc | tac | atg | ccg | aag | 1344 |
| Asn | Pro | Lys | Leu | Thr | Arg | Met | Leu | Thr | Phe | Lys | Phe | Tyr | Met | Pro | Lys | |
| | | 435 | | | | | 440 | | | | | 445 | | | | |
| aag | gcc | acc | gaa | ctg | aaa | cac | ctg | ctg | cag | tgt | cta | gaa | gaa | gaa | ctg | 1392 |
| Lys | Ala | Thr | Glu | Leu | Lys | His | Leu | Leu | Gln | Cys | Leu | Glu | Glu | Glu | Leu | |
| 450 | | | | | 455 | | | | | 460 | | | | | | |
| aaa | ccg | ctg | gag | gaa | gtt | ctg | aac | ctg | gct | cag | tct | aaa | aac | ttc | cac | 1440 |
| Lys | Pro | Leu | Glu | Glu | Val | Leu | Asn | Leu | Ala | Gln | Ser | Lys | Asn | Phe | His | |
| 465 | | | | 470 | | | | | 475 | | | | | 480 | | |
| ctg | cgg | ccg | cgt | gac | ctg | atc | tct | aac | atc | aac | gta | atc | gtt | ctg | gaa | 1488 |
| Leu | Arg | Pro | Arg | Asp | Leu | Ile | Ser | Asn | Ile | Asn | Val | Ile | Val | Leu | Glu | |
| | | | | 485 | | | | | 490 | | | | | 495 | | |
| ctg | aag | ggc | tct | gaa | acc | acc | ttc | atg | tgt | gaa | tac | gct | gat | gag | acc | 1536 |
| Leu | Lys | Gly | Ser | Glu | Thr | Thr | Phe | Met | Cys | Glu | Tyr | Ala | Asp | Glu | Thr | |
| | | | 500 | | | | | 505 | | | | | 510 | | | |
| gca | acc | atc | gta | gaa | ttc | ctg | aac | cgt | tgg | atc | acc | ttc | tgt | cag | tct | 1584 |
| Ala | Thr | Ile | Val | Glu | Phe | Leu | Asn | Arg | Trp | Ile | Thr | Phe | Cys | Gln | Ser | |
| | | 515 | | | | | 520 | | | | | 525 | | | | |
| atc | atc | tct | acc | ctg | acc | | | | | | | | | | | 1602 |
| Ile | Ile | Ser | Thr | Leu | Thr | | | | | | | | | | | |
| | | 530 | | | | | | | | | | | | | | |

<210> SEQ ID NO 22
<211> LENGTH: 534
<212> TYPE: PRT
<213> ORGANISM: Artificial sequence
<220> FEATURE:
<223> OTHER INFORMATION: Corynephage omega: DT387(D8S)linkerIL2

<400> SEQUENCE: 22

Met Gly Ala Asp Asp Val Val Ser Ser Lys Ser Phe Val Met Glu
1               5                   10                  15

Asn Phe Ser Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

-continued

```
Glu Pro Leu Met Glu Gln Val Gly Thr Glu Phe Ile Lys Arg Phe
    115                 120                 125
Gly Asp Gly Ala Ser Arg Val Val Leu Ser Leu Pro Phe Ala Glu Gly
130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                165                 170                 175
Asp Ala Met Tyr Glu Tyr Met Ala Gln Ala Cys Ala Gly Asn Arg Val
            180                 185                 190
Arg Arg Ser Val Gly Ser Ser Leu Ser Cys Ile Asn Leu Asp Trp Asp
    195                 200                 205
Val Ile Arg Asp Lys Thr Lys Thr Lys Ile Glu Ser Leu Lys Glu His
210                 215                 220
Gly Pro Ile Lys Asn Lys Met Ser Glu Ser Pro Asn Lys Thr Val Ser
225                 230                 235                 240
Glu Glu Lys Ala Lys Gln Tyr Leu Glu Glu Phe His Gln Thr Ala Leu
                245                 250                 255
Glu His Pro Glu Leu Ser Glu Leu Lys Thr Val Thr Gly Thr Asn Pro
            260                 265                 270
Val Phe Ala Gly Ala Asn Tyr Ala Ala Trp Ala Val Asn Val Ala Gln
    275                 280                 285
Val Ile Asp Ser Glu Thr Ala Asp Asn Leu Glu Lys Thr Thr Ala Ala
290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
            340                 345                 350
Asp Ile Gly Phe Ala Ala Tyr Asn Phe Val Glu Ser Ile Ile Asn Leu
    355                 360                 365
Phe Gln Val Val His Asn Ser Tyr Asn Arg Pro Ala Tyr Ser Pro Gly
370                 375                 380
His Lys Thr His Ala Ser Ser Gly Gly Ser Ser Gly Gly Gly Ser
385                 390                 395                 400
Ala Pro Thr Ser Ser Ser Thr Lys Lys Thr Gln Leu Gln Leu Glu His
                405                 410                 415
Leu Leu Leu Asp Leu Gln Met Ile Leu Asn Gly Ile Asn Asn Tyr Lys
            420                 425                 430
Asn Pro Lys Leu Thr Arg Met Leu Thr Phe Lys Phe Tyr Met Pro Lys
    435                 440                 445
Lys Ala Thr Glu Leu Lys His Leu Leu Gln Cys Leu Glu Glu Glu Leu
450                 455                 460
Lys Pro Leu Glu Glu Val Leu Asn Leu Ala Gln Ser Lys Asn Phe His
465                 470                 475                 480
Leu Arg Pro Arg Asp Leu Ile Ser Asn Ile Asn Val Ile Val Leu Glu
                485                 490                 495
Leu Lys Gly Ser Glu Thr Thr Phe Met Cys Glu Tyr Ala Asp Glu Thr
            500                 505                 510
Ala Thr Ile Val Glu Phe Leu Asn Arg Trp Ile Thr Phe Cys Gln Ser
    515                 520                 525
Ile Ile Ser Thr Leu Thr
530
```

<210> SEQ ID NO 23
<211> LENGTH: 1602
<212> TYPE: DNA
<213> ORGANISM: Artificial sequence
<220> FEATURE:
<223> OTHER INFORMATION: Corynephage omega: DT387(D8E)linkerIL2
<220> FEATURE:
<221> NAME/KEY: CDS
<222> LOCATION: (1)..(1602)

<400> SEQUENCE: 23

| | | | | | | | | | | | | | | | | |
|---|---|---|---|---|---|---|---|---|---|---|---|---|---|---|---|---|
| atg | ggc | gct | gat | gat | gtt | gtt | gaa | tct | tct | aaa | tct | ttt | gtg | atg | gaa | 48 |
| Met | Gly | Ala | Asp | Asp | Val | Val | Glu | Ser | Ser | Lys | Ser | Phe | Val | Met | Glu | |
| 1 | | | | 5 | | | | | 10 | | | | | 15 | | |
| aac | ttt | tct | tcg | tac | cac | ggg | act | aaa | cct | ggt | tat | gta | gat | tcc | att | 96 |
| Asn | Phe | Ser | Ser | Tyr | His | Gly | Thr | Lys | Pro | Gly | Tyr | Val | Asp | Ser | Ile | |
| | | | | 20 | | | | | 25 | | | | | 30 | | |
| caa | aaa | ggt | ata | caa | aag | cca | aaa | tct | ggt | aca | caa | gga | aat | tat | gac | 144 |
| Gln | Lys | Gly | Ile | Gln | Lys | Pro | Lys | Ser | Gly | Thr | Gln | Gly | Asn | Tyr | Asp | |
| | | | 35 | | | | | 40 | | | | | 45 | | | |
| gat | gat | tgg | aaa | ggg | ttt | tat | agt | acc | gac | aat | aaa | tac | gac | gct | gcg | 192 |
| Asp | Asp | Trp | Lys | Gly | Phe | Tyr | Ser | Thr | Asp | Asn | Lys | Tyr | Asp | Ala | Ala | |
| 50 | | | | | 55 | | | | | 60 | | | | | | |
| gga | tac | tct | gta | gat | aat | gaa | aac | ccg | ctc | tct | gga | aaa | gct | gga | ggc | 240 |
| Gly | Tyr | Ser | Val | Asp | Asn | Glu | Asn | Pro | Leu | Ser | Gly | Lys | Ala | Gly | Gly | |
| 65 | | | | | 70 | | | | | 75 | | | | | 80 | |
| gtg | gtc | aaa | gtg | acg | tat | cca | gga | ctg | acg | aag | gtt | ctc | gca | cta | aaa | 288 |
| Val | Val | Lys | Val | Thr | Tyr | Pro | Gly | Leu | Thr | Lys | Val | Leu | Ala | Leu | Lys | |
| | | | | 85 | | | | | 90 | | | | | 95 | | |
| gtg | gat | aat | gcc | gaa | act | att | aag | aaa | gag | tta | ggt | tta | agt | ctc | act | 336 |
| Val | Asp | Asn | Ala | Glu | Thr | Ile | Lys | Lys | Glu | Leu | Gly | Leu | Ser | Leu | Thr | |
| | | | 100 | | | | | 105 | | | | | 110 | | | |
| gaa | ccg | ttg | atg | gag | caa | gtc | gga | acg | gaa | gag | ttt | atc | aaa | agg | ttc | 384 |
| Glu | Pro | Leu | Met | Glu | Gln | Val | Gly | Thr | Glu | Glu | Phe | Ile | Lys | Arg | Phe | |
| | | | 115 | | | | | 120 | | | | | 125 | | | |
| ggt | gat | ggt | gct | tcg | cgt | gta | gtg | ctc | agc | ctt | ccc | ttc | gct | gag | ggg | 432 |
| Gly | Asp | Gly | Ala | Ser | Arg | Val | Val | Leu | Ser | Leu | Pro | Phe | Ala | Glu | Gly | |
| | | | 130 | | | | | 135 | | | | | 140 | | | |
| agt | tct | agc | gtt | gaa | tat | att | aat | aac | tgg | gaa | cag | gcg | aaa | gcg | tta | 480 |
| Ser | Ser | Ser | Val | Glu | Tyr | Ile | Asn | Asn | Trp | Glu | Gln | Ala | Lys | Ala | Leu | |
| 145 | | | | | 150 | | | | | 155 | | | | | 160 | |
| agc | gta | gaa | ctt | gag | att | aat | ttt | gaa | acc | cgt | gga | aaa | cgt | ggc | caa | 528 |
| Ser | Val | Glu | Leu | Glu | Ile | Asn | Phe | Glu | Thr | Arg | Gly | Lys | Arg | Gly | Gln | |
| | | | | 165 | | | | | 170 | | | | | 175 | | |
| gat | gcg | atg | tat | gag | tat | atg | gct | caa | gcc | tgt | gca | gga | aat | cgt | gtc | 576 |
| Asp | Ala | Met | Tyr | Glu | Tyr | Met | Ala | Gln | Ala | Cys | Ala | Gly | Asn | Arg | Val | |
| | | | 180 | | | | | 185 | | | | | 190 | | | |
| agg | cga | tca | gta | ggt | agc | tca | ttg | tca | tgc | atc | aac | ctg | gat | tgg | gat | 624 |
| Arg | Arg | Ser | Val | Gly | Ser | Ser | Leu | Ser | Cys | Ile | Asn | Leu | Asp | Trp | Asp | |
| | | | 195 | | | | | 200 | | | | | 205 | | | |
| gtt | atc | cgt | gat | aaa | act | aaa | act | aag | atc | gaa | tct | ctg | aaa | gaa | cac | 672 |
| Val | Ile | Arg | Asp | Lys | Thr | Lys | Thr | Lys | Ile | Glu | Ser | Leu | Lys | Glu | His | |
| | | | 210 | | | | | 215 | | | | | 220 | | | |
| ggt | ccg | atc | aaa | aac | aaa | atg | agc | gaa | agc | ccg | aac | aaa | act | gta | tct | 720 |
| Gly | Pro | Ile | Lys | Asn | Lys | Met | Ser | Glu | Ser | Pro | Asn | Lys | Thr | Val | Ser | |
| 225 | | | | | 230 | | | | | 235 | | | | | 240 | |
| gaa | gaa | aaa | gct | aaa | cag | tac | ctg | gaa | gaa | ttc | cac | cag | act | gca | ctg | 768 |
| Glu | Glu | Lys | Ala | Lys | Gln | Tyr | Leu | Glu | Glu | Phe | His | Gln | Thr | Ala | Leu | |
| | | | | 245 | | | | | 250 | | | | | 255 | | |
| gaa | cac | ccg | gaa | ctg | tct | gaa | ctt | aag | acc | gtt | act | ggt | acc | aac | ccg | 816 |
| Glu | His | Pro | Glu | Leu | Ser | Glu | Leu | Lys | Thr | Val | Thr | Gly | Thr | Asn | Pro | |

```
                    260                 265                 270
gta ttc gct ggt gct aac tac gct gct tgg gca gta aac gtt gct cag        864
Val Phe Ala Gly Ala Asn Tyr Ala Ala Trp Ala Val Asn Val Ala Gln
        275                 280                 285 gtt atc gat agc gaa act gct gat aac ctg gaa aaa act acc gcg gct        912
Val Ile Asp Ser Glu Thr Ala Asp Asn Leu Glu Lys Thr Thr Ala Ala
    290                 295                 300 ctg tct atc ctg ccg ggt atc ggt agc gta atg ggc atc gca gac ggc        960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg       1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt       1056
Ser Ser Leu Met Val Ala Gln Ala Ile Pro Leu Val Gly Glu Leu Val
            340                 345                 350 gat atc ggt ttc gct gca tac aac ttc gtt gaa agc atc atc aac ctg       1104
Asp Ile Gly Phe Ala Ala Tyr Asn Phe Val Glu Ser Ile Ile Asn Leu
        355                 360                 365 ttc cag gtt gtt cac aac tct tac aac cgc ccg gct tac tct ccg ggt       1152
Phe Gln Val Val His Asn Ser Tyr Asn Arg Pro Ala Tyr Ser Pro Gly
    370                 375                 380 cac aag acg cat gca tct agc gga ggt ggc tct agc ggt gga gga tcc       1200
His Lys Thr His Ala Ser Ser Gly Gly Gly Ser Ser Gly Gly Gly Ser
385                 390                 395                 400 gca cct act tct agc tct acc aag aaa acc cag ctg cag ctc gag cac       1248
Ala Pro Thr Ser Ser Ser Thr Lys Lys Thr Gln Leu Gln Leu Glu His
                405                 410                 415 ctg ctg ctg gat ttg cag atg atc ctg aac ggt atc aac aat tac aag       1296
Leu Leu Leu Asp Leu Gln Met Ile Leu Asn Gly Ile Asn Asn Tyr Lys
            420                 425                 430 aac ccg aaa ctg acg cgt atg ctg acc ttc aag ttc tac atg ccg aag       1344
Asn Pro Lys Leu Thr Arg Met Leu Thr Phe Lys Phe Tyr Met Pro Lys
        435                 440                 445 aag gcc acc gaa ctg aaa cac ctg ctg cag tgt cta gaa gaa gaa ctg       1392
Lys Ala Thr Glu Leu Lys His Leu Leu Gln Cys Leu Glu Glu Glu Leu
    450                 455                 460 aaa ccg ctg gag gaa gtt ctg aac ctg gct cag tct aaa aac ttc cac       1440
Lys Pro Leu Glu Glu Val Leu Asn Leu Ala Gln Ser Lys Asn Phe His
465                 470                 475                 480 ctg cgg ccg cgt gac ctg atc tct aac atc aac gta atc gtt ctg gaa       1488
Leu Arg Pro Arg Asp Leu Ile Ser Asn Ile Asn Val Ile Val Leu Glu
                485                 490                 495 ctg aag ggc tct gaa acc acc ttc atg tgt gaa tac gct gat gag acc       1536
Leu Lys Gly Ser Glu Thr Thr Phe Met Cys Glu Tyr Ala Asp Glu Thr
            500                 505                 510 gca acc atc gta gaa ttc ctg aac cgt tgg atc acc ttc tgt cag tct       1584
Ala Thr Ile Val Glu Phe Leu Asn Arg Trp Ile Thr Phe Cys Gln Ser
        515                 520                 525 atc atc tct acc ctg acc                                               1602
Ile Ile Ser Thr Leu Thr
    530

<210> SEQ ID NO 24
<211> LENGTH: 534
<212> TYPE: PRT
<213> ORGANISM: Artificial sequence
<220> FEATURE:
<223> OTHER INFORMATION: Corynephage omega: DT387(D8E)linkerIL2

<400> SEQUENCE: 24
```

-continued

```
Met Gly Ala Asp Asp Val Val Glu Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Ser Ser Gly Gly Ser Ser Gly Gly Gly Ser
385                 390                 395                 400

Ala Pro Thr Ser Ser Ser Thr Lys Lys Thr Gln Leu Gln Leu Glu His
                405                 410                 415

Leu Leu Leu Asp Leu Gln Met Ile Leu Asn Gly Ile Asn Asn Tyr Lys
            420                 425                 430
```

```
Asn Pro Lys Leu Thr Arg Met Leu Thr Phe Lys Phe Tyr Met Pro Lys
        435                 440                 445

Lys Ala Thr Glu Leu Lys His Leu Leu Gln Cys Leu Glu Glu Glu Leu
    450                 455                 460

Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
                485                 490                 495

Leu Lys Gly Ser Glu Thr Thr Phe Met Cys Glu Tyr Ala Asp Glu Thr
            500                 505                 510

Ala Thr Ile Val Glu Phe Leu Asn Arg Trp Ile Thr Phe Cys Gln Ser
        515                 520                 525

Ile Ile Ser Thr Leu Thr
        530

<210> SEQ ID NO 25
<211> LENGTH: 1602
<212> TYPE: DNA
<213> ORGANISM: Artificial sequence
<220> FEATURE:
<223> OTHER INFORMATION: Corynephage omega: DT387(V29A)linkerIL2
<220> FEATURE:
<221> NAME/KEY: CDS
<222> LOCATION: (1)..(1602)

<400> SEQUENCE: 25
```

| | | | | | | | | | | | | | | | | |
|---|---|---|---|---|---|---|---|---|---|---|---|---|---|---|---|---|
| atg | ggc | gct | gat | gat | gtt | gtt | gat | tct | tct | aaa | tct | ttt | gtg | atg | gaa | 48 |
| Met | Gly | Ala | Asp | Asp | Val | Val | Asp | Ser | Ser | Lys | Ser | Phe | Val | Met | Glu | |
| 1 | | | | 5 | | | | | 10 | | | | | 15 | | |
| aac | ttt | tct | tcg | tac | cac | ggg | act | aaa | cct | ggt | tat | gca | gat | tcc | att | 96 |
| Asn | Phe | Ser | Ser | Tyr | His | Gly | Thr | Lys | Pro | Gly | Tyr | Ala | Asp | Ser | Ile | |
| | | | 20 | | | | | 25 | | | | | 30 | | | |
| caa | aaa | ggt | ata | caa | aag | cca | aaa | tct | ggt | aca | caa | gga | aat | tat | gac | 144 |
| Gln | Lys | Gly | Ile | Gln | Lys | Pro | Lys | Ser | Gly | Thr | Gln | Gly | Asn | Tyr | Asp | |
| | | 35 | | | | | 40 | | | | | 45 | | | | |
| gat | gat | tgg | aaa | ggg | ttt | tat | agt | acc | gac | aat | aaa | tac | gac | gct | gcg | 192 |
| Asp | Asp | Trp | Lys | Gly | Phe | Tyr | Ser | Thr | Asp | Asn | Lys | Tyr | Asp | Ala | Ala | |
| 50 | | | | | 55 | | | | | 60 | | | | | | |
| gga | tac | tct | gta | gat | aat | gaa | aac | ccg | ctc | tct | gga | aaa | gct | gga | ggc | 240 |
| Gly | Tyr | Ser | Val | Asp | Asn | Glu | Asn | Pro | Leu | Ser | Gly | Lys | Ala | Gly | Gly | |
| 65 | | | | | 70 | | | | | 75 | | | | | 80 | |
| gtg | gtc | aaa | gtg | acg | tat | cca | gga | ctg | acg | aag | gtt | ctc | gca | cta | aaa | 288 |
| Val | Val | Lys | Val | Thr | Tyr | Pro | Gly | Leu | Thr | Lys | Val | Leu | Ala | Leu | Lys | |
| | | | | 85 | | | | | 90 | | | | | 95 | | |
| gtg | gat | aat | gcc | gaa | act | att | aag | aaa | gag | tta | ggt | tta | agt | ctc | act | 336 |
| Val | Asp | Asn | Ala | Glu | Thr | Ile | Lys | Lys | Glu | Leu | Gly | Leu | Ser | Leu | Thr | |
| | | | 100 | | | | | 105 | | | | | 110 | | | |
| gaa | ccg | ttg | atg | gag | caa | gtc | gga | acg | gaa | gag | ttt | atc | aaa | agg | ttc | 384 |
| Glu | Pro | Leu | Met | Glu | Gln | Val | Gly | Thr | Glu | Glu | Phe | Ile | Lys | Arg | Phe | |
| | | | 115 | | | | | 120 | | | | | 125 | | | |
| ggt | gat | ggt | gct | tcg | cgt | gta | gtg | ctc | agc | ctt | ccc | ttc | gct | gag | ggg | 432 |
| Gly | Asp | Gly | Ala | Ser | Arg | Val | Val | Leu | Ser | Leu | Pro | Phe | Ala | Glu | Gly | |
| | | 130 | | | | | 135 | | | | | 140 | | | | |
| agt | tct | agc | gtt | gaa | tat | att | aat | aac | tgg | gaa | cag | gcg | aaa | gcg | tta | 480 |
| Ser | Ser | Ser | Val | Glu | Tyr | Ile | Asn | Asn | Trp | Glu | Gln | Ala | Lys | Ala | Leu | |
| 145 | | | | | 150 | | | | | 155 | | | | | 160 | |
| agc | gta | gaa | ctt | gag | att | aat | ttt | gaa | acc | cgt | gga | aaa | cgt | ggc | caa | 528 |
| Ser | Val | Glu | Leu | Glu | Ile | Asn | Phe | Glu | Thr | Arg | Gly | Lys | Arg | Gly | Gln | |
| | | | | 165 | | | | | 170 | | | | | 175 | | |
| gat | gcg | atg | tat | gag | tat | atg | gct | caa | gcc | tgt | gca | gga | aat | cgt | gtc | 576 |

-continued

Asp Ala Met Tyr Glu Tyr Met Ala Gln Ala Cys Ala Gly Asn Arg Val
        180                 185                 190 agg cga tca gta ggt agc tca ttg tca tgc atc aac ctg gat tgg gat      624
Arg Arg Ser Val Gly Ser Ser Leu Ser Cys Ile Asn Leu Asp Trp Asp
        195                 200                 205 gtt atc cgt gat aaa act aaa act aag atc gaa tct ctg aaa gaa cac      672
Val Ile Arg Asp Lys Thr Lys Thr Lys Ile Glu Ser Leu Lys Glu His
        210                 215                 220 ggt ccg atc aaa aac aaa atg agc gaa agc ccg aac aaa act gta tct      720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg      768
Glu Glu Lys Ala Lys Gln Tyr Leu Glu Glu Phe His Gln Thr Ala Leu
                245                 250                 255 gaa cac ccg gaa ctg tct gaa ctt aag acc gtt act ggt acc aac ccg      816
Glu His Pro Glu Leu Ser Glu Leu Lys Thr Val Thr Gly Thr Asn Pro
            260                 265                 270 gta ttc gct ggt gct aac tac gct gct tgg gca gta aac gtt gct cag      864
Val Phe Ala Gly Ala Asn Tyr Ala Ala Trp Ala Val Asn Val Ala Gln
        275                 280                 285 gtt atc gat agc gaa act gct gat aac ctg gaa aaa act acc gcg gct      912
Val Ile Asp Ser Glu Thr Ala Asp Asn Leu Glu Lys Thr Thr Ala Ala
    290                 295                 300 ctg tct atc ctg ccg ggt atc ggt agc gta atg ggc atc gca gac ggc      960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg     1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt     1056
Ser Ser Leu Met Val Ala Gln Ala Ile Pro Leu Val Gly Glu Leu Val
            340                 345                 350 gat atc ggt ttc gct gca tac aac ttc gtt gaa agc atc atc aac ctg     1104
Asp Ile Gly Phe Ala Ala Tyr Asn Phe Val Glu Ser Ile Ile Asn Leu
        355                 360                 365 ttc cag gtt gtt cac aac tct tac aac cgc ccg gct tac tct ccg ggt     1152
Phe Gln Val Val His Asn Ser Tyr Asn Arg Pro Ala Tyr Ser Pro Gly
    370                 375                 380 cac aag acg cat gca tct agc gga ggt ggc tct agc ggt gga gga tcc     1200
His Lys Thr His Ala Ser Ser Gly Gly Gly Ser Ser Gly Gly Gly Ser
385                 390                 395                 400 gca cct act tct agc tct acc aag aaa acc cag ctg cag ctc gag cac     1248
Ala Pro Thr Ser Ser Ser Thr Lys Lys Thr Gln Leu Gln Leu Glu His
                405                 410                 415 ctg ctg ctg gat ttg cag atg atc ctg aac ggt atc aac aat tac aag     1296
Leu Leu Leu Asp Leu Gln Met Ile Leu Asn Gly Ile Asn Asn Tyr Lys
            420                 425                 430 aac ccg aaa ctg acg cgt atg ctg acc ttc aag ttc tac atg ccg aag     1344
Asn Pro Lys Leu Thr Arg Met Leu Thr Phe Lys Phe Tyr Met Pro Lys
        435                 440                 445 aag gcc acc gaa ctg aaa cac ctg ctg cag tgt cta gaa gaa gaa ctg     1392
Lys Ala Thr Glu Leu Lys His Leu Leu Gln Cys Leu Glu Glu Glu Leu
    450                 455                 460 aaa ccg ctg gag gaa gtt ctg aac ctg gct cag tct aaa aac ttc cac     1440
Lys Pro Leu Glu Glu Val Leu Asn Leu Ala Gln Ser Lys Asn Phe His
465                 470                 475                 480 ctg cgg ccg cgt gac ctg atc tct aac atc aac gta atc gtt ctg gaa     1488
Leu Arg Pro Arg Asp Leu Ile Ser Asn Ile Asn Val Ile Val Leu Glu
                485                 490                 495 ctg aag ggc tct gaa acc acc ttc atg tgt gaa tac gct gat gag acc     1536

```
Leu Lys Gly Ser Glu Thr Thr Phe Met Cys Glu Tyr Ala Asp Glu Thr
            500                 505                 510 gca acc atc gta gaa ttc ctg aac cgt tgg atc acc ttc tgt cag tct    1584
Ala Thr Ile Val Glu Phe Leu Asn Arg Trp Ile Thr Phe Cys Gln Ser
            515                 520                 525 atc atc tct acc ctg acc                                             1602
Ile Ile Ser Thr Leu Thr
            530
```

<210> SEQ ID NO 26
<211> LENGTH: 534
<212> TYPE: PRT
<213> ORGANISM: Artificial sequence
<220> FEATURE:
<223> OTHER INFORMATION: Corynephage omega: DT387(V29A)linkerIL2

<400> SEQUENCE: 26

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Ala Asp Ser Ile
            20

```
Ala Val His His Asn Thr Glu Glu Ile Val Ala Gln Ser Ile Ala Leu
            325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
        370                 375                 380

His Lys Thr His Ala Ser Ser Gly Gly Ser Ser Gly Gly Gly Ser
385                 390                 395                 400

Ala Pro Thr Ser Ser Ser Thr Lys Lys Thr Gln Leu Gln Leu Glu His
                405                 410                 415

Leu Leu Leu Asp Leu Gln Met Ile Leu Asn Gly Ile Asn Asn Tyr Lys
            420                 425                 430

Asn Pro Lys Leu Thr Arg Met Leu Thr Phe Lys Phe Tyr Met Pro Lys
            435                 440                 445

Lys Ala Thr Glu Leu Lys His Leu Leu Gln Cys Leu Glu Glu Glu Leu
        450                 455                 460

Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
                485                 490                 495

Leu Lys Gly Ser Glu Thr Thr Phe Met Cys Glu Tyr Ala Asp Glu Thr
            500                 505                 510

Ala Thr Ile Val Glu Phe Leu Asn Arg Trp Ile Thr Phe Cys Gln Ser
        515                 520                 525

Ile Ile Ser Thr Leu Thr
        530

<210> SEQ ID NO 27
<211> LENGTH: 534
<212> TYPE: PRT
<213> ORGANISM: Artificial sequence
<220> FEATURE:
<223> OTHER INFORMATION: Corynephage omega: DT387(L290A)linkerIL2

<400> SEQUENCE: 27

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
            85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140
```

```
Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ala Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Ser Ser Gly Gly Ser Ser Gly Gly Gly Gly Ser
385                 390                 395                 400

Ala Pro Thr Ser Ser Ser Thr Lys Lys Thr Gln Leu Gln Leu Glu His
                405                 410                 415

Leu Leu Leu Asp Leu Gln Met Ile Leu Asn Gly Ile Asn Asn Tyr Lys
            420                 425                 430

Asn Pro Lys Leu Thr Arg Met Leu Thr Phe Lys Phe Tyr Met Pro Lys
        435                 440                 445

Lys Ala Thr Glu Leu Lys His Leu Leu Gln Cys Leu Glu Glu Glu Leu
    450                 455                 460

Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
                485                 490                 495

Leu Lys Gly Ser Glu Thr Thr Phe Met Cys Glu Tyr Ala Asp Glu Thr
            500                 505                 510

Ala Thr Ile Val Glu Phe Leu Asn Arg Trp Ile Thr Phe Cys Gln Ser
        515                 520                 525

Ile Ile Ser Thr Leu Thr
    530

<210> SEQ ID NO 28
<211> LENGTH: 1602
<212> TYPE: DNA
<213> ORGANISM: Artificial sequence
```

```
<220> FEATURE:
<223> OTHER INFORMATION: Corynephage omega: DT387(L291E)linkerIL2
<220> FEATURE:
<221> NAME/KEY: CDS
<222> LOCATION: (1)..(1602)

<400> SEQUENCE: 28 atg ggc gct gat gat gtt gtt gat tct tct aaa tct ttt gtg atg gaa      48
Met Gly Ala Asp Asp Val Val Asp Ser Ser Lys Ser Phe Val Met Glu
1               5                   10                  15 aac ttt tct tcg tac cac ggg act aaa cct ggt tat gta gat tcc att      96
Asn Phe Ser Ser Tyr His Gly Thr Lys Pro Gly Tyr Val Asp Ser Ile
                20                  25                  30 caa aaa ggt ata caa aag cca aaa tct gga aca caa gga aat tat gac      144
Gln Lys Gly Ile Gln Lys Pro Lys Ser Gly Thr Gln Gly Asn Tyr Asp
            35                  40                  45 gat gat tgg aaa ggg ttt tat agt acc gac aat aaa tac gac gct gcg      192
Asp Asp Trp Lys Gly Phe Tyr Ser Thr Asp Asn Lys Tyr Asp Ala Ala
        50                  55                  60 gga tac tct gta gat aat gaa aac ccg ctc tct gga aaa gct gga ggc      240
Gly Tyr Ser Val Asp Asn Glu Asn Pro Leu Ser Gly Lys Ala Gly Gly
65                  70                  75                  80 gtg gtc aaa gtg acg tat cca gga ctg acg aag gtt ctc gca cta aaa      288
Val Val Lys Val Thr Tyr Pro Gly Leu Thr Lys Val Leu Ala Leu Lys
                85                  90                  95 gtg gat aat gcc gaa act att aag aaa gag tta ggt tta agt ctc act      336
Val Asp Asn Ala Glu Thr Ile Lys Lys Glu Leu Gly Leu Ser Leu Thr
                100                 105                 110 gaa ccg ttg atg gag caa gtc gga acg gaa gag ttt atc aaa agg ttc      384
Glu Pro Leu Met Glu Gln Val Gly Thr Glu Glu Phe Ile Lys Arg Phe
            115                 120                 125 ggt gat ggt gct tcg cgt gta gtg ctc agc ctt ccc ttc gct gag ggg      432
Gly Asp Gly Ala Ser Arg Val Val Leu Ser Leu Pro Phe Ala Glu Gly
        130                 135                 140 agt tct agc gtt gaa tat att aat aac tgg gaa cag gcg aaa gcg tta      480
Ser Ser Ser Val Glu Tyr Ile Asn Asn Trp Glu Gln Ala Lys Ala Leu
145                 150                 155                 160 agc gta gaa ctt gag att aat ttt gaa acc cgt gaa aaa cgt ggc caa      528
Ser Val Glu Leu Glu Ile Asn Phe Glu Thr Arg Glu Lys Arg Gly Gln
                165                 170                 175 gat gcg atg tat gag tat atg gct caa gcc tgt gca gga aat cgt gtc      576
Asp Ala Met Tyr Glu Tyr Met Ala Gln Ala Cys Ala Gly Asn Arg Val
            180                 185                 190 agg cga tca gta ggt agc tca ttg tca tgc atc aac ctg gat tgg gat      624
Arg Arg Ser Val Gly Ser Ser Leu Ser Cys Ile Asn Leu Asp Trp Asp
        195                 200                 205 gtt atc cgt gat aaa act aaa act aag atc gaa tct ctg aaa gaa cac      672
Val Ile Arg Asp Lys Thr Lys Thr Lys Ile Glu Ser Leu Lys Glu His
    210                 215                 220 ggt ccg atc aaa aac aaa atg agc gaa agc ccg aac aaa act gta tct      720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg      768
Glu Glu Lys Ala Lys Gln Tyr Leu Glu Glu Phe His Gln Thr Ala Leu
                245                 250                 255 gaa cac ccg gaa ctg tct gaa ctt aag acc gtt act ggt acc aac ccg      816
Glu His Pro Glu Leu Ser Glu Leu Lys Thr Val Thr Gly Thr Asn Pro
            260                 265                 270 gta ttc gct ggt gct aac tac gct gct tgg gca gta aac gtt gct cag      864
Val Phe Ala Gly Ala Asn Tyr Ala Ala Trp Ala Val Asn Val Ala Gln
        275                 280                 285
```

```
gtt atc gaa agc gaa act gct gat aac ctg gaa aaa act acc gcg gct      912
Val Ile Glu Ser Glu Thr Ala Asp Asn Leu Glu Lys Thr Thr Ala Ala
    290                 295                 300 ctg tct atc ctg ccg ggt atc ggt agc gta atg ggc atc gca gac ggc      960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg     1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt     1056
Ser Ser Leu Met Val Ala Gln Ala Ile Pro Leu Val Gly Glu Leu Val
            340                 345                 350 gat atc ggt ttc gct gca tac aac ttc gtt gaa agc atc atc aac ctg     1104
Asp Ile Gly Phe Ala Ala Tyr Asn Phe Val Glu Ser Ile Ile Asn Leu
        355                 360                 365 ttc cag gtt gtt cac aac tct tac aac cgc ccg gct tac tct ccg ggt     1152
Phe Gln Val Val His Asn Ser Tyr Asn Arg Pro Ala Tyr Ser Pro Gly
    370                 375                 380 cac aag acg cat gca tct agc gga ggt ggc tct agc ggt gga gga tcc     1200
His Lys Thr His Ala Ser Ser Gly Gly Gly Ser Ser Gly Gly Gly Ser
385                 390                 395                 400 gca cct act tct agc tct acc aag aaa acc cag ctg cag ctc gag cac     1248
Ala Pro Thr Ser Ser Ser Thr Lys Lys Thr Gln Leu Gln Leu Glu His
                405                 410                 415 ctg ctg ctg gat ttg cag atg atc ctg aac ggt atc aac aat tac aag     1296
Leu Leu Leu Asp Leu Gln Met Ile Leu Asn Gly Ile Asn Asn Tyr Lys
            420                 425                 430 aac ccg aaa ctg acg cgt atg ctg acc ttc aag ttc tac atg ccg aag     1344
Asn Pro Lys Leu Thr Arg Met Leu Thr Phe Lys Phe Tyr Met Pro Lys
        435                 440                 445 aag gcc acc gaa ctg aaa cac ctg ctg cag tgt cta gaa gaa gaa ctg     1392
Lys Ala Thr Glu Leu Lys His Leu Leu Gln Cys Leu Glu Glu Glu Leu
    450                 455                 460 aaa ccg ctg gag gaa gtt ctg aac ctg gct cag tct aaa aac ttc cac     1440
Lys Pro Leu Glu Glu Val Leu Asn Leu Ala Gln Ser Lys Asn Phe His
465                 470                 475                 480 ctg cgg ccg cgt gac ctg atc tct aac atc aac gta atc gtt ctg gaa     1488
Leu Arg Pro Arg Asp Leu Ile Ser Asn Ile Asn Val Ile Val Leu Glu
                485                 490                 495 ctg aag ggc tct gaa acc acc ttc atg tgt gaa tac gct gat gag acc     1536
Leu Lys Gly Ser Glu Thr Thr Phe Met Cys Glu Tyr Ala Asp Glu Thr
            500                 505                 510 gca acc atc gta gaa ttc ctg aac cgt tgg atc acc ttc tgt cag tct     1584
Ala Thr Ile Val Glu Phe Leu Asn Arg Trp Ile Thr Phe Cys Gln Ser
        515                 520                 525 atc atc tct acc ctg acc                                             1602
Ile Ile Ser Thr Leu Thr
    530
```

<210> SEQ ID NO 29
<211> LENGTH: 534
<212> TYPE: PRT
<213> ORGANISM: Artificial sequence
<220> FEATURE:
<223> OTHER INFORMATION: Corynephage omega: DT387(L291E)linkerIL2

<400> SEQUENCE: 29

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30
```

```
Gln Lys Gly Ile Gln Lys Pro Lys Ser Gly Thr Gln Gly Asn Tyr Asp
         35                  40                  45

Asp Asp Trp Lys Gly Phe Tyr Ser Thr Asp Asn Lys Tyr Asp Ala Ala
 50                      55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
                100                 105                 110

Glu Pro Leu Met Glu Gln Val Gly Thr Glu Phe Ile Lys Arg Phe
            115                 120                 125

Gly Asp Gly Ala Ser Arg Val Val Leu Ser Leu Pro Phe Ala Glu Gly
            130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Glu Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Glu Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr His Ala Ser Ser Gly Gly Ser Gly Gly Gly Ser
385                 390                 395                 400

Ala Pro Thr Ser Ser Ser Thr Lys Lys Thr Gln Leu Gln Leu Glu His
                405                 410                 415

Leu Leu Leu Asp Leu Gln Met Ile Leu Asn Gly Ile Asn Asn Tyr Lys
            420                 425                 430

Asn Pro Lys Leu Thr Arg Met Leu Thr Phe Lys Phe Tyr Met Pro Lys
        435                 440                 445

Lys Ala Thr Glu Leu Lys His Leu Leu Gln Cys Leu Glu Glu Glu Leu
450                 455                 460
```

```
Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
            485                 490                 495

Leu Lys Gly Ser Glu Thr Thr Phe Met Cys Glu Tyr Ala Asp Glu Thr
        500                 505                 510

Ala Thr Ile Val Glu Phe Leu Asn Arg Trp Ile Thr Phe Cys Gln Ser
            515                 520                 525

Ile Ile Ser Thr Leu Thr
        530

<210> SEQ ID NO 30
<211> LENGTH: 2097
<212> TYPE: DNA
<213> ORGANISM: Artificial sequence
<220> FEATURE:
<223> OTHER INFORMATION: Corynephage omega: DT387(V7AV29A)linkerIL2
<220> FEATURE:
<221> NAME/KEY: CDS
<222> LOCATION: (1)..(1602)

<400> SEQUENCE: 30 atg ggc gct gat gat gtt gct gat tct tct aaa tct ttt gtg atg gaa      48
Met Gly Ala Asp Asp Val Ala Asp Ser Ser Lys Ser Phe Val Met Glu
1               5                   10                  15 aac ttt tct tcg tac cac ggg act aaa cct ggt tat gca gat tcc att      96
Asn Phe Ser Ser Tyr His Gly Thr Lys Pro Gly Tyr Ala Asp Ser Ile
                20                  25                  30 caa aaa ggt ata caa aag cca aaa tct ggt aca caa gga aat tat gac     144
Gln Lys Gly Ile Gln Lys Pro Lys Ser Gly Thr Gln Gly Asn Tyr Asp
            35                  40                  45 gat gat tgg aaa ggg ttt tat agt acc gac aat aaa tac gac gct gcg     192
Asp Asp Trp Lys Gly Phe Tyr Ser Thr Asp Asn Lys Tyr Asp Ala Ala
        50                  55                  60 gga tac tct gta gat aat gaa aac ccg ctc tct gga aaa gct gga ggc     240
Gly Tyr Ser Val Asp Asn Glu Asn Pro Leu Ser Gly Lys Ala Gly Gly
65                  70                  75                  80 gtg gtc aaa gtg acg tat cca gga ctg acg aag gtt ctc gca cta aaa     288
Val Val Lys Val Thr Tyr Pro Gly Leu Thr Lys Val Leu Ala Leu Lys
                85                  90                  95 gtg gat aat gcc gaa act att aag aaa gag tta ggt tta agt ctc act     336
Val Asp Asn Ala Glu Thr Ile Lys Lys Glu Leu Gly Leu Ser Leu Thr
                100                 105                 110 gaa ccg ttg atg gag caa gtc gga acg gaa gag ttt atc aaa agg ttc     384
Glu Pro Leu Met Glu Gln Val Gly Thr Glu Glu Phe Ile Lys Arg Phe
            115                 120                 125 ggt gat ggt gct tcg cgt gta gtg ctc agc ctt ccc ttc gct gag ggg     432
Gly Asp Gly Ala Ser Arg Val Val Leu Ser Leu Pro Phe Ala Glu Gly
        130                 135                 140 agt tct agc gtt gaa tat att aat aac tgg gaa cag gcg aaa gcg tta     480
Ser Ser Ser Val Glu Tyr Ile Asn Asn Trp Glu Gln Ala Lys Ala Leu
145                 150                 155                 160 agc gta gaa ctt gag att aat ttt gaa acc cgt gga aaa cgt ggc caa     528
Ser Val Glu Leu Glu Ile Asn Phe Glu Thr Arg Gly Lys Arg Gly Gln
                165                 170                 175 gat gcg atg tat gag tat atg gct caa gcc tgt gca gga aat cgt gtc     576
Asp Ala Met Tyr Glu Tyr Met Ala Gln Ala Cys Ala Gly Asn Arg Val
            180                 185                 190 agg cga tca gta ggt agc tca ttg tca tgc atc aac ctg gat tgg gat     624
Arg Arg Ser Val Gly Ser Ser Leu Ser Cys Ile Asn Leu Asp Trp Asp
        195                 200                 205
```

| | | |
|---|---|---|
| gtt atc cgt gat aaa act aaa act aag atc gaa tct ctg aaa gaa cac<br>Val Ile Arg Asp Lys Thr Lys Thr Lys Ile Glu Ser Leu Lys Glu His<br>210 215 220 | | 672 |
| ggt ccg atc aaa aac aaa atg agc gaa agc ccg aac aaa act gta tct<br>Gly Pro Ile Lys Asn Lys Met Ser Glu Ser Pro Asn Lys Thr Val Ser<br>225 230 235 240 | | 720 |
| gaa gaa aaa gct aaa cag tac ctg gaa gaa ttc cac cag act gca ctg<br>Glu Glu Lys Ala Lys Gln Tyr Leu Glu Glu Phe His Gln Thr Ala Leu<br>245 250 255 | | 768 |
| gaa cac ccg gaa ctg tct gaa ctt aag acc gtt act ggt acc aac ccg<br>Glu His Pro Glu Leu Ser Glu Leu Lys Thr Val Thr Gly Thr Asn Pro<br>260 265 270 | | 816 |
| gta ttc gct ggt gct aac tac gct gct tgg gca gta aac gtt gct cag<br>Val Phe Ala Gly Ala Asn Tyr Ala Ala Trp Ala Val Asn Val Ala Gln<br>275 280 285 | | 864 |
| gtt atc gat agc gaa act gct gat aac ctg gaa aaa act acc gcg gct<br>Val Ile Asp Ser Glu Thr Ala Asp Asn Leu Glu Lys Thr Thr Ala Ala<br>290 295 300 | | 912 |
| ctg tct atc ctg ccg ggt atc ggt agc gta atg ggc atc gca gac ggc<br>Leu Ser Ile Leu Pro Gly Ile Gly Ser Val Met Gly Ile Ala Asp Gly<br>305 310 315 320 | | 960 |
| gcc gtt cac cac aac act gaa gaa atc gtt gca cag tct atc gct ctg<br>Ala Val His His Asn Thr Glu Glu Ile Val Ala Gln Ser Ile Ala Leu<br>325 330 335 | | 1008 |
| agc tct ctg atg gtt gct cag gcc atc ccg ctg gta ggt gaa ctg gtt<br>Ser Ser Leu Met Val Ala Gln Ala Ile Pro Leu Val Gly Glu Leu Val<br>340 345 350 | | 1056 |
| gat atc ggt ttc gct gca tac aac ttc gtt gaa agc atc atc aac ctg<br>Asp Ile Gly Phe Ala Ala Tyr Asn Phe Val Glu Ser Ile Ile Asn Leu<br>355 360 365 | | 1104 |
| ttc cag gtt gtt cac aac tct tac aac cgc ccg gct tac tct ccg ggt<br>Phe Gln Val Val His Asn Ser Tyr Asn Arg Pro Ala Tyr Ser Pro Gly<br>370 375 380 | | 1152 |
| cac aag acg cat gca tct agc gga ggt ggc tct agc ggt gga gga tcc<br>His Lys Thr His Ala Ser Ser Gly Gly Gly Ser Ser Gly Gly Gly Ser<br>385 390 395 400 | | 1200 |
| gca cct act tct agc tct acc aag aaa acc cag ctg cag ctc gag cac<br>Ala Pro Thr Ser Ser Ser Thr Lys Lys Thr Gln Leu Gln Leu Glu His<br>405 410 415 | | 1248 |
| ctg ctg ctg gat ttg cag atg atc ctg aac ggt atc aac aat tac aag<br>Leu Leu Leu Asp Leu Gln Met Ile Leu Asn Gly Ile Asn Asn Tyr Lys<br>420 425 430 | | 1296 |
| aac ccg aaa ctg acg cgt atg ctg acc ttc aag ttc tac atg ccg aag<br>Asn Pro Lys Leu Thr Arg Met Leu Thr Phe Lys Phe Tyr Met Pro Lys<br>435 440 445 | | 1344 |
| aag gcc acc gaa ctg aaa cac ctg ctg cag tgt cta gaa gaa gaa ctg<br>Lys Ala Thr Glu Leu Lys His Leu Leu Gln Cys Leu Glu Glu Glu Leu<br>450 455 460 | | 1392 |
| aaa ccg ctg gag gaa gtt ctg aac ctg gct cag tct aaa aac ttc cac<br>Lys Pro Leu Glu Glu Val Leu Asn Leu Ala Gln Ser Lys Asn Phe His<br>465 470 475 480 | | 1440 |
| ctg cgg ccg cgt gac ctg atc tct aac atc aac gta atc gtt ctg gaa<br>Leu Arg Pro Arg Asp Leu Ile Ser Asn Ile Asn Val Ile Val Leu Glu<br>485 490 495 | | 1488 |
| ctg aag ggc tct gaa acc acc ttc atg tgt gaa gca cag tct atc gct<br>Leu Lys Gly Ser Glu Thr Thr Phe Met Cys Glu Ala Gln Ser Ile Ala<br>500 505 510 | | 1536 |
| ctg agc tct ctg atg gtt gct cag gcc atc ccg ctg gta ggt gaa ctg<br>Leu Ser Ser Leu Met Val Ala Gln Ala Ile Pro Leu Val Gly Glu Leu<br>515 520 525 | | 1584 |

-continued

```
gtt gat atc ggt ttc gct gcatacaact tcgttgaaag catcatcaac      1632
Val Asp Ile Gly Phe Ala
        530 ctgttccagg ttgttcacaa ctcttacaac cgcccggctt actctccggg tcacaagacg   1692 catgcaccta cttctagctc taccaagaaa acccagctgc agctcgagca cctgctgctg   1752 gatttgcaga tgatcctgaa cggtatcaac aattacaaga acccgaaact gacgcgtatg   1812 ctgaccttca agttctacat gccgaagaag gccaccgaac tgaaacacct gctgcagtgt   1872 ctagaagaag aactgaaacc gctggaggaa gttctgaacc tggctcagtc taaaaacttc   1932 cacctgcggc cgcgtgacct gatctctaac atcaacgtaa tcgttctgga actgaagggc   1992 tctgaaacca ccttcatgtg tgaatacgct gatgagaccg caaccatcgt agaattcctg   2052 aaccgttgga tcaccttctg tcagtctatc atctctaccc tgacc                   2097
```

<210> SEQ ID NO 31
<211> LENGTH: 534
<212> TYPE: PRT
<213> ORGANISM: Artificial sequence
<220> FEATURE:
<223> OTHER INFORMATION: Corynephage omega: DT387(V7AV29A)linkerIL2

<400> SEQUENCE: 31

```
Met Gly Ala Asp Asp Val Ala Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
```

```
                    260                 265                 270
Val Phe Ala Gly Ala Asn Tyr Ala Ala Trp Ala Val Asn Val Ala Gln
            275                 280                 285

Val Ile Asp Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Ser Ser Gly Gly Ser Ser Gly Gly Gly Gly Ser
385                 390                 395                 400

Ala Pro Thr Ser Ser Ser Thr Lys Lys Thr Gln Leu Gln Leu Glu His
                405                 410                 415

Leu Leu Leu Asp Leu Gln Met Ile Leu Asn Gly Ile Asn Asn Tyr Lys
            420                 425                 430

Asn Pro Lys Leu Thr Arg Met Leu Thr Phe Lys Phe Tyr Met Pro Lys
        435                 440                 445

Lys Ala Thr Glu Leu Lys His Leu Leu Gln Cys Leu Glu Glu Glu Leu
    450                 455                 460

Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
                485                 490                 495

Leu Lys Gly Ser Glu Thr Thr Phe Met Cys Glu Ala Gln Ser Ile Ala
            500                 505                 510

Leu Ser Ser Leu Met Val Ala Gln Ala Ile Pro Leu Val Gly Glu Leu
        515                 520                 525

Val Asp Ile Gly Phe Ala
    530

<210> SEQ ID NO 32
<211> LENGTH: 534
<212> TYPE: PRT
<213> ORGANISM: Artificial sequence
<220> FEATURE:
<223> OTHER INFORMATION: Corynephage omega: DT387(V7AV29AD291E)
      linkerIL2

<400> SEQUENCE: 32

Met Gly Ala Asp Asp Val Ala Asp Ser Ser Lys Ser Phe Val Met Glu
1               5                   10                  15

Asn Phe Ser Ser Tyr His Gly Thr Lys Pro Gly

-continued

```
                    85                  90                  95
Val Asp Asn Ala Glu Thr Ile Lys Lys Glu Leu Gly Leu Ser Leu Thr
                100                 105                 110
Glu Pro Leu Met Glu Gln Val Gly Thr Glu Glu Phe Ile Lys Arg Phe
            115                 120                 125
Gly Asp Gly Ala Ser Arg Val Leu Ser Leu Pro Phe Ala Glu Gly
        130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                165                 170                 175
Asp Ala Met Tyr Glu Tyr Met Ala Gln Ala Cys Ala Gly Asn Arg Val
            180                 185                 190
Arg Arg Ser Val Gly Ser Ser Leu Ser Cys Ile Asn Leu Asp Trp Asp
        195                 200                 205
Val Ile Arg Asp Lys Thr Lys Thr Lys Ile Glu Ser Leu Lys Glu His
            210                 215                 220
Gly Pro Ile Lys Asn Lys Met Ser Glu Ser Pro Asn Lys Thr Val Ser
225                 230                 235                 240
Glu Glu Lys Ala Lys Gln Tyr Leu Glu Glu Phe His Gln Thr Ala Leu
                245                 250                 255
Glu His Pro Glu Leu Ser Glu Leu Lys Thr Val Thr Gly Thr Asn Pro
            260                 265                 270
Val Phe Ala Gly Ala Asn Tyr Ala Ala Trp Ala Val Asn Val Ala Gln
        275                 280                 285
Val Ile Glu Ser Glu Thr Ala Asp Asn Leu Glu Lys Thr Thr Ala Ala
        290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
            340                 345                 350
Asp Ile Gly Phe Ala Ala Tyr Asn Phe Val Glu Ser Ile Ile Asn Leu
        355                 360                 365
Phe Gln Val Val His Asn Ser Tyr Asn Arg Pro Ala Tyr Ser Pro Gly
    370                 375                 380
His Lys Thr His Ala Ser Ser Gly Gly Ser Ser Gly Gly Gly Ser
385                 390                 395                 400
Ala Pro Thr Ser Ser Thr Lys Lys Thr Gln Leu Gln Leu Glu His
                405                 410                 415
Leu Leu Leu Asp Leu Gln Met Ile Leu Asn Gly Ile Asn Asn Tyr Lys
            420                 425                 430
Asn Pro Lys Leu Thr Arg Met Leu Thr Phe Lys Phe Tyr Met Pro Lys
        435                 440                 445
Lys Ala Thr Glu Leu Lys His Leu Leu Gln Cys Leu Glu Glu Glu Leu
    450                 455                 460
Lys Pro Leu Glu Glu Val Leu Asn Leu Ala Gln Ser Lys Asn Phe His
465                 470                 475                 480
Leu Arg Pro Arg Asp Leu Ile Ser Asn Ile Asn Val Ile Val Leu Glu
                485                 490                 495
Leu Lys Gly Ser Glu Thr Thr Phe Met Cys Glu Tyr Ala Asp Glu Thr
            500                 505                 510
```

Ala Thr Ile Val Glu Phe Leu Asn Arg Trp Ile Thr Phe Cys Gln Ser
        515                 520                 525

Ile Ile Ser Thr Leu Thr
    530

<210> SEQ ID NO 33
<211> LENGTH: 1602
<212> TYPE: DNA
<213> ORGANISM: Artificial sequence
<220> FEATURE:
<223> OTHER INFORMATION: Corynephage omega: DT387(D8SV29A)linkerIL2

<400> SEQUENCE: 33

| | | |
|---|---|---|
| atgggcgctg atgatgttgt tgattcttct aaatcttttg tgatggaaaa cttttcttcg | 60 |
| taccacggga ctaaacctgg ttatgtagat tccattcaaa aaggtataca aaagccaaaa | 120 |
| tctggtacac aaggaaatta tgacgatgat tggaaagggt tttatagtac cgacaataaa | 180 |
| tacgacgctg cgggatactc tgtagataat gaaaacccgc tctctggaaa agctggaggc | 240 |
| gtggtcaaag tgacgtatcc aggactgacg aaggttctcg cactaaaagt ggataatgcc | 300 |
| gaaactatta gaaagagtt aggtttaagt ctcactgaac cgttgatgga gcaagtcgga | 360 |
| acggaagagt ttatcaaaag gttcggtgat ggtgcttcgc gtgtagtgct cagccttccc | 420 |
| ttcgctgagg ggagttctag cgttgaatat attaataact gggaacaggc gaaagcgtta | 480 |
| agcgtagaac ttgagattaa ttttgaaacc cgtggaaaac gtggccaaga tgcgatgtat | 540 |
| gagtatatgg ctcaagcctg tgcaggaaat cgtgtcaggc gatcagtagg tagctcattg | 600 |
| tcatgcatca acctggattg ggatgttatc cgtgataaaa ctaaaactaa gatcgaatct | 660 |
| ctgaaagaac acggtccgat caaaaacaaa atgagcgaaa gcccgaacaa aactgtatct | 720 |
| gaagaaaaag ctaaacagta cctggaagaa ttccaccaga ctgcactgga cacccggaa | 780 |
| ctgtctgaac ttaagaccgt tactggtacc aacccggtat cgctggtgc taactacgct | 840 |
| gcttgggcag taaacgttgc tcaggttatc gatagcgaaa ctgctgataa cctgaaaaa | 900 |
| actaccgcgg ctctgtctat cctgccgggt atcggtagcg taatgggcat cgcagacggc | 960 |
| gccgttcacc acaacactga agaaatcgtt gcacagtcta cgctctgag ctctctgatg | 1020 |
| gttgctcagg ccatcccgct ggtaggtgaa ctggttgata tcggtttcgc tgcatacaac | 1080 |
| ttcgttgaaa gcatcatcaa cctgttccag gttgttcaca actcttacaa ccgcccggct | 1140 |
| tactctccgg gtcacaagac gcatgcatct agcggaggtg gctctagcgg tggaggatcc | 1200 |
| gcacctactt ctagctctac caagaaaacc cagctgcagc tcgagcacct gctgctggat | 1260 |
| ttgcagatga tcctgaacgg tatcaacaat tacaagaacc cgaaactgac gcgtatgctg | 1320 |
| accttcaagt tctacatgcc gaagaaggcc accgaactga acacctgct gcagtgtcta | 1380 |
| gaagaagaac tgaaaccgct ggaggaagtt ctgaacctgg ctcagtctaa aaacttccac | 1440 |
| ctgcggccgc gtgacctgat ctctaacatc aacgtaatcg ttctggaact gaagggctct | 1500 |
| gaaaccacct tcatgtgtga atacgctgat gagaccgcaa ccatcgtaga attcctgaac | 1560 |
| cgttggatca ccttctgtca gtctatcatc tctaccctga cc | 1602 |

<210> SEQ ID NO 34
<211> LENGTH: 534
<212> TYPE: PRT
<213> ORGANISM: Artificial sequence
<220> FEATURE:
<223> OTHER INFORMATION: Corynephage omega: DT387(D8SV29A)linkerIL2

<400> SEQUENCE: 34

```
Met Gly Ala Asp Asp Val Val Ser Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Ser Ser Gly Gly Ser Ser Gly Gly Gly Ser
385                 390                 395                 400

Ala Pro Thr Ser Ser Thr Lys Lys Thr Gln Leu Gln Leu Glu His
                405                 410                 415

Leu Leu Leu Asp Leu Gln Met Ile Leu Asn Gly Ile Asn Asn Tyr Lys
            420                 425                 430
```

```
Asn Pro Lys Leu Thr Arg Met Leu Thr Phe Lys Phe Tyr Met Pro Lys
        435                 440                 445

Lys Ala Thr Glu Leu Lys His Leu Leu Gln Cys Leu Glu Glu Glu Leu
    450                 455                 460

Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
                485                 490                 495

Leu Lys Gly Ser Glu Thr Thr Phe Met Cys Glu Tyr Ala Asp Glu Thr
            500                 505                 510

Ala Thr Ile Val Glu Phe Leu Asn Arg Trp Ile Thr Phe Cys Gln Ser
        515                 520                 525

Ile Ile Ser Thr Leu Thr
    530

<210> SEQ ID NO 35
<211> LENGTH: 1602
<212> TYPE: DNA
<213> ORGANISM: Artificial sequence
<220> FEATURE:
<223> OTHER INFORMATION: Corynephage omega:
      DAB389(V7AV29AI290A)linkerIL2

<400> SEQUENCE: 35 atg ggc gct gat gat gtt gtt gat tct tct aaa tct ttt gtg atg gaa      48 aac ttt tct tcg tac cac ggg act aaa cct ggt tat gta gat tcc att      96 caa aaa ggt ata caa aag cca aaa tct ggt aca caa gga aat tat gac     144 gat gat tgg aaa ggg ttt tat agt acc gac aat aaa tac gac gct gcg     192 gga tac tct gta gat aat gaa aac ccg ctc tct gga aaa gct gga ggc     240 gtg gtc aaa gtg acg tat cca gga ctg acg aag gtt ctc gca cta aaa     288 gtg gat aat gcc gaa act att aag aaa gag tta ggt tta agt ctc act     336 gaa ccg ttg atg gag caa gtc gga acg gaa gag ttt atc aaa agg ttc     384 ggt gat ggt gct tcg cgt gta gtg ctc agc ctt ccc ttc gct gag ggg     432 agt tct agc gtt gaa tat att aat aac tgg gaa cag gcg aaa gcg tta     480 agc gta gaa ctt gag att aat ttt gaa acc cgt gga aaa cgt ggc caa     528 gat gcg atg tat gag tat atg gct caa gcc tgt gca gga aat cgt gtc     576 agg cga tca gta ggt agc tca ttg tca tgc atc aac ctg gat tgg gat     624 gtt atc cgt gat aaa act aaa act aag atc gaa tct ctg aaa gaa cac     672 ggt ccg atc aaa aac aaa atg agc gaa agc ccg aac aaa act gta tct     720 gaa gaa aaa gct aaa cag tac ctg gaa gaa ttc cac cag act gca ctg     768 gaa cac ccg gaa ctg tct gaa ctt aag acc gtt act ggt acc aac ccg     816 gta ttc gct ggt gct aac tac gct gct tgg gca gta aac gtt gct cag     864 gtt atc gat agc gaa act gct gat aac ctg gaa aaa act acc gcg gct     912 ctg tct atc ctg ccg ggt atc ggt agc gta atg ggc atc gca gac ggc     960 gcc gtt cac cac aac act gaa gaa atc gtt gca cag tct atc gct ctg    1008 agc tct ctg atg gtt gct cag gcc atc ccg ctg gta ggt gaa ctg gtt    1056 gat atc ggt ttc gct gca tac aac ttc gtt gaa agc atc atc aac ctg    1104 ttc cag gtt gtt cac aac tct tac aac cgc ccg gct tac tct ccg ggt    1152
```

```
cac aag acg cat gca tct agc gga ggt ggc tct agc ggt gga gga tcc      1200 gca cct act tct agc tct acc aag aaa acc cag ctg cag ctc gag cac      1248 ctg ctg ctg gat ttg cag atg atc ctg aac ggt atc aac aat tac aag      1296 aac ccg aaa ctg acg cgt atg ctg acc ttc aag ttc tac atg ccg aag      1344 aag gcc acc gaa ctg aaa cac ctg ctg cag tgt cta gaa gaa gaa ctg      1392 aaa ccg ctg gag gaa gtt ctg aac ctg gct cag tct aaa aac ttc cac      1440 ctg cgg ccg cgt gac ctg atc tct aac atc aac gta atc gtt ctg gaa      1488 ctg aag ggc tct gaa acc acc ttc atg tgt gaa tac gct gat gag acc      1536 gca acc atc gta gaa ttc ctg aac cgt tgg atc acc ttc tgt cag tct      1584 atc atc tct acc ctg acc                                              1602
```

<210> SEQ ID NO 36
<211> LENGTH: 534
<212> TYPE: PRT
<213> ORGANISM: Artificial sequence
<220> FEATURE:
<223> OTHER INFORMATION: Corynephage omega:
      DAB389(V7AV29AI290A)linkerIL2

<400> S

```
Glu His Pro Glu Leu Ser Glu Leu Lys Thr Val Thr Gly Thr Asn Pro
                260                 265                 270

Val Phe Ala Gly Ala Asn Tyr Ala Ala Trp Ala Val Asn Val Ala Gln
            275                 280                 285

Val Ala Asp Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr His Ala Ser Ser Gly Gly Gly Ser Gly Gly Gly Ser
385                 390                 395                 400

Ala Pro Thr Ser Ser Ser Thr Lys Lys Thr Gln Leu Gln Leu Glu His
            405                 410                 415

Leu Leu Leu Asp Leu Gln Met Ile Leu Asn Gly Ile Asn Asn Tyr Lys
        420                 425                 430

Asn Pro Lys Leu Thr Arg Met Leu Thr Phe Lys Phe Tyr Met Pro Lys
    435                 440                 445

Lys Ala Thr Glu Leu Lys His Leu Leu Gln Cys Leu Glu Glu Glu Leu
        450                 455                 460

Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
                485                 490                 495

Leu Lys Gly Ser Glu Thr Thr Phe Met Cys Glu Tyr Ala Asp Glu Thr
            500                 505                 510

Ala Thr Ile Val Glu Phe Leu Asn Arg Trp Ile Thr Phe Cys Gln Ser
        515                 520                 525

Ile Ile Ser Thr Leu Thr
    530

<210> SEQ ID NO 37
<211> LENGTH: 1359
<212> TYPE: DNA
<213> ORGANISM: Artificial sequence
<220> FEATURE:
<223> OTHER INFORMATION: Corynephage omega: DT387(V29A)linkerEGF

<400> SEQUENCE: 37
atgggcgctg atgatgttgt tgattcttct aaatcttttg tgatggaaaa ctttcttcg      60 taccacggga ctaaacctgg ttatgtagat tccattcaaa aaggtataca aaagccaaaa    120
tctggtacac aaggaaatta tgacgatgat tggaaagggt tttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta gaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
```

```
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acggtccgat caaaaacaaa atgagcgaaa gcccgaacaa aactgtatct     720
gaagaaaaag ctaaacagta cctggaagaa ttccaccaga ctgcactgga cacccggaa      780 ctgtctgaac ttaagaccgt tactggtacc aacccggtat cgctggtgc taactacgct       840 gcttgggcag taaacgttgc tcaggttatc gatagcgaaa ctgctgatac cctggaaaaa      900
actaccgcgg ctctgtctat cctgccgggt atcggtagcg taatgggcat cgcagacggc      960
gccgttcacc acaacactga agaaatcgtt gcacagtcta tcgctctgag ctctctgatg     1020
gttgctcagg ccatcccgct ggtaggtgaa ctggttgata tcggtttcgc tgcatacaac     1080
ttcgttgaaa gcatcatcaa cctgttccag gttgttcaca actcttacaa ccgcccggct     1140
tactctccgg gtcacaagac gcatgcatct agcggaggtg gctctagcgg tggaggatcc     1200
aacagcgata gcgaatgccc gctgagccat gatggctatt gcctgcatga tggcgtgtgc     1260
atgtatattg aagcgctgga taaatatgcg tgcaactgcg tggtgggcta tattggcgaa     1320
cgctgccagt atcgcgatct gaaatggtgg gaactgcgc                             1359
```

<210> SEQ ID NO 38
<211> LENGTH: 453
<212> TYPE: PRT
<213> ORGANISM: Artificial sequence
<220> FEATURE:
<223> OTHER INFORMATION: Corynephage omega: DT387(V29A)linkerEGF

<400> SEQUENCE: 38

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val

```
            210                 215                 220
Gly Pro Ile Lys Asn Lys Met Ser Glu Ser Pro Asn Lys Thr Val Ser
225                 230                 235                 240

Glu Glu Lys Ala Lys Gln Tyr Leu Glu Phe His Gln Thr Ala Leu
                245                 250                 255

Glu His Pro Glu Leu Ser Glu Leu Lys Thr Val Thr Gly Thr Asn Pro
                260                 265                 270

Val Phe Ala Gly Ala Asn Tyr Ala Ala Trp Ala Val Asn Val Ala Gln
                275                 280                 285

Val Ile Asp Ser Glu Thr Ala Asp Thr Leu Glu Lys Thr Thr Ala Ala
            290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
            370                 375                 380

His Lys Thr His Ala Ser Gly Gly Gly Ser Gly Gly Gly Ser
385                 390                 395                 400

Asn Ser Asp Ser Glu Cys Pro Leu Ser His Asp Gly Tyr Cys Leu His
                405                 410                 415

Asp Gly Val Cys Met Tyr Ile Glu Ala Leu Asp Lys Tyr Ala Cys Asn
                420                 425                 430

Cys Val Val Gly Tyr Ile Gly Glu Arg Cys Gln Tyr Arg Asp Leu Lys
            435                 440                 445

Trp Trp Glu Leu Arg
    450

<210> SEQ ID NO 39
<211> LENGTH: 1359
<212> TYPE: DNA
<213> ORGANISM: Artificial sequence
<220> FEATURE:
<223> OTHER INFORMATION: Corynephage omega: DT387(D291E)linkerEGF

<400> SEQUENCE: 39
atgggcgctg atgatgttgt tgattcttct aaatcttttg tgatggaaaa cttttcttcg     60
taccacggga ctaaacctgg ttatgtagat tccattcaaa aaggtataca aaagccaaaa    120
tctggtacac aaggaaatta tgacgatgat tggaaagggt tttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta gaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgcaggaaat cgtgtcaggc gatcagtagg tagctcattg    600
tcatgcatca acctggattg ggatgttatc cgtgataaaa ctaaaactaa gatcgaatct    660
ctgaaagaac acggtccgat caaaaacaaa atgagcgaaa gcccgaacaa aactgtatct    720
```

```
gaagaaaaag ctaaacagta cctggaagaa ttccaccaga ctgcactgga acacccggaa      780
ctgtctgaac ttaagaccgt tactggtacc aacccggtat tcgctggtgc taactacgct      840
gcttgggcag taaacgttgc tcaggttatc gatagcgaaa ctgctgataa cctggaaaaa      900
actaccgcgg ctctgtctat cctgccgggt atcggtagcg taatgggcat cgcagacggc      960
gccgttcacc acaacactga agaaatcgtt gcacagtcta tcgctctgag ctctctgatg     1020
gttgctcagg ccatcccgct ggtaggtgaa ctggttgata tcggtttcgc tgcatacaac     1080
ttcgttgaaa gcatcatcaa cctgttccag gttgttcaca actcttacaa ccgcccggct     1140
tactctccgg gtcacaagac gcatgcatct agcggaggtg gctctagcgg tggaggatcc     1200
aacagcgata cgaatgcccc gctgagccat gatggctatt gcctgcatga tggcgtgtgc     1260
atgtatattg aagcgctgga taaatatgcg tgcaactgcg tggtgggcta tattggcgaa     1320
cgctgccagt atcgcgatct gaaatggtgg gaactgcgc                            1359
```

<210> SEQ ID NO 40
<211> LENGTH: 453
<212> TYPE: PRT
<213> ORGANISM: Artificial sequence
<220> FEATURE:
<223> OTHER INFORMATION: Corynephage omega: DT387(V291E)linkerEGF

<400> SEQUENCE: 40

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255
```

```
Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
            275                 280                 285

Val Ile Glu Ser Glu Thr Ala Asp Asn Leu Glu Lys Thr Thr Ala Ala
            290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
            325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
370                 375                 380

His Lys Thr His Ala Ser Ser Gly Gly Ser Ser Gly Gly Ser
385                 390                 395                 400

Asn Ser Asp Ser Glu Cys Pro Leu Ser His Asp Gly Tyr Cys Leu His
            405                 410                 415

Asp Gly Val Cys Met Tyr Ile Glu Ala Leu Asp Lys Tyr Ala Cys Asn
            420                 425                 430

Cys Val Val Gly Tyr Ile Gly Glu Arg Cys Gln Tyr Arg Asp Leu Lys
            435                 440                 445

Trp Trp Glu Leu Arg
450

<210> SEQ ID NO 41
<211> LENGTH: 1359
<212> TYPE: DNA
<213> ORGANISM: Artificial sequence
<220> FEATURE:
<223> OTHER INFORMATION: Corynephage omega: DT387(D8EV29A)linkerEGF

<400> SEQUENCE: 41 atg ggc gct gat gat gtt gtt gat tct tct aaa tct ttt gtg atg gaa        48 aac ttt tct tcg tac cac ggg act aaa cct ggt tat gta gat tcc att        96 caa aaa ggt ata caa aag cca aaa tct ggt aca caa gga aat tat gac       144 gat gat tgg aaa ggg ttt tat agt acc gac aat aaa tac gac gct gcg       192 gga tac tct gta gat aat gaa aac ccg ctc tct gga aaa gct gga ggc       240 gtg gtc aaa gtg acg tat cca gga ctg acg aag gtt ctc gca cta aaa       288 gtg gat aat gcc gaa act att aag aaa gag tta ggt tta agt ctc act       336 gaa ccg ttg atg gag caa gtc gga acg gaa gag ttt atc aaa agg ttc       384 ggt gat ggt gct tcg cgt gta gtg ctc agc ctt ccc ttc gct gag ggg       432 agt tct agc gtt gaa tat att aat aac tgg gaa cag gcg aaa gcg tta       480 agc gta gaa ctt gag att aat ttt gaa acc cgt gga aaa cgt ggc caa       528 gat gcg atg tat gag tat atg gct caa gcc tgt gca gga aat cgt gtc       576 agg cga tca gta ggt agc tca ttg tca tgc atc aac ctg gat tgg gat       624 gtt atc cgt gat aaa act aaa act aag atc gaa tct ctg aaa gaa cac       672 ggt ccg atc aaa aac aaa atg agc gaa agc ccg aac aaa act gta tct       720
```

```
gaa gaa aaa gct aaa cag tac ctg gaa gaa ttc cac cag act gca ctg    768
gaa cac ccg gaa ctg tct gaa ctt aag acc gtt act ggt acc aac ccg    816
gta ttc gct ggt gct aac tac gct gct tgg gca gta aac gtt gct cag    864
gtt atc gat agc gaa act gct gat aac ctg gaa aaa act acc gcg gct    912
ctg tct atc ctg ccg ggt atc ggt agc gta atg ggc atc gca gac ggc    960
gcc gtt cac cac aac act gaa gaa atc gtt gca cag tct atc gct ctg    1008
agc tct ctg atg gtt gct cag gcc atc ccg ctg gta ggt gaa ctg gtt    1056
gat atc ggt ttc gct gca tac aac ttc gtt gaa agc atc atc aac ctg    1104
ttc cag gtt gtt cac aac tct tac aac cgc ccg gct tac tct ccg ggt    1152
cac aag acg cat gca tct agc gga ggt ggc tct agc ggt gga gga tcc    1200
aac agc gat agc gaa tgc ccg ctg agc cat gat ggc tat tgc ctg cat    1248
gat ggc gtg tgc atg tat att gaa gcg ctg gat aaa tat gcg tgc aac    1296
tgc gtg gtg ggc tat att ggc gaa cgc tgc cag tat cgc gat ctg aaa    1344
tgg tgg gaa ctg cgc                                                1359
```

<210> SEQ ID NO 42
<211> LENGTH: 453
<212> TYPE: PRT
<213> ORGANISM: Artificial sequence
<220> FEATURE:
<223> OTHER INFORMATION: Corynephage omega: DT387(D8EV29A)linkerEGF

<400> SEQUENCE: 42

```
Met Gly Ala Asp Asp Val Val Glu Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220
```

```
Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
            245                 250                 255

Glu His Pro Glu Leu Ser Glu Leu Lys Thr Val Thr Gly Thr Asn Pro
        260                 265                 270

Val Phe Ala Gly Ala Asn Tyr Ala Ala Trp Ala Val Asn Val Ala Gln
    275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Ser Ser Gly Gly Ser Ser Gly Gly Gly Ser
385                 390                 395                 400

Asn Ser Asp Ser Glu Cys Pro Leu Ser His Asp Gly Tyr Cys Leu His
                405                 410                 415

Asp Gly Val Cys Met Tyr Ile Glu Ala Leu Asp Lys Tyr Ala Cys Asn
            420                 425                 430

Cys Val Val Gly Tyr Ile Gly Glu Arg Cys Gln Tyr Arg Asp Leu Lys
        435                 440                 445

Trp Trp Glu Leu Arg
    450

<210> SEQ ID NO 43
<211> LENGTH: 1359
<212> TYPE: DNA
<213> ORGANISM: Artificial sequence
<220> FEATURE:
<223> OTHER INFORMATION: Corynephage omega: DT387(V7SV29A)linkerEGF

<400> SEQUENCE: 43
atgggcgctg atgatgttgt tgattcttct aaatcttttg tgatggaaaa ctttttcttcg      60 taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acgtccgat caaaaacaaa atgagcgaaa gcccgaacaa aactgtatct     720
gaagaaaaag ctaaacagta cctggaagaa ttccaccaga ctgcactgga cacccggaa     780
```

```
ctgtctgaac ttaagaccgt tactggtacc aacccggtat tcgctggtgc taactacgct    840
gcttgggcag taaacgttgc tcaggttatc gatagcgaaa ctgctgataa cctggaaaaa    900
actaccgcgg ctctgtctat cctgccgggt atcggtagcg taatgggcat cgcagacggc    960
gccgttcacc acaacactga agaaatcgtt gcacagtcta tcgctctgag ctctctgatg   1020
gttgctcagg ccatcccgct ggtaggtgaa ctggttgata tcggtttcgc tgcatacaac   1080
ttcgttgaaa gcatcatcaa cctgttccag gttgttcaca actcttacaa ccgcccggct   1140
tactctccgg gtcacaagac gcatgcatct agcggaggtg gctctagcgg tggaggatcc   1200
aacagcgata gcgaatgccc gctgagccat gatggctatt gcctgcatga tggcgtgtgc   1260
atgtatattg aagcgctgga taaatatgct tgcaactgcg tggtgggcta tattggcgaa   1320
cgctgccagt atcgcgatct gaaatggtgg gaactgcgc                          1359
```

<210> SEQ ID NO 44
<211> LENGTH: 453
<212> TYPE: PRT
<213> ORGANISM: Artificial sequence
<220> FEATURE:
<223> OTHER INFORMATION: Corynephage omega: DT387(V7SV29A)linkerEGF

<400> SEQUENCE: 44

```
Met Gly Ala Asp Asp Val Ser Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
```

```
              260                 265                 270
Val Phe Ala Gly Ala Asn Tyr Ala Ala Trp Ala Val Asn Val Ala Gln
            275                 280                 285

Val Ile Asp Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Ser Ser Gly Gly Ser Ser Gly Gly Gly Ser
385                 390                 395                 400

Asn Ser Asp Ser Glu Cys Pro Leu Ser His Asp Gly Tyr Cys Leu His
                405                 410                 415

Asp Gly Val Cys Met Tyr Ile Glu Ala Leu Asp Lys Tyr Ala Cys Asn
                420                 425                 430

Cys Val Val Gly Tyr Ile Gly Glu Arg Cys Gln Tyr Arg Asp Leu Lys
            435                 440                 445

Trp Trp Glu Leu Arg
    450

<210> SEQ ID NO 45
<211> LENGTH: 1359
<212> TYPE: DNA
<213> ORGANISM: Artificial sequence
<220> FEATURE:
<223> OTHER INFORMATION: Corynephage omega: DT387(V7AV29A)linkerEGF

<400> SEQUENCE: 45
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaggagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acggtccgat caaaaacaaa atgagcgaaa gcccgaacaa actgtatctc     720
gaagaaaaag ctaaacagta cctggaagaa ttccaccaga ctgcactgga caccccggaa     780
ctgtctgaac ttaagaccgt tactggtacc aacccggtat cgctggtgc taactacgct     840 gcttgggcag taacgttgc tcaggttatc gatagcgaaa ctgctgataa cctggaaaaa     900
actaccgcgg ctctgtctat cctgccgggt atcggtagcg taatgggcat cgcagacggc     960
```

```
gccgttcacc acaacactga agaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggct    1140
tactctccgg tcacaagac gcatgcatct agcggaggtg gctctagcgg tggaggatcc     1200
aacagcgata gcgaatgccc gctgagccat gatggctatt gcctgcatga tggcgtgtgc    1260
atgtatattg aagcgctgga taaatatgcg tgcaactgcg tggtgggcta tattggcgaa    1320
cgctgccagt atcgcgatct gaaatggtgg gaactgcgc                           1359
```

<210> SEQ ID NO 46
<211> LENGTH: 453
<212> TYPE: PRT
<213> ORGANISM: Artificial sequence
<220> FEATURE:
<223> OTHER INFORMATION: Corynephage omega: DT387(V7AV29A)linkerEGF

<400> SEQUENCE: 46

```
Met Gly Ala Asp Asp Val Ala Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Ala Ala
    290                 295                 300
```

```
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
            340                 345                 350
Asp Ile Gly Phe Ala Ala Tyr Asn Phe Val Glu Ser Ile Ile Asn Leu
        355                 360                 365
Phe Gln Val Val His Asn Ser Tyr Asn Arg Pro Ala Tyr Ser Pro Gly
    370                 375                 380
His Lys Thr His Ala Ser Ser Gly Gly Ser Ser Gly Gly Gly Gly Ser
385                 390                 395                 400
Asn Ser Asp Ser Glu Cys Pro Leu Ser His Asp Gly Tyr Cys Leu His
                405                 410                 415
Asp Gly Val Cys Met Tyr Ile Glu Ala Leu Asp Lys Tyr Ala Cys Asn
            420                 425                 430
Cys Val Val Gly Tyr Ile Gly Glu Arg Cys Gln Tyr Arg Asp Leu Lys
        435                 440                 445
Trp Trp Glu Leu Arg
    450

<210> SEQ ID NO 47
<211> LENGTH: 1359
<212> TYPE: DNA
<213> ORGANISM: Artificial sequence
<220> FEATURE:
<223> OTHER INFORMATION: Corynephage omega: DT387(D8EV29AD291E)linkerEGF

<400> SEQUENCE: 47
atgggcgctg atgatgttgt tgattcttct aaatcttttg tgatggaaaa ctttttcttcg      60 taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acggtccgat caaaaacaaa atgagcgaaa gcccgaacaa aactgtatct     720
gaagaaaaag ctaaacagta cctggaagaa ttccaccaga ctgcactgga cacccggaa     780 ctgtctgaac ttaagaccgt tactggtacc accccggtat cgctggtgc taactacgct     840 gcttgggcag taacgttgc tcaggttatc gatagcgaaa ctgctgataa cctggaaaaa     900
actaccgcgg ctctgtctat cctgccgggt atcggtagcg taatgggcat cgcagacggc     960
gccgttcacc acaacactga gaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggct    1140
tactctccgg gtcacaagac gcatgcatct agcggaggtg gctctagcgg tggaggatcc    1200
```

-continued

```
aacagcgata cgcaatgccc gctgagccat gatggctatt gcctgcatga tggcgtgtgc    1260
atgtatattg aagcgctgga taaatatgcg tgcaactgcg tggtgggcta tattggcgaa    1320
cgctgccagt atcgcgatct gaaatggtgg gaactgcgc                           1359
```

<210> SEQ ID NO 48
<211> LENGTH: 453
<212> TYPE: PRT
<213> ORGANISM: Artificial sequence
<220> FEATURE:
<223> OTHER INFORMATION: Corynephage omega: DT387(D8EV29AD291E)linkerEGF

<400> SEQUENCE: 48

```
Met Gly Ala Asp Asp Val Val Glu Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Thr Pro
            260                 265                 270

Val Phe Ala Gly Ala Asn Tyr Ala Ala Trp Ala Val Asn Val Ala Gln
        275                 280                 285

Val Ile Glu Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335
```

```
Ser Ser Leu Met Val Ala Gln Ala Ile Pro Leu Val Gly Glu Leu Val
            340                 345                 350
Asp Ile Gly Phe Ala Ala Tyr Asn Phe Val Glu Ser Ile Ile Asn Leu
            355                 360                 365
Phe Gln Val Val His Asn Ser Tyr Asn Arg Pro Ala Tyr Ser Pro Gly
370                 375                 380
His Lys Thr His Ala Ser Ser Gly Gly Ser Ser Gly Gly Ser
385                 390                 395                 400
Asn Ser Asp Ser Glu Cys Pro Leu Ser His Asp Gly Tyr Cys Leu His
                405                 410                 415
Asp Gly Val Cys Met Tyr Ile Glu Ala Leu Asp Lys Tyr Ala Cys Asn
            420                 425                 430
Cys Val Val Gly Tyr Ile Gly Glu Arg Cys Gln Tyr Arg Asp Leu Lys
            435                 440                 445
Trp Trp Glu Leu Arg
            450

<210> SEQ ID NO 49
<211> LENGTH: 1359
<212> TYPE: DNA
<213> ORGANISM: Artificial sequence
<220> FEATURE:
<223> OTHER INFORMATION: Corynephage omega: DT387(D8SV29A)linkerEGF

<400> SEQUENCE: 49
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acgtccgat caaaaacaaa atgagcgaaa gcccgaacaa aactgtatct     720 gaagaaaag ctaaacagta cctggaagaa ttccaccaga ctgcactgga cacccggaa     780 ctgtctgaac ttaagaccgt tactggtacc aacccggtat cgctggtgc taactacgct     840 gcttgggcag taaacgttgc tcaggttatc gatagcgaaa ctgctgataa cctggaaaaa     900
actaccgcgg ctctgtctat cctgccgggt atcggtagcg taatgggcat cgcagacggc     960
gccgttcacc acaacactga gaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggct    1140
tactctccgg gtcacaagac gcatgcatct agcggaggtg gctctagcgg tggaggatcc    1200
aacagcgata gcgaatgccc gctgagccat gatggctatt gcctgcatga tggcgtgtgc    1260
atgtatattg aagcgctgga taaatatgcg tgcaactgcg tggtgggcta tattggcgaa    1320
cgctgccagt atcgcgatct gaaatggtgg gaactgcgc                           1359
```

<210> SEQ ID NO 50
<211> LENGTH: 453
<212> TYPE: PRT
<213> ORGANISM: Artificial sequence
<220> FEATURE:
<223> OTHER INFORMATION: Corynephage omega: DT387(D8SV29A)linkerEGF

<400> SEQUENCE: 50

```
Met Gly Ala Asp Asp Val Val Ser Ser Lys Ser Phe Val Met Glu
1               5                   10                  15

Asn Phe Ser Ser Tyr His Gly Thr Lys Pro Gly Tyr Ala Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
```

-continued

```
                 370                 375                 380
His Lys Thr His Ala Ser Ser Gly Gly Ser Ser Gly Gly Ser
385                 390                 395                 400

Asn Ser Asp Ser Glu Cys Pro Leu Ser His Asp Gly Tyr Cys Leu His
                405                 410                 415

Asp Gly Val Cys Met Tyr Ile Glu Ala Leu Asp Lys Tyr Ala Cys Asn
                420                 425                 430

Cys Val Val Gly Tyr Ile Gly Glu Arg Cys Gln Tyr Arg Asp Leu Lys
                435                 440                 445

Trp Trp Glu Leu Arg
        450

<210> SEQ ID NO 51
<211> LENGTH: 1179
<212> TYPE: DNA
<213> ORGANISM: Artificial sequence
<220> FEATURE:
<223> OTHER INFORMATION: Corynephage omega: DT387(V7A)

<400> SEQUENCE: 51
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acggtccgat caaaaacaaa atgagcgaaa gcccgaacaa actgtatctc     720 gaagaaaag ctaaacagta cctggaagaa ttccaccaga ctgcactgga acacccggaa     780
ctgtctgaac ttaagaccgt tactggtacc aacccggtat cgctggtgc taactacgct     840 gcttgggcag taaacgttgc tcaggttatc gatagcgaaa ctgctgataa cctggaaaaa     900
actaccgcgg ctctgtctat cctgccgggt atcggtagcg taatgggcat cgcagacggc     960
gccgttcacc acaacactga agaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggcg    1140
catgcatcta gcggaggtgg ctctagcggt ggaggctgt                           1179

<210> SEQ ID NO 52
<211> LENGTH: 393
<212> TYPE: PRT
<213> ORGANISM: Artificial sequence
<220> FEATURE:
<223> OTHER INFORMATION: Corynephage omega: DT387(V7A)

<400> SEQUENCE: 52

Met Gly Ala Asp Asp Val Ala Asp Ser Ser Lys Ser Phe Val Met Glu
1               5                   10                  15
```

| | | | | | | | | | | | | |
|---|---|---|---|---|---|---|---|---|---|---|---|---|
|Asn|Phe|Ser|Ser|Tyr|His|Gly|Thr|Lys|Pro|Gly|Tyr|Val|Asp|Ser|Ile|
| | | |20| | | |25| | | |30| | | | |

Gln Lys Gly Ile Gln Lys Pro Lys Ser Gly Thr Gln Gly Asn Tyr Asp
            35              40              45

Asp Asp Trp Lys Gly Phe Tyr Ser Thr Asp Asn Lys Tyr Asp Ala Ala
    50              55              60

Gly Tyr Ser Val Asp Asn Glu Asn Pro Leu Ser Gly Lys Ala Gly Gly
65              70              75              80

Val Val Lys Val Thr Tyr Pro Gly Leu Thr Lys Val Leu Ala Leu Lys
                85              90              95

Val Asp Asn Ala Glu Thr Ile Lys Lys Glu Leu Gly Leu Ser Leu Thr
            100             105             110

Glu Pro Leu Met Glu Gln Val Gly Thr Glu Glu Phe Ile Lys Arg Phe
        115             120             125

Gly Asp Gly Ala Ser Arg Val Val Leu Ser Leu Pro Phe Ala Glu Gly
    130             135             140

Ser Ser Ser Val Glu Tyr Ile Asn Asn Trp Glu Gln Ala Lys Ala Leu
145             150             155             160

Ser Val Glu Leu Glu Ile Asn Phe Glu Thr Arg Gly Lys Arg Gly Gln
                165             170             175

Asp Ala Met Tyr Glu Tyr Met Ala Gln Ala Cys Ala Gly Asn Arg Val
            180             185             190

Arg Arg Ser Val Gly Ser Ser Leu Ser Cys Ile Asn Leu Asp Trp Asp
        195             200             205

Val Ile Arg Asp Lys Thr Lys Thr Lys Ile Glu Ser Leu Lys Glu His
    210             215             220

Gly Pro Ile Lys Asn Lys Met Ser Glu Ser Pro Asn Lys Thr Val Ser
225             230             235             240

Glu Glu Lys Ala Lys Gln Tyr Leu Glu Glu Phe His Gln Thr Ala Leu
                245             250             255

Glu His Pro Glu Leu Ser Glu Leu Lys Thr Val Thr Gly Thr Asn Pro
            260             265             270

Val Phe Ala Gly Ala Asn Tyr Ala Ala Trp Ala Val Asn Val Ala Gln
        275             280             285

Val Ile Asp Ser Glu Thr Ala Asp Asn Leu Glu Lys Thr Thr Ala Ala
    290             295             300

Leu Ser Ile Leu Pro Gly Ile Gly Ser Val Met Gly Ile Ala Asp Gly
305             310             315             320

Ala Val His His Asn Thr Glu Glu Ile Val Ala Gln Ser Ile Ala Leu
                325             330             335

Ser Ser Leu Met Val Ala Gln Ala Ile Pro Leu Val Gly Glu Leu Val
            340             345             350

Asp Ile Gly Phe Ala Ala Tyr Asn Phe Val Glu Ser Ile Ile Asn Leu
        355             360             365

Phe Gln Val Val His Asn Ser Tyr Asn Arg Pro Ala His Ala Ser Ser
    370             375             380

Gly Gly Gly Ser Ser Gly Gly Gly Cys
385             390

<210> SEQ ID NO 53
<211> LENGTH: 1179
<212> TYPE: DNA
<213> ORGANISM: Artificial sequence
<220> FEATURE:
<223> OTHER INFORMATION: Corynephage omega: DT387(D8S)

<400> SEQUENCE: 53

```
atgggcgctg atgatgttgt tgattcttct aaatcttttg tgatggaaaa ctttcttcg      60
taccacggga ctaaacctgg ttatgtagat tccattcaaa aaggtataca aaagccaaaa    120
tctggtacac aaggaaatta tgacgatgat tggaaagggt tttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta gaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga ggcgatgtat    540
gagtatatgg ctcaagcctg tgcaggaaat cgtgtcaggc gatcagtagg tagctcattg    600
tcatgcatca acctggattg ggatgttatc cgtgataaaa ctaaaactaa gatcgaatct    660
ctgaaagaac acggtccgat caaaaacaaa atgagcgaaa gcccgaacaa aactgtatct    720
gaagaaaaag ctaaacagta cctggaagaa ttccaccaga ctgcactgga cacccggaa     780
ctgtctgaac ttaagaccgt tactggtacc aacccggtat cgctggtgc taactacgct    840
gcttgggcag taaacgttgc tcaggttatc gatagcgaaa ctgctgataa cctggaaaaa    900
actaccgcgg ctctgtctat cctgccgggt atcggtagcg taatgggcat cgcagacggc    960
gccgttcacc acaacactga agaaatcgtt gcacagtcta tcgctctgag ctctctgatg   1020
gttgctcagg ccatcccgct ggtaggtgaa ctggttgata tcggtttcgc tgcatacaac   1080
ttcgttgaaa gcatcatcaa cctgttccag gttgttcaca actcttacaa ccgcccggcg   1140
catgcatcta gcggaggtgg ctctagcggt ggaggctgt                          1179
```

<210> SEQ ID NO 54
<211> LENGTH: 393
<212> TYPE: PRT
<213> ORGANISM: Artificial sequence
<220> FEATURE:
<223> OTHER INFORMATION: Corynephage omega: DT387(D8S)

<400> SEQUENCE: 54

```
Met Gly Ala Asp Asp Val Val Ser Ser Lys Ser Phe Val Met Glu
1               5                   10                  15

Asn Phe Ser Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
```

|   |   |   |   |   |   |   |   |   |   |   |   |
|---|---|---|---|---|---|---|---|---|---|---|---|
| 145 | | | | 150 | | | | 155 | | | 160 |
| Ser | Val | Glu | Leu | Glu | Ile | Asn | Phe | Glu | Thr | Arg | Gly | Lys | Arg | Gly | Gln |
| | | | | 165 | | | | | 170 | | | | | 175 | |
| Glu | Ala | Met | Tyr | Glu | Tyr | Met | Ala | Gln | Ala | Cys | Ala | Gly | Asn | Arg | Val |
| | | | | 180 | | | | | 185 | | | | | 190 | |
| Arg | Arg | Ser | Val | Gly | Ser | Ser | Leu | Ser | Cys | Ile | Asn | Leu | Asp | Trp | Asp |
| | | | 195 | | | | | 200 | | | | | 205 | | |
| Val | Ile | Arg | Asp | Lys | Thr | Lys | Thr | Lys | Ile | Glu | Ser | Leu | Lys | Glu | His |
| | | | 210 | | | | | 215 | | | | | 220 | | |
| Gly | Pro | Ile | Lys | Asn | Lys | Met | Ser | Glu | Ser | Pro | Asn | Lys | Thr | Val | Ser |
| 225 | | | | | 230 | | | | | 235 | | | | | 240 |
| Glu | Glu | Lys | Ala | Lys | Gln | Tyr | Leu | Glu | Glu | Phe | His | Gln | Thr | Ala | Leu |
| | | | | 245 | | | | | 250 | | | | | 255 | |
| Glu | His | Pro | Glu | Leu | Ser | Glu | Leu | Lys | Thr | Val | Thr | Gly | Thr | Asn | Pro |
| | | | | 260 | | | | | 265 | | | | | 270 | |
| Val | Phe | Ala | Gly | Ala | Asn | Tyr | Ala | Ala | Trp | Ala | Val | Asn | Val | Ala | Gln |
| | | | 275 | | | | | 280 | | | | | 285 | | |
| Val | Ile | Asp | Ser | Glu | Thr | Ala | Asp | Asn | Leu | Glu | Lys | Thr | Thr | Ala | Ala |
| | | | 290 | | | | | 295 | | | | | 300 | | |
| Leu | Ser | Ile | Leu | Pro | Gly | Ile | Gly | Ser | Val | Met | Gly | Ile | Ala | Asp | Gly |
| 305 | | | | | 310 | | | | | 315 | | | | | 320 |
| Ala | Val | His | His | Asn | Thr | Glu | Glu | Ile | Val | Ala | Gln | Ser | Ile | Ala | Leu |
| | | | | 325 | | | | | 330 | | | | | 335 | |
| Ser | Ser | Leu | Met | Val | Ala | Gln | Ala | Ile | Pro | Leu | Val | Gly | Glu | Leu | Val |
| | | | | 340 | | | | | 345 | | | | | 350 | |
| Asp | Ile | Gly | Phe | Ala | Ala | Tyr | Asn | Phe | Val | Glu | Ser | Ile | Ile | Asn | Leu |
| | | | 355 | | | | | 360 | | | | | 365 | | |
| Phe | Gln | Val | Val | His | Asn | Ser | Tyr | Asn | Arg | Pro | Ala | His | Ala | Ser | Ser |
| | | | 370 | | | | | 375 | | | | | 380 | | |
| Gly | Gly | Gly | Ser | Ser | Gly | Gly | Gly | Cys | | | | | | | |
| 385 | | | | | 390 | | | | | | | | | | |

<210> SEQ ID NO 55
<211> LENGTH: 1179
<212> TYPE: DNA
<213> ORGANISM: Artificial sequence
<220> FEATURE:
<223> OTHER INFORMATION: Corynephage omega: DT387(V7S)

<400> SEQUENCE: 55

| | | |
|---|---|---|
| atgggcgctg atgatgttgt tgattcttct aaatcttttg tgatggaaaa cttttcttcg | 60 |
| taccacggga ctaaacctgg ttatgtagat tccattcaaa aaggtataca aaagccaaaa | 120 |
| tctggtacac aaggaaatta tgacgatgat tggaaagggt ttatagtac cgacaataaa | 180 |
| tacgacgctg cgggatactc tgtagataat gaaaacccgc tctctggaaa agctggaggc | 240 |
| gtggtcaaag tgacgtatcc aggactgacg aaggttctcg cactaaaagt ggataatgcc | 300 |
| gaaactatta gaaagagtt aggtttaagt ctcactgaac cgttgatgga gcaagtcgga | 360 |
| acggaagagt ttatcaaaag gttcggtgat ggtgcttcgc gtgtagtgct cagccttccc | 420 |
| ttcgctgagg ggagttctag cgttgaatat attaataact gggaacaggc gaaagcgtta | 480 |
| agcgtagaac ttgagattaa ttttgaaacc cgtgaaaac gtggccaaga tgcgatgtat | 540 |
| gagtatatgg ctcaagcctg tgcaggaaat cgtgtcaggc gatcagtagg tagctcattg | 600 |
| tcatgcatca acctggattg ggatgttatc cgtgataaaa ctaaaactaa gatcgaatct | 660 |
| ctgaaagaac acggtccgat caaaaacaaa atgagcgaaa gcccgaacaa aactgtatct | 720 |

```
gaagaaaaag ctaaacagta cctggaagaa ttccaccaga ctgcactgga acacccggaa    780
ctgtctgaac ttaagaccgt tactggtacc aacccggtat cgctggtgc taactacgct    840 gcttgggcag taacgttgc tcaggttatc gatagcgaaa ctgctgataa cctggaaaaa    900
actaccgcgg ctctgtctat cctgccgggt atcggtagcg taatgggcat cgcagacggc    960
gccgttcacc acaacactga agaaatcgtt gcacagtcta cgctctgag ctctctgatg   1020 gttgctcagg ccatcccgct ggtaggtgaa ctggttgata tcggtttcgc tgcatacaac   1080
ttcgttgaaa gcatcatcaa cctgttccag gttgttcaca actcttacaa ccgcccggcg   1140
catgcatcta gcggaggtgg ctctagcggt ggaggctgt                          1179
```

<210> SEQ ID NO 56
<211> LENGTH: 393
<212> TYPE: PRT
<213> ORGANISM: Artificial sequence
<220> FEATURE:
<223> OTHER INFORMATION: Corynephage omega: DT387(V7S)

<400> SEQUENCE: 56

```
Met Gly Ala Asp Asp Val Ser Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285
```

```
Val Ile Asp Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala His Ala Ser Ser
    370                 375                 380

Gly Gly Gly Ser Ser Gly Gly Gly Cys
385                 390
```

<210> SEQ ID NO 57
<211> LENGTH: 1179
<212> TYPE: DNA
<213> ORGANISM: Artificial sequence
<220> FEATURE:
<223> OTHER INFORMATION: Corynephage omega: DT387(D8E)

<400> SEQUENCE: 57

```
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta agaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acggtccgat caaaaacaaa atgagcgaaa gcccgaacaa aactgtatct     720
gaagaaaaag ctaaacagta cctggaagaa ttccaccaga ctgcactgga cacccggaa      780
ctgtctgaac ttaagaccgt tactggtacc aacccggtat cgctggtgc taactacgct      840
gcttgggcag taaacgttgc tcaggttatc gatagcgaaa ctgctgataa cctggaaaaa     900
actaccgcgg ctctgtctat cctgccgggt atcggtagcg taatgggcat cgcagacggc     960
gccgttcacc acaacactga agaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggcg    1140
catgcatcta gcggaggtgg ctctagcggt ggaggctgt                           1179
```

<210> SEQ ID NO 58
<211> LENGTH: 393
<212> TYPE: PRT
<213> ORGANISM: Artificial sequence
<220> FEATURE:
<223> OTHER INFORMATION: Corynephage omega: DT387(D8E)

<400> SEQUENCE: 58

```
Met Gly Ala Asp Asp Val Val Glu Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
130                 135                 140

Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala His Ala Ser Ser
370                 375                 380

Gly Gly Gly Ser Ser Gly Gly Gly Cys
385                 390
```

<210> SEQ ID NO 59
<211> LENGTH: 1179

```
<212> TYPE: DNA
<213> ORGANISM: Artificial sequence
<220> FEATURE:
<223> OTHER INFORMATION: Corynephage omega: DT387(V29A)

<400> SEQUENCE: 59
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta agaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acggtccgat caaaaacaaa atgagcgaaa gcccgaacaa aactgtatct     720
gaagaaaaag ctaaacagta cctggaagaa ttccaccaga ctgcactgga caccccggaa     780
ctgtctgaac ttaagaccgt tactggtacc aacccggtat cgctggtgc taactacgct      840
gcttgggcag taaacgttgc tcaggttatc gatagcgaaa ctgctgataa cctggaaaaa     900
actaccgcgg ctctgtctat cctgccgggt atcggtagcg taatgggcat cgcagacggc     960
gccgttcacc acaacactga agaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggcg    1140
catgcatcta gcggaggtgg ctctagcggt ggaggctgt                           1179

<210> SEQ ID NO 60
<211> LENGTH: 393
<212> TYPE: PRT
<213> ORGANISM: Artificial sequence
<220> FEATURE:
<223> OTHER INFORMATION: Corynephage omega: DT387(V29A)

<400> SEQUENCE: 60

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125
```

```
Gly Asp Gly Ala Ser Arg Val Val Leu Ser Leu Pro Phe Ala Glu Gly
            130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala His Ala Ser Ser
370                 375                 380

Gly Gly Gly Ser Ser Gly Gly Gly Cys
385                 390

<210> SEQ ID NO 61
<211> LENGTH: 1179
<212> TYPE: DNA
<213> ORGANISM: Artificial sequence
<220> FEATURE:
<223> OTHER INFORMATION: Corynephage omega: DT387(I290A)

<400> SEQUENCE: 61
atgggcgctg atgatgttgt tgattcttct aaatcttttg tgatggaaaa ctttttcttcg        60 taccacggga ctaaacctgg ttatgtagat tccattcaaa aggtatacac aaagccaaaa       120
tctggtacac aaggaaatta tgacgatgat tggaaagggt tttatagtac cgacaataaa       180
tacgacgctg cggatactc tgtagataat gaaaacccgc tctctggaaa agctggaggc        240
gtggtcaaag tgacgtatcc aggactgacg aaggttctcg cactaaaagt ggataatgcc       300
gaaactatta gaaagagtt aggtttaagt ctcactgaac cgttgatgga gcaagtcgga        360
acggaagagt ttatcaaaag gttcggtgat ggtgcttcgc gtgtagtgct cagccttccc       420
ttcgctgagg ggagttctag cgttaatat attaataact gggaacaggc gaaagcgtta        480
agcgtagaac ttgagattaa ttttgaaacc cgtggaaaac gtggacaaga tgcgatgtat       540
```

```
gagtatatgg ctcaagcctg tgcaggaaat cgtgtcaggc gatcagtagg tagctcattg    600
tcatgcatca acctggattg ggatgttatc cgtgataaaa ctaaaactaa gatcgaatct    660
ctgaaagaac acggtccgat caaaaacaaa atgagcgaaa gcccgaacaa aactgtatct    720
gaagaaaaag ctaaacagta cctggaagaa ttccaccaga ctgcactgga cacccggaa    780 ctgtctgaac ttaagaccgt tactggtacc aacccggtat cgctggtgc taactacgct    840 gcttgggcag taaacgttgc tcaggttatc gatagcgaaa ctgctgataa cctggaaaaa    900
actaccgcgg ctctgtctat cctgccgggt atcggtagcg taatgggcat cgcagacggc    960
gccgttcacc acaacactga agaaatcgtt gcacagtcta cgctctgag ctctctgatg   1020 gttgctcagg ccatcccgct ggtaggtgaa ctggttgata tcggtttcgc tgcatacaac   1080
ttcgttgaaa gcatcatcaa cctgttccag gttgttcaca actcttacaa ccgcccggcg   1140
catgcatcta gcggaggtgg ctctagcggt ggaggctgt                          1179
```

<210> SEQ ID NO 62
<211> LENGTH: 393
<212> TYPE: PRT
<213> ORGANISM: Artificial sequence
<220> FEATURE:
<223> OTHER INFORMATION: Corynephage omega: DT387(V290A)

<400> SEQUENCE: 62

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255
```

Glu His Pro Glu Leu Ser Glu Leu Lys Thr Val Gly Thr Asn Pro
           260                 265                 270

Val Phe Ala Gly Ala Asn Tyr Ala Ala Trp Ala Val Asn Val Ala Gln
           275                 280                 285

Val Ala Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala His Ala Ser Ser
        370                 375                 380

Gly Gly Gly Ser Ser Gly Gly Gly Cys
385                 390

<210> SEQ ID NO 63
<211> LENGTH: 1179
<212> TYPE: DNA
<213> ORGANISM: Artificial sequence
<220> FEATURE:
<223> OTHER INFORMATION: Corynephage omega: DT387(D291E)

<400> SEQUENCE: 63
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acggtccgat caaaaacaaa atgagcgaaa gcccgaacaa aactgtatct     720
gaagaaaaag ctaaacagta cctggaagaa ttccaccaga ctgcactgga cacccggaa     780 ctgtctgaac ttaagaccgt tactggtacc aacccggtat cgctggtgc taactacgct     840 gcttgggcag taacgttgc tcaggttatc gatagcaaa ctgctgataa cctggaaaaa     900
actaccgcgg ctctgtctat cctgccgggt atcggtagcg taatgggcat cgcagacggc     960
gccgttcacc acaacactga agaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggcg    1140
catgcatcta gcggaggtgg ctctagcggt ggaggctgt                          1179

<210> SEQ ID NO 64
<211> LENGTH: 393

```
<212> TYPE: PRT
<213> ORGANISM: Artificial sequence
<220> FEATURE:
<223> OTHER INFORMATION: Corynephage omega: DT387(D291E)

<400> SEQUENCE: 64

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Glu Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala His Ala Ser Ser
    370                 375                 380

Gly Gly Gly Ser Ser Gly Gly Gly Cys
```

<210> SEQ ID NO 65
<211> LENGTH: 1179
<212> TYPE: DNA
<213> ORGANISM: Artificial sequence
<220> FEATURE:
<223> OTHER INFORMATION: Corynephage omega: DT387(V7AV29A)

<400> SEQUENCE: 65

```
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga ggcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acggtccgat caaaaacaaa atgagcgaaa gcccgaacaa aactgtatct     720
gaagaaaaag ctaaacagta cctggaagaa ttccaccaga ctgcactgga cacccggaa      780
ctgtctgaac ttaagaccgt tactggtacc aacccggtat cgctggtgc taactacgct      840
gcttgggcag taacgttgc tcaggttatc gatagcgaaa ctgctgataa cctggaaaaa     900
actaccgcgg ctctgtctat cctgccgggt atcggtagcg taatgggcat cgcagacggc     960
gccgttcacc acaacactga gaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggcg    1140
catgcatcta gcggaggtgg ctctagcggt ggaggctgt                           1179
```

<210> SEQ ID NO 66
<211> LENGTH: 393
<212> TYPE: PRT
<213> ORGANISM: Artificial sequence
<220> FEATURE:
<223> OTHER INFORMATION: Corynephage omega: DT387(V7AV29A)

<400> SEQUENCE: 66

```
Met Gly Ala Asp Asp Val Ala Asp Ser Ser Lys Ser Phe Val Met Glu
1               5                   10                  15
Asn Phe Ser Ser Tyr His Gly Thr Lys Pro Gly Tyr Ala Asp Ser Ile
            20                  25                  30
Gln Lys Gly Ile Gln Lys Pro Lys Ser Gly Thr Gln Gly Asn Tyr Asp
        35                  40                  45
Asp Asp Trp Lys Gly Phe Tyr Ser Thr Asp Asn Lys Tyr Asp Ala Ala
    50                  55                  60
Gly Tyr Ser Val Asp Asn Glu Asn Pro Leu Ser Gly Lys Ala Gly Gly
65                  70                  75                  80
Val Val Lys Val Thr Tyr Pro Gly Leu Thr Lys Val Leu Ala Leu Lys
                85                  90                  95
```

-continued

Val Asp Asn Ala Glu Thr Ile Lys Lys Glu Leu Gly Leu Ser Leu Thr
            100                 105                 110

Glu Pro Leu Met Glu Gln Val Gly Thr Glu Phe Ile Lys Arg Phe
        115                 120                 125

Gly Asp Gly Ala Ser Arg Val Val Leu Ser Leu Pro Phe Ala Glu Gly
130                 135                 140

Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Glu Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
            210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
            290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala His Ala Ser Ser
370                 375                 380

Gly Gly Gly Ser Ser Gly Gly Gly Cys
385                 390

<210> SEQ ID NO 67
<211> LENGTH: 1179
<212> TYPE: DNA
<213> ORGANISM: Artificial sequence
<220> FEATURE:
<223> OTHER INFORMATION: Corynephage omega: DT387(V7SV29A)

<400> SEQUENCE: 67
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420

```
ttcgctgagg ggagttctag cgttgaatat attaataact gggaacaggc gaaagcgtta      480
agcgtagaac ttgagattaa ttttgaaacc cgtggaaaac gtggccaaga tgcgatgtat      540
gagtatatgg ctcaagcctg tgcaggaaat cgtgtcaggc gatcagtagg tagctcattg      600
tcatgcatca acctggattg ggatgttatc cgtgataaaa ctaaaactaa gatcgaatct      660
ctgaaagaac acggtccgat caaaaacaaa atgagcgaaa gcccgaacaa aactgtatct      720
gaagaaaaag ctaaacagta cctggaagaa ttccaccaga ctgcactgga cacccggaa       780 ctgtctgaac ttaagaccgt tactggtacc aacccggtat cgctggtgc taactacgct       840 gcttgggcag taacgttgc tcaggttatc gatagcgaaa ctgctgataa cctggaaaaa       900
actaccgcgg ctctgtctat cctgccgggt atcggtagcg taatgggcat cgcagacggc      960
gccgttcacc acaacactga agaaatcgtt gcacagtcta cgctctgag ctctctgatg      1020 gttgctcagg ccatcccgct ggtaggtgaa ctggttgata tcggtttcgc tgcatacaac     1080
ttcgttgaaa gcatcatcaa cctgttccag gttgttcaca actcttacaa ccgcccggcg     1140
catgcatcta gcggaggtgg ctctagcggt ggaggctgt                             1179
```

<210> SEQ ID NO 68
<211> LENGTH: 393
<212> TYPE: PRT
<213> ORGANISM: Artificial sequence
<220> FEATURE:
<223> OTHER INFORMATION: Corynephage omega: DT387(V7SV29A)

<400> SEQUENCE: 68

```
Met Gly Ala Asp Asp Val Ser Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
```

```
            225                 230                 235                 240
Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala His Ala Ser Ser
    370                 375                 380

Gly Gly Gly Ser Ser Gly Gly Gly Cys
385                 390
```

<210> SEQ ID NO 69
<211> LENGTH: 1179
<212> TYPE: DNA
<213> ORGANISM: Artificial sequence
<220> FEATURE:
<223> OTHER INFORMATION: Corynephage omega: DT387(D8EV29A)

<400> SEQUENCE: 69

```
atgggcgctg atgatgttgt tgattcttct aaatcttttg tgatggaaaa ctttttcttcg      60
taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg gagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acgtccgat caaaaacaaa atgagcgaaa gcccgaacaa actgtatct     720
gaagaaaaag ctaaacagta cctggaagaa ttccaccaga ctgcactgga cacccggaa     780
ctgtctgaac ttaagaccgt tactggtacc aacccggtat cgctggtgc taactacgct     840
gcttgggcag taacgttgc tcaggttatc gatagcgaaa ctgctgataa cctggaaaaa     900
actaccgcgg ctcgtctat cctgccgggt atcggtagcg taatgggcat cgcagacggc     960
gccgttcacc acaacactga gaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggcg    1140
```
catgcatcta gcggaggtgg ctctagcggt ggaggctgt        1179

<210> SEQ ID NO 70
<211> LENGTH: 393
<212> TYPE: PRT
<213> ORGANISM: Artificial sequence
<220> FEATURE:
<223> OTHER INFORMATION: Corynephage omega: DT387(D8EV29A)

<400> SEQUENCE: 70

```
Met Gly Ala Asp Asp Val Val Glu Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365
```

```
Phe Gln Val Val His Asn Ser Tyr Asn Arg Pro Ala His Ala Ser Ser
        370                 375                 380

Gly Gly Gly Ser Ser Gly Gly Gly Cys
385                 390

<210> SEQ ID NO 71
<211> LENGTH: 1179
<212> TYPE: DNA
<213> ORGANISM: Artificial
<220> FEATURE:
<223> OTHER INFORMATION: Corynephage omega: DT387(D8SV29A)

<400> SEQUENCE: 71
atgggcgctg atgatgttgt tgattcttct aaatcttttg tgatggaaaa ctttttcttcg      60 taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg gagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcatca acctggattg ggatgttatc cgtgataaaa ctaaaactaa gatcgaatct     660
ctgaaagaac acggtccgat caaaaacaaa atgagcgaaa gcccgaacaa aactgtatct     720
gaagaaaaag ctaaacagta cctggaagaa ttccaccaga ctgcactgga cacccggaa     780 ctgtctgaac ttaagaccgt tactggtacc aacccggtat cgctggtgc taactacgct     840 gcttgggcag taacgttgc tcaggttatc gatagcgaaa ctgctgataa cctggaaaaa     900
actaccgcgg ctctgtctat cctgccgggt atcggtagcg taatgggcat cgcagacggc     960
gccgttcacc acaacactga agaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggcg    1140
catgcatcta gcggaggtgg ctctagcggt ggaggctgt                            1179

<210> SEQ ID NO 72
<211> LENGTH: 393
<212> TYPE: PRT
<213> ORGANISM: Artificial sequence
<220> FEATURE:
<223> OTHER INFORMATION: Corynephage omega: DT387(D8SV29A)

<400> SEQUENCE: 72

Met Gly Ala Asp Asp Val Val Ser Ser Lys Ser Phe Val Met Glu
1               5                  10                  15

Asn Phe Ser Ser Tyr His Gly Thr Lys Pro Gly Tyr Ala Asp Ser Ile
                20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
```

```
                65                  70                  75                  80
Val Val Lys Val Thr Tyr Pro Gly Leu Thr Lys Val Leu Ala Leu Lys
                    85                  90                  95

Val Asp Asn Ala Glu Thr Ile Lys Lys Glu Leu Gly Leu Ser Leu Thr
                100                 105                 110

Glu Pro Leu Met Glu Gln Val Gly Thr Glu Phe Ile Lys Arg Phe
            115                 120                 125

Gly Asp Gly Ala Ser Arg Val Val Leu Ser Leu Pro Phe Ala Glu Gly
        130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
                180                 185                 190

Arg Arg Ser Val Gly Ser Ser Leu Ser Cys Ile Asn Leu Asp Trp Asp
            195                 200                 205

Val Ile Arg Asp Lys Thr Lys Thr Lys Ile Glu Ser Leu Lys Glu His
        210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala His Ala Ser Ser
        370                 375                 380

Gly Gly Gly Ser Ser Gly Gly Gly Cys
385                 390

<210> SEQ ID NO 73
<211> LENGTH: 1167
<212> TYPE: DNA
<213> ORGANISM: Artificial sequence
<220> FEATURE:
<223> OTHER INFORMATION: Corynephage omega: DT387(V29AD291E)
<220> FEATURE:
<221> NAME/KEY: CDS
<222> LOCATION: (1)..(1167)

<400> SEQUENCE: 73 atg ggc gct gat gat gtt gtt gat tct tct aaa tct ttt gtg atg gaa    48
Met Gly Ala Asp Asp Val Val Asp Ser Ser Lys Ser Phe Val Met Glu
1               5                   10                  15 aac ttt tct tcg tac cac ggg act aaa cct ggt tat gca gat tcc att    96
```

```
                Asn Phe Ser Ser Tyr His Gly Thr Lys Pro Gly Tyr Ala Asp Ser Ile
                             20                  25                  30 caa aaa ggt ata caa aag cca aaa tct ggt aca caa gga aat tat gac         144
Gln Lys Gly Ile Gln Lys Pro Lys Ser Gly Thr Gln Gly Asn Tyr Asp
         35                  40                  45 gat gat tgg aaa ggg ttt tat agt acc gac aat aaa tac gac gct gcg         192
Asp Asp Trp Lys Gly Phe Tyr Ser Thr Asp Asn Lys Tyr Asp Ala Ala
 50                  55                  60 gga tac tct gta gat aat gaa aac ccg ctc tct gga aaa gct gga ggc         240
Gly Tyr Ser Val Asp Asn Glu Asn Pro Leu Ser Gly Lys Ala Gly Gly
 65                  70                  75                  80 gtg gtc aaa gtg acg tat cca gga ctg acg aag gtt ctc gca cta aaa         288
Val Val Lys Val Thr Tyr Pro Gly Leu Thr Lys Val Leu Ala Leu Lys
                 85                  90                  95 gtg gat aat gcc gaa act att aag aaa gag tta ggt tta agt ctc act         336
Val Asp Asn Ala Glu Thr Ile Lys Lys Glu Leu Gly Leu Ser Leu Thr
             100                 105                 110 gaa ccg ttg atg gag caa gtc gga acg gaa gag ttt atc aaa agg ttc         384
Glu Pro Leu Met Glu Gln Val Gly Thr Glu Glu Phe Ile Lys Arg Phe
         115                 120                 125 ggt gat ggt gct tcg cgt gta gtg ctc agc ctt ccc ttc gct gag ggg         432
Gly Asp Gly Ala Ser Arg Val Val Leu Ser Leu Pro Phe Ala Glu Gly
 130                 135                 140 agt tct agc gtt gaa tat att aat aac tgg gaa cag gcg aaa gcg tta         480
Ser Ser Ser Val Glu Tyr Ile Asn Asn Trp Glu Gln Ala Lys Ala Leu
145                 150                 155                 160 agc gta gaa ctt gag att aat ttt gaa acc cgt gga aaa cgt ggc caa         528
Ser Val Glu Leu Glu Ile Asn Phe Glu Thr Arg Gly Lys Arg Gly Gln
                 165                 170                 175 gat gcg atg tat gag tat atg gct caa gcc tgt gca gga aat cgt gtc         576
Asp Ala Met Tyr Glu Tyr Met Ala Gln Ala Cys Ala Gly Asn Arg Val
             180                 185                 190 agg cga tca gta ggt agc tca ttg tca tgc atc aac ctg gat tgg gat         624
Arg Arg Ser Val Gly Ser Ser Leu Ser Cys Ile Asn Leu Asp Trp Asp
         195                 200                 205 gtt atc cgt gat aaa act aaa act aag atc gaa tct ctg aaa gaa cac         672
Val Ile Arg Asp Lys Thr Lys Thr Lys Ile Glu Ser Leu Lys Glu His
 210                 215                 220 ggt ccg atc aaa aac aaa atg agc gaa agc ccg aac aaa act gta tct         720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg         768
Glu Glu Lys Ala Lys Gln Tyr Leu Glu Glu Phe His Gln Thr Ala Leu
                 245                 250                 255 gaa cac ccg gaa ctg tct gaa ctt aag acc gtt act ggt acc aac ccg         816
Glu His Pro Glu Leu Ser Glu Leu Lys Thr Val Thr Gly Thr Asn Pro
             260                 265                 270 gta ttc gct ggt gct aac tac gct gct tgg gca gta aac gtt gct cag         864
Val Phe Ala Gly Ala Asn Tyr Ala Ala Trp Ala Val Asn Val Ala Gln
         275                 280                 285 gtt atc gaa agc gaa act gct gat aac ctg gaa aaa act acc gcg gct         912
Val Ile Glu Ser Glu Thr Ala Asp Asn Leu Glu Lys Thr Thr Ala Ala
 290                 295                 300 ctg tct atc ctg ccg ggt atc ggt agc gta atg ggc atc gca gac ggc         960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg        1008
Ala Val His His Asn Thr Glu Glu Ile Val Ala Gln Ser Ile Ala Leu
                 325                 330                 335 agc tct ctg atg gtt gct cag gcc atc ccg ctg gta ggt gaa ctg gtt        1056
```

```
Ser Ser Leu Met Val Ala Gln Ala Ile Pro Leu Val Gly Glu Leu Val
        340                 345                 350 gat atc ggt ttc gct gca tac aac ttc gtt gaa agc atc atc aac ctg      1104
Asp Ile Gly Phe Ala Ala Tyr Asn Phe Val Glu Ser Ile Ile Asn Leu
        355                 360                 365 ttc cag gtt gtt cac aac tct tac aac cgc ccg gct tac tct ccg ggt      1152
Phe Gln Val Val His Asn Ser Tyr Asn Arg Pro Ala Tyr Ser Pro Gly
    370                 375                 380 cac aag acg cat gca                                                   1167
His Lys Thr His Ala
385

<210> SEQ ID NO 74
<211> LENGTH: 389
<212> TYPE: PRT
<213> ORGANISM: Artificial sequence
<220> FEATURE:
<223> OTHER INFORMATION: Corynephage omega: DT387(V29AD291E)

<400> SEQUENCE: 74

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Glu Ser Glu Thr Ala Asp Asn Leu Glu Lys Thr Thr Ala Ala
```

```
                290                 295                 300
Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
                370                 375                 380

His Lys Thr His Ala
385
```

<210> SEQ ID NO 75
<211> LENGTH: 1179
<212> TYPE: DNA
<213> ORGANISM: Artificial sequence
<220> FEATURE:
<223> OTHER INFORMATION: Corynephage omega: DT387(V7AV29AI290A)

<400> SEQUENCE: 75

| | | |
|---|---|---|
| atgggcgctg atgatgttgt tgattcttct aaatcttttg tgatggaaaa cttttcttcg | 60 |
| taccacggga ctaaacctgg ttatgtagat tccattcaaa aaggtataca aaagccaaaa | 120 |
| tctggtacac aaggaaatta tgacgatgat tggaaagggt tttatagtac cgacaataaa | 180 |
| tacgacgctg cgggatactc tgtagataat gaaaacccgc tctctggaaa agctggaggc | 240 |
| gtggtcaaag tgacgtatcc aggactgacg aaggttctcg cactaaaagt ggataatgcc | 300 |
| gaaactatta gaaagagtt aggtttaagt ctcactgaac cgttgatgga gcaagtcgga | 360 |
| acggaagagt ttatcaaaag gttcggtgat ggtgcttcgc gtgtagtgct cagccttccc | 420 |
| ttcgctgagg ggagttctag cgttgaatat attaataact gggaacaggc gaaagcgtta | 480 |
| agcgtagaac ttgagattaa ttttgaaacc cgtggaaaac gtggccaaga tgcgatgtat | 540 |
| gagtatatgg ctcaagcctg tgcaggaaat cgtgtcaggc gatcagtagg tagctcattg | 600 |
| tcatgcatca acctggattg ggatgttatc cgtgataaaa ctaaaactaa gatcgaatct | 660 |
| ctgaaagaac acgtccgat caaaaacaaa atgagcgaaa gcccgaacaa aactgtatct | 720 |
| gaagaaaaag ctaaacagta cctggaagaa ttccaccaga ctgcactgga cacccggaa | 780 |
| ctgtctgaac ttaagaccgt tactggtacc aacccggtat cgctggtgc taactacgct | 840 |
| gcttgggcag taacgttgc tcacgttatc gatagcgaaa ctgctgataa cctggaaaaa | 900 |
| actaccgcgg ctctgtctat cctgccgggt atcggtagcg taatgggcat cgcagacggc | 960 |
| gccgttcacc acaacactga gaaaatcgtt gcacagtcta tcgctctgag ctctctgatg | 1020 |
| gttgctcagg ccatcccgct ggtaggtgaa ctggttgata tcggtttcgc tgcatacaac | 1080 |
| ttcgttgaaa gcatcatcaa cctgttccag gttgttcaca actcttacaa ccgcccggcg | 1140 |
| catgcatcta gcggaggtgg ctctagcggt ggaggctgt | 1179 |

<210> SEQ ID NO 76
<211> LENGTH: 393
<212> TYPE: PRT
<213> ORGANISM: Artificial sequence
<220> FEATURE:
<223> OTHER INFORMATION: Corynephage omega: DT387(V7AV29AI290A)

<400> SEQUENCE: 76

```
Met Gly Ala Asp Asp Val Ala Asp Ser Ser Lys Ser Phe Val Met Glu
 1               5                  10                  15

Asn Phe Ser Ser Tyr His Gly Thr Lys Pro Gly Tyr Ala Asp Ser Ile
             20                  25                  30

Gln Lys Gly Ile Gln Lys Pro Lys Ser Gly Thr Gln Gly Asn Tyr Asp
         35                  40                  45

Asp Asp Trp Lys Gly Phe Tyr Ser Thr Asp Asn Lys Tyr Asp Ala Ala
     50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
             100                 105                 110

Glu Pro Leu Met Glu Gln Val Gly Thr Glu Glu Phe Ile Lys Arg Phe
         115                 120                 125

Gly Asp Gly Ala Ser Arg Val Val Leu Ser Leu Pro Phe Ala Glu Gly
     130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                 165                 170                 175

Asp Ala Met Tyr Glu Tyr Met Ala Gln Ala Cys Ala Gly Asn Arg Val
             180                 185                 190

Arg Arg Ser Val Gly Ser Ser Leu Ser Cys Ile Asn Leu Asp Trp Asp
         195                 200                 205

Val Ile Arg Asp Lys Thr Lys Thr Lys Ile Glu Ser Leu Lys Glu His
     210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                 245                 250                 255

Glu His Pro Glu Leu Ser Glu Leu Lys Thr Val Thr Gly Thr Asn Pro
             260                 265                 270

Val Phe Ala Gly Ala Asn Tyr Ala Ala Trp Ala Val Asn Val Ala His
         275                 280                 285

Val Ala Asp Ser Glu Thr Ala Asp Asn Leu Glu Lys Thr Thr Ala Ala
     290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                 325                 330                 335

Ser Ser Leu Met Val Ala Gln Ala Ile Pro Leu Val Gly Glu Leu Val
             340                 345                 350

Asp Ile Gly Phe Ala Ala Tyr Asn Phe Val Glu Ser Ile Ile Asn Leu
         355                 360                 365

Phe Gln Val Val His Asn Ser Tyr Asn Arg Pro Ala His Ala Ser Ser
     370                 375                 380

Gly Gly Gly Ser Ser Gly Gly Gly Cys
385                 390

<210> SEQ ID NO 77
<211> LENGTH: 1179
<212> TYPE: DNA
<213> ORGANISM: Artificial sequence
```

<220> FEATURE:
<223> OTHER INFORMATION: Corynephage omega: DT387(V7AV29AD291E)

<400> SEQUENCE: 77

```
atgggcgctg atgatgttgt tgattcttct aaatcttttg tgatggaaaa cttttcttcg        60
taccacggga ctaaacctgg ttatgtagat tccattcaaa aaggtataca aaagccaaaa       120
tctggtacac aaggaaatta tgacgatgat tggaaagggt tttatagtac cgacaataaa       180
tacgacgctg cgggatactc tgtagataat gaaaacccgc tctctggaaa agctggaggc       240
gtggtcaaag tgacgtatcc aggactgacg aaggttctcg cactaaaagt ggataatgcc       300
gaaactatta gaaagagtt aggtttaagt ctcactgaac cgttgatgga gcaagtcgga       360
acggaagagt ttatcaaaag gttcggtgat ggtgcttcgc gtgtagtgct cagccttccc       420
ttcgctgagg ggagttctag cgttaatat attaataact gggaacaggc gaaagcgtta       480
agcgtagaac ttgagattaa ttttgaaacc cgtggaaaac gtggccaaga tgcgatgtat       540
gagtatatgg ctcaagcctg tgcaggaaat cgtgtcaggc gatcagtagg tagctcattg       600
tcatgcatca acctggattg ggatgttatc cgtgataaaa ctaaaactaa gatcgaatct       660
ctgaaagaac acggtccgat caaaaacaaa atgagcgaaa gcccgaacaa aactgtatct       720
gaagaaaaag ctaaacagta cctggaagaa ttccaccaga ctgcactgga cacccggaa       780
ctgtctgaac ttaagaccgt tactggtacc aaccccggtat cgctggtgc taactacgct       840
gcttgggcag taacgttgc tcaggttatc gatagcgaaa ctgctgataa cctggaaaaa       900
actaccgcgg ctctgtctat cctgccgggt atcggtagcg taatgggcat cgcagacggc       960
gccgttcacc acaacactga agaaatcgtt gcacagtcta tcgctctgag ctctctgatg      1020
gttgctcagg ccatcccgct ggtaggtgaa ctggttgata tcggtttcgc tgcatacaac      1080
ttcgttgaaa gcatcatcaa cctgttccag gttgttcaca actcttacaa ccgcccggcg      1140
catgcatcta gcggaggtgg ctctagcggt ggaggctgt                             1179
```

<210> SEQ ID NO 78
<211> LENGTH: 393
<212> TYPE: PRT
<213> ORGANISM: Artificial sequence
<220> FEATURE:
<223> OTHER INFORMATION: Corynephage omega: DT387(V7AV29AD291E)

<400> SEQUENCE: 78

```
Met Gly Ala Asp Asp Val Ala Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
```

```
                130                 135                 140
Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
                180                 185                 190

Arg Arg Ser Val Gly Ser Ser Leu Ser Cys Ile Asn Leu Asp Trp Asp
                195                 200                 205

Val Ile Arg Asp Lys Thr Lys Thr Lys Ile Glu Ser Leu Lys Glu His
                210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
                260                 265                 270

Val Phe Ala Gly Ala Asn Tyr Ala Ala Trp Ala Val Asn Val Ala Gln
                275                 280                 285

Val Ile Glu Ser Glu Thr Ala Asp Asn Leu Glu Lys Thr Thr Ala Ala
                290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala His Ala Ser Ser
                370                 375                 380

Gly Gly Gly Ser Ser Gly Gly Gly Cys
385                 390
```

<210> SEQ ID NO 79
<211> LENGTH: 1602
<212> TYPE: DNA
<213> ORGANISM: Artificial sequence
<220> FEATURE:
<223> OTHER INFORMATION: Corynephage omega: DT387(V7SV29A)linkerIL2

<400> SEQUENCE: 79

```
atgggcgctg atgatgttgt tgattcttct aaatcttttg tgatggaaaa cttttcttcg     60
taccacggga ctaaacctgg ttatgtagat tccattcaaa aaggtataca aaagccaaaa    120
tctggtacac aaggaaatta tgacgatgat tggaaagggt ttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta gaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgcaggaaat cgtgtcaggc gatcagtagg tagctcattg    600
```

-continued

```
tcatgcatca acctggattg ggatgttatc cgtgataaaa ctaaaactaa gatcgaatct    660
ctgaaagaac acgtccgat caaaaacaaa atgagcgaaa gcccgaacaa aactgtatct    720
gaagaaaaag ctaaacagta cctggaagaa ttccaccaga ctgcactgga cacccggaa    780 ctgtctgaac ttaagaccgt tactggtacc aacccggtat cgctggtgc taactacgct    840 gcttgggcag taaacgttgc tcaggttatc gatagcgaaa ctgctgataa cctggaaaaa    900
actaccgcgg ctctgtctat cctgccgggt atcggtagcg taatgggcat cgcagacggc    960
gccgttcacc acaacactga agaaatcgtt gcacagtcta tcgctctgag ctctctgatg   1020
gttgctcagg ccatcccgct ggtaggtgaa ctggttgata tcggtttcgc tgcatacaac   1080
ttcgttgaaa gcatcatcaa cctgttccag gttgttcaca actcttacaa ccgcccggct   1140
tactctccgg gtcacaagac gcatgcatct agcggaggtg gctctagcgg tggaggatcc   1200
gcacctactt ctagctctac caagaaaacc cagctgcagc tcgagcacct gctgctggat   1260
ttgcagatga tcctgaacgg tatcaacaat tacaagaacc cgaaactgac gcgtatgctg   1320
accttcaagt tctacatgcc gaagaaggcc accgaactga acacctgct gcagtgtcta   1380 gaagaagaac tgaaaccgct ggaggaagtt ctgaacctgg ctcagtctaa aaacttccac   1440
ctgcggccgc gtgacctgat ctctaacatc aacgtaatcg ttctggaact gaagggctct   1500
gaaaccacct tcatgtgtga atacgctgat gagaccgcaa ccatcgtaga attcctgaac   1560
cgttggatca ccttctgtca gtctatcatc tctaccctga cc                      1602
```

<210> SEQ ID NO 80
<211> LENGTH: 534
<212> TYPE: PRT
<213> ORGANISM: Artificial sequence
<220> FEATURE:
<223> OTHER INFORMATION: Corynephage omega: DT387(V7SV29A)linkerIL2

<400> SEQUENCE: 80

```
Met Gly Ala Asp Asp Val Ser Asp Ser Ser Lys Ser Phe Val Met Glu
  1               5                  10                  15

Asn Phe Ser Ser

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Ser Ser Gly Gly Ser Ser Gly Gly Ser
385                 390                 395                 400

Ala Pro Thr Ser Ser Thr Lys Lys Thr Gln Leu Gln Leu Glu His
                405                 410                 415

Leu Leu Leu Asp Leu Gln Met Ile Leu Asn Gly Ile Asn Asn Tyr Lys
            420                 425                 430

Asn Pro Lys Leu Thr Arg Met Leu Thr Phe Lys Phe Tyr Met Pro Lys
        435                 440                 445

Lys Ala Thr Glu Leu Lys His Leu Leu Gln Cys Leu Glu Glu Glu Leu
    450                 455                 460

Lys Pro Leu Glu Glu Val Leu Asn Leu Ala Gln Ser Lys Asn Phe His
465                 470                 475                 480

Leu Arg Pro Arg Asp Leu Ile Ser Asn Ile Asn Val Ile Val Leu Glu
                485                 490                 495

Leu Lys Gly Ser Glu Thr Thr Phe Met Cys Glu Tyr Ala Asp Glu Thr
            500                 505                 510

Ala Thr Ile Val Glu Phe Leu Asn Arg Trp Ile Thr Phe Cys Gln Ser
        515                 520                 525

Ile Ile Ser Thr Leu Thr
    530

<210> SEQ ID NO 81
<211> LENGTH: 1602
<212> TYPE: DNA
<213> ORGANISM: Artificial sequence
<220> FEATURE:
<223> OTHER INFORMATION: Corynephage omega: DT387(D8EV29AlinkerIL2

<400> SEQUENCE: 81
atgggcgctg atgatgttgt tgattcttct aaatcttttg tgatggaaaa cttttcttcg      60
taccacggga ctaaacctgg ttatgtagat tccattcaaa aaggtataca aaagccaaaa     120

```
tctggtacac aaggaaatta tgacgatgat tggaaagggt tttatagtac cgacaataaa    180
tacgacgctg cgggatactc tgtagtaaat gaaaacccgc tctctggaaa agctggaggc    240
gtggtcaaag tgacgtatcc aggactgacg aaggttctcg cactaaaagt ggataatgcc    300
gaaactatta agaaagagtt aggtttaagt ctcactgaac cgttgatgga gcaagtcgaa    360
acggaagagt ttatcaaaag gttcggtgat ggtgcttcgc gtgtagtgct cagccttccc    420
ttcgctgagg ggagttctag cgttaatat attaataact gggaacaggc gaaagcgtta    480
agcgtagaac ttgagattaa ttttgaaacc cgtggaaaac gtggccaaga tgcgatgtat    540
gattatatgg ctcaagcctg tgcaggaaat cgtgtcaggc gatcagtagg tagctcattg    600
tcatgcatca acctggattg ggatgttatc cgtgataaaa ctaaaactaa gatcgaatct    660
ctgaaagaac acggtccgat caaaaacaaa atgagcgaaa gcccgaacaa aactgtatct    720
gaagaaaaag ctaaacagta cctggaagaa ttccaccaga ctgcactgga cacccggaa    780
ctgtctgaac ttaagaccgt tactggtacc aacccggtat cgctggtgc taactacgct    840
gcttgggcag taacgttgc tcaggttatc gatagcgaaa ctgctgataa cctggaaaaa    900
actaccgcgg ctctgtctat cctgccgggt atcggtagcg taatgggcat cgcagacggc    960
gccgttcacc acaacactga agaaatcgtt gcacagtcta tcgctctgag ctctctgatg    1020
gttgctcagg ccatcccgct ggtaggtgaa ctggttgata tcggtttcgc tgcatacaac    1080
ttcgttgaaa gcatcatcaa cctgttccag gttgttcaca actcttacaa ccgcccggct    1140
tactctccgg gtcacaagac gcatgcatct agcggaggtg gctctagcgg tggaggatcc    1200
gcacctactt ctagctctac caagaaaacc cagctgcagc tcgagcacct gctgctggat    1260
ttgcagatga tcctgaacgg tatcaacaat tacaagaacc cgaaactgac gcgtatgctg    1320
accttcaagt tctacatgcc gaagaaggcc accgaactga acacctgct gcagtgtcta    1380
gaagaagaac tgaaaccgct ggaggaagtt ctgaacctgg ctcagtctaa aaacttccac    1440
ctgcggccgc gtgacctgat ctctaacatc aacgtaatcg ttctggaact gaagggctct    1500
gaaaccacct tcatgtgtga atacgctgat gagaccgcaa ccatcgtaga attcctgaac    1560
cgttggatca ccttctgtca gtctatcatc tctaccctga cc                      1602

<210> SEQ ID NO 82
<211> LENGTH: 534
<212> TYPE: PRT
<213> ORGANISM: Artificial sequence
<220> FEATURE:
<223> OTHER INFORMATION: Corynephage omega: DT387(D8EV29AlinkerIL2

<400> SEQUENCE: 82

Met Gly Ala Asp Asp Val Val Glu Ser Ser Lys Ser Phe Val Met Glu
1               5                   10                  15

Asn Phe Ser Ser Tyr His Gly Thr Lys Pro Gly Tyr Ala Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr Asp Asn Lys Tyr Asp Ala Ala
        50                  55                  60

Gly Tyr Ser Val Val Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110
```

Glu Pro Leu Met Glu Gln Val Glu Thr Glu Glu Phe Ile Lys Arg Phe
115                 120                 125
Gly Asp Gly Ala Ser Arg Val Val Leu Ser Leu Pro Phe Ala Glu Gly
130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
            165                 170                 175
Asp Ala Met Tyr Asp Tyr Met Ala Gln Ala Cys Ala Gly Asn Arg Val
                180                 185                 190
Arg Arg Ser Val Gly Ser Ser Leu Ser Cys Ile Asn Leu Asp Trp Asp
        195                 200                 205
Val Ile Arg Asp Lys Thr Lys Thr Lys Ile Glu Ser Leu Lys Glu His
210                 215                 220
Gly Pro Ile Lys Asn Lys Met Ser Glu Ser Pro Asn Lys Thr Val Ser
225                 230                 235                 240
Glu Glu Lys Ala Lys Gln Tyr Leu Glu Glu Phe His Gln Thr Ala Leu
            245                 250                 255
Glu His Pro Glu Leu Ser Glu Leu Lys Thr Val Thr Gly Thr Asn Pro
            260                 265                 270
Val Phe Ala Gly Ala Asn Tyr Ala Ala Trp Ala Val Asn Val Ala Gln
        275                 280                 285
Val Ile Asp Ser Glu Thr Ala Asp Asn Leu Glu Lys Thr Thr Ala Ala
290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
            325                 330                 335
Ser Ser Leu Met Val Ala Gln Ala Ile Pro Leu Val Gly Glu Leu Val
            340                 345                 350
Asp Ile Gly Phe Ala Ala Tyr Asn Phe Val Glu Ser Ile Ile Asn Leu
        355                 360                 365
Phe Gln Val Val His Asn Ser Tyr Asn Arg Pro Ala Tyr Ser Pro Gly
370                 375                 380
His Lys Thr His Ala Ser Ser Gly Gly Ser Ser Gly Gly Gly Ser
385                 390                 395                 400
Ala Pro Thr Ser Ser Thr Lys Lys Thr Gln Leu Gln Leu Glu His
            405                 410                 415
Leu Leu Leu Asp Leu Gln Met Ile Leu Asn Gly Ile Asn Asn Tyr Lys
            420                 425                 430
Asn Pro Lys Leu Thr Arg Met Leu Thr Phe Lys Phe Tyr Met Pro Lys
        435                 440                 445
Lys Ala Thr Glu Leu Lys His Leu Leu Gln Cys Leu Glu Glu Glu Leu
450                 455                 460
Lys Pro Leu Glu Glu Val Leu Asn Leu Ala Gln Ser Lys Asn Phe His
465                 470                 475                 480
Leu Arg Pro Arg Asp Leu Ile Ser Asn Ile Asn Val Ile Val Leu Glu
            485                 490                 495
Leu Lys Gly Ser Glu Thr Thr Phe Met Cys Glu Tyr Ala Asp Glu Thr
            500                 505                 510
Ala Thr Ile Val Glu Phe Leu Asn Arg Trp Ile Thr Phe Cys Gln Ser
        515                 520                 525
Ile Ile Ser Thr Leu Thr

<210> SEQ ID NO 83
<211> LENGTH: 1164
<212> TYPE: DNA
<213> ORGANISM: Artificial sequence
<220> FEATURE:
<223> OTHER INFORMATION: Corynephage omega: DT387(AD8)
<220> FEATURE:
<221> NAME/KEY: CDS
<222> LOCATION: (1)..(1164)

<400> SEQUENCE: 83

| | | | | | | | | | | | | | | | | |
|---|---|---|---|---|---|---|---|---|---|---|---|---|---|---|---|---|
| atg | ggc | gct | gat | gat | gtt | gtt | tct | tct | aaa | tct | ttt | gtg | atg | gaa | aac | 48 |
| Met | Gly | Ala | Asp | Asp | Val | Val | Ser | Ser | Lys | Ser | Phe | Val | Met | Glu | Asn | |
| 1 | | | | 5 | | | | | 10 | | | | | 15 | | |
| ttt | tct | tcg | tac | cac | ggg | act | aaa | cct | ggt | tat | gta | gat | tcc | att | caa | 96 |
| Phe | Ser | Ser | Tyr | His | Gly | Thr | Lys | Pro | Gly | Tyr | Val | Asp | Ser | Ile | Gln | |
| | | | 20 | | | | | 25 | | | | | 30 | | | |
| aaa | ggt | ata | caa | aag | cca | aaa | tct | ggt | aca | caa | gga | aat | tat | gac | gat | 144 |
| Lys | Gly | Ile | Gln | Lys | Pro | Lys | Ser | Gly | Thr | Gln | Gly | Asn | Tyr | Asp | Asp | |
| | | | 35 | | | | | 40 | | | | | 45 | | | |
| gat | tgg | aaa | ggg | ttt | tat | agt | acc | gac | aat | aaa | tac | gac | gct | gcg | gga | 192 |
| Asp | Trp | Lys | Gly | Phe | Tyr | Ser | Thr | Asp | Asn | Lys | Tyr | Asp | Ala | Ala | Gly | |
| | 50 | | | | | 55 | | | | | 60 | | | | | |
| tac | tct | gta | gat | aat | gaa | aac | ccg | ctc | tct | gga | aaa | gct | gga | ggc | gtg | 240 |
| Tyr | Ser | Val | Asp | Asn | Glu | Asn | Pro | Leu | Ser | Gly | Lys | Ala | Gly | Gly | Val | |
| 65 | | | | | 70 | | | | | 75 | | | | | 80 | |
| gtc | aaa | gtg | acg | tat | cca | gga | ctg | acg | aag | gtt | ctc | gca | cta | aaa | gtg | 288 |
| Val | Lys | Val | Thr | Tyr | Pro | Gly | Leu | Thr | Lys | Val | Leu | Ala | Leu | Lys | Val | |
| | | | | 85 | | | | | 90 | | | | | 95 | | |
| gat | aat | gcc | gaa | act | att | aag | aaa | gag | tta | ggt | tta | agt | ctc | act | gaa | 336 |
| Asp | Asn | Ala | Glu | Thr | Ile | Lys | Lys | Glu | Leu | Gly | Leu | Ser | Leu | Thr | Glu | |
| | | | 100 | | | | | 105 | | | | | 110 | | | |
| ccg | ttg | atg | gag | caa | gtc | gga | acg | gaa | gag | ttt | atc | aaa | agg | ttc | ggt | 384 |
| Pro | Leu | Met | Glu | Gln | Val | Gly | Thr | Glu | Glu | Phe | Ile | Lys | Arg | Phe | Gly | |
| | | 115 | | | | | 120 | | | | | 125 | | | | |
| gat | ggt | gct | tcg | cgt | gta | gtg | ctc | agc | ctt | ccc | ttc | gct | gag | ggg | agt | 432 |
| Asp | Gly | Ala | Ser | Arg | Val | Val | Leu | Ser | Leu | Pro | Phe | Ala | Glu | Gly | Ser | |
| | 130 | | | | | 135 | | | | | 140 | | | | | |
| tct | agc | gtt | gaa | tat | att | aat | aac | tgg | gaa | cag | gcg | aaa | gcg | tta | agc | 480 |
| Ser | Ser | Val | Glu | Tyr | Ile | Asn | Asn | Trp | Glu | Gln | Ala | Lys | Ala | Leu | Ser | |
| 145 | | | | | 150 | | | | | 155 | | | | | 160 | |
| gta | gaa | ctt | gag | att | aat | ttt | gaa | acc | cgt | gga | aaa | cgt | ggc | caa | gat | 528 |
| Val | Glu | Leu | Glu | Ile | Asn | Phe | Glu | Thr | Arg | Gly | Lys | Arg | Gly | Gln | Asp | |
| | | | | 165 | | | | | 170 | | | | | 175 | | |
| gcg | atg | tat | gag | tat | atg | gct | caa | gcc | tgt | gca | gga | aat | cgt | gtc | agg | 576 |
| Ala | Met | Tyr | Glu | Tyr | Met | Ala | Gln | Ala | Cys | Ala | Gly | Asn | Arg | Val | Arg | |
| | | | 180 | | | | | 185 | | | | | 190 | | | |
| cga | tca | gta | ggt | agc | tca | ttg | tca | tgc | atc | aac | ctg | gat | tgg | gat | gtt | 624 |
| Arg | Ser | Val | Gly | Ser | Ser | Leu | Ser | Cys | Ile | Asn | Leu | Asp | Trp | Asp | Val | |
| | | 195 | | | | | 200 | | | | | 205 | | | | |
| atc | cgt | gat | aaa | act | aaa | act | aag | atc | gaa | tct | ctg | aaa | gaa | cac | ggt | 672 |
| Ile | Arg | Asp | Lys | Thr | Lys | Thr | Lys | Ile | Glu | Ser | Leu | Lys | Glu | His | Gly | |
| | 210 | | | | | 215 | | | | | 220 | | | | | |
| ccg | atc | aaa | aac | aaa | atg | agc | gaa | agc | ccg | aac | aaa | act | gta | tct | gaa | 720 |
| Pro | Ile | Lys | Asn | Lys | Met | Ser | Glu | Ser | Pro | Asn | Lys | Thr | Val | Ser | Glu | |
| 225 | | | | | 230 | | | | | 235 | | | | | 240 | |
| gaa | aaa | gct | aaa | cag | tac | ctg | gaa | gaa | ttc | cac | cag | act | gca | ctg | gaa | 768 |
| Glu | Lys | Ala | Lys | Gln | Tyr | Leu | Glu | Glu | Phe | His | Gln | Thr | Ala | Leu | Glu | |
| | | | | 245 | | | | | 250 | | | | | 255 | | |
| cac | ccg | gaa | ctg | tct | gaa | ctt | aag | acc | gtt | act | ggt | acc | aac | ccg | gta | 816 |

```
                His Pro Glu Leu Ser Glu Leu Lys Thr Val Thr Gly Thr Asn Pro Val
                            260                 265                 270 ttc gct ggt gct aac tac gct gct tgg gca gta aac gtt gct cag gtt   864
                Phe Ala Gly Ala Asn Tyr Ala Ala Trp Ala Val Asn Val Ala Gln Val
                            275                 280                 285 atc gat agc gaa act gct gat aac ctg gaa aaa act acc gcg gct ctg   912
                Ile Asp Ser Glu Thr Ala Asp Asn Leu Glu Lys Thr Thr Ala Ala Leu
                            290                 295                 300 tct atc ctg ccg ggt atc ggt agc gta atg ggc atc gca gac ggc gcc   960
                Ser Ile Leu Pro Gly Ile Gly Ser Val Met Gly Ile Ala Asp Gly Ala
                305                 310                 315                 320 gtt cac cac aac act gaa gaa atc gtt gca cag tct atc gct ctg agc   1008
                Val His His Asn Thr Glu Glu Ile Val Ala Gln Ser Ile Ala Leu Ser
                            325                 330                 335 tct ctg atg gtt gct cag gcc atc ccg ctg gta ggt gaa ctg gtt gat   1056
                Ser Leu Met Val Ala Gln Ala Ile Pro Leu Val Gly Glu Leu Val Asp
                            340                 345                 350 atc ggt ttc gct gca tac aac ttc gtt gaa agc atc atc aac ctg ttc   1104
                Ile Gly Phe Ala Ala Tyr Asn Phe Val Glu Ser Ile Ile Asn Leu Phe
                            355                 360                 365 cag gtt gtt cac aac tct tac aac cgc ccg gct tac tct ccg ggt cac   1152
                Gln Val Val His Asn Ser Tyr Asn Arg Pro Ala Tyr Ser Pro Gly His
                            370                 375                 380 aag acg cat gca                                                    1164
                Lys Thr His Ala
                385

<210> SEQ ID NO 84
                <211> LENGTH: 388
                <212> TYPE: PRT
                <213> ORGANISM: Artificial sequence
                <220> FEATURE:
                <223> OTHER INFORMATION: Corynephage omega: DT387(AD8)

<400> SEQUENCE: 84

Met Gly Ala Asp Asp Val Val Ser Ser Lys Ser Phe Val Met Glu Asn
                1               5                   10                  15

Phe Ser Ser Tyr His Gly Thr Lys Pro Gly Tyr Val Asp Ser Ile Gln
                            20                  25                  30

Lys Gly Ile Gln Lys Pro Lys Ser Gly Thr Gln Gly Asn Tyr Asp Asp
                        35                  40                  45

Asp Trp Lys Gly Phe Tyr Ser Thr Asp Asn Lys Tyr Asp Ala Ala Gly
                    50                  55                  60

Tyr Ser Val Asp Asn Glu Asn Pro Leu Ser Lys Ala Gly Gly Val
                65                  70                  75                  80

Val Lys Val Thr Tyr Pro Gly Leu Thr Lys Val Leu Ala Leu Lys Val
                            85                  90                  95

Asp Asn Ala Glu Thr Ile Lys Lys Glu Leu Gly Leu Ser Leu Thr Glu
                            100                 105                 110

Pro Leu Met Glu Gln Val Gly Thr Glu Glu Phe Ile Lys Arg Phe Gly
                            115                 120                 125

Asp Gly Ala Ser Arg Val Val Leu Ser Leu Pro Phe Ala Glu Gly Ser
                        130                 135                 140

Ser Ser Val Glu Tyr Ile Asn Asn Trp Glu Gln Ala Lys Ala Leu Ser
                145                 150                 155                 160

Val Glu Leu Glu Ile Asn Phe Glu Thr Arg Gly Lys Arg Gly Gln Asp
                            165                 170                 175

Ala Met Tyr Glu Tyr Met Ala Gln Ala Cys Ala Gly Asn Arg Val Arg
                            180                 185                 190
```

```
Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala
385

<210> SEQ ID NO 85
<211> LENGTH: 1179
<212> TYPE: DNA
<213> ORGANISM: Artificial sequence
<220> FEATURE:
<223> OTHER INFORMATION: Corynephage omega: DT380gsC
<220> FEATURE:
<221> NAME/KEY: CDS
<222> LOCATION: (1)..(1179)

<400> SEQUENCE: 85 atg ggc gct gat gat gtt gtt gat tct tct aaa tct ttt gtg atg gaa      48
Met Gly Ala Asp Asp Val Val Asp Ser Ser Lys Ser Phe Val Met Glu
1               5                   10                  15 aac ttt tct tcg tac cac ggg act aaa cct ggt tat gta gat tcc att      96
Asn Phe Ser Ser Tyr His Gly Thr Lys Pro Gly Tyr Val Asp Ser Ile
            20                  25                  30 caa aaa ggt ata caa aag cca aaa tct ggt aca caa gga aat tat gac     144
Gln Lys Gly Ile Gln Lys Pro Lys Ser Gly Thr Gln Gly Asn Tyr Asp
        35                  40                  45 gat gat tgg aaa ggg ttt tat agt acc gac aat aaa tac gac gct gcg     192
Asp Asp Trp Lys Gly Phe Tyr Ser Thr Asp Asn Lys Tyr Asp Ala Ala
    50                  55                  60 gga tac tct gta gat aat gaa aac ccg ctc tct gga aaa gct gga ggc     240
Gly Tyr Ser Val Asp Asn Glu Asn Pro Leu Ser Gly Lys Ala Gly Gly
65                  70                  75                  80 gtg gtc aaa gtg acg tat cca gga ctg acg aag gtt ctc gca cta aaa     288
Val Val Lys Val Thr Tyr Pro Gly Leu Thr Lys Val Leu Ala Leu Lys
                85                  90                  95 gtg gat aat gcc gaa act att aag aaa gag tta ggt tta agt ctc act     336
Val Asp Asn Ala Glu Thr Ile Lys Lys Glu Leu Gly Leu Ser Leu Thr
            100                 105                 110
```

| | | | | | | | | | | | | | | |
|---|---|---|---|---|---|---|---|---|---|---|---|---|---|---|
| gaa | ccg | ttg | atg | gag | caa | gtc | gga | acg | gaa | gag | ttt | atc | aaa | agg | ttc | 384 |
| Glu | Pro | Leu | Met | Glu | Gln | Val | Gly | Thr | Glu | Glu | Phe | Ile | Lys | Arg | Phe |
| | 115 | | | | 120 | | | | | 125 | | | | | | ggt gat ggt gct tcg cgt gta gtg ctc agc ctt ccc ttc gct gag ggg   432
Gly Asp Gly Ala Ser Arg Val Val Leu Ser Leu Pro Phe Ala Glu Gly
          130                 135                 140 agt tct agc gtt gaa tat att aat aac tgg gaa cag gcg aaa gcg tta   480
Ser Ser Ser Val Glu Tyr Ile Asn Asn Trp Glu Gln Ala Lys Ala Leu
145                 150                 155                 160 agc gta gaa ctt gag att aat ttt gaa acc cgt gga aaa cgt ggc caa   528
Ser Val Glu Leu Glu Ile Asn Phe Glu Thr Arg Gly Lys Arg Gly Gln
                165                 170                 175 gat gcg atg tat gag tat atg gct caa gcc tgt gca gga aat cgt gtc   576
Asp Ala Met Tyr Glu Tyr Met Ala Gln Ala Cys Ala Gly Asn Arg Val
            180                 185                 190 agg cga tca gta ggt agc tca ttg tca tgc atc aac ctg gat tgg gat   624
Arg Arg Ser Val Gly Ser Ser Leu Ser Cys Ile Asn Leu Asp Trp Asp
        195                 200                 205 gtt atc cgt gat aaa act aaa act aag atc gaa tct ctg aaa gaa cac   672
Val Ile Arg Asp Lys Thr Lys Thr Lys Ile Glu Ser Leu Lys Glu His
    210                 215                 220 ggt ccg atc aaa aac aaa atg agc gaa agc ccg aac aaa act gta tct   720
Gly Pro Ile Lys Asn Lys Met Ser Glu Ser Pro Asn Lys Thr Val Ser
225                 230                 235                 240 gaa gaa aaa gct aaa cag tac ctg gaa gaa ttc cac cag act gca ctg   768
Glu Glu Lys Ala Lys Gln Tyr Leu Glu Glu Phe His Gln Thr Ala Leu
                245                 250                 255 gaa cac ccg gaa ctg tct gaa ctt aag acc gtt act ggt acc aac ccg   816
Glu His Pro Glu Leu Ser Glu Leu Lys Thr Val Thr Gly Thr Asn Pro
            260                 265                 270 gta ttc gct ggt gct aac tac gct gct tgg gca gta aac gtt gct cag   864
Val Phe Ala Gly Ala Asn Tyr Ala Ala Trp Ala Val Asn Val Ala Gln
        275                 280                 285 gtt atc gat agc gaa act gct gat aac ctg gaa aaa act acc gcg gct   912
Val Ile Asp Ser Glu Thr Ala Asp Asn Leu Glu Lys Thr Thr Ala Ala
    290                 295                 300 ctg tct atc ctg ccg ggt atc ggt agc gta atg ggc atc gca gac ggc   960
Leu Ser Ile Leu Pro Gly Ile Gly Ser Val Met Gly Ile Ala Asp Gly
305                 310                 315                 320 gcc gtt cac cac aac act gaa gaa atc gtt gca cag tct atc gct ctg  1008
Ala Val His His Asn Thr Glu Glu Ile Val Ala Gln Ser Ile Ala Leu
                325                 330                 335 agc tct ctg atg gtt gct cag gcc atc ccg ctg gta ggt gaa ctg gtt  1056
Ser Ser Leu Met Val Ala Gln Ala Ile Pro Leu Val Gly Glu Leu Val
            340                 345                 350 gat atc ggt ttc gct gca tac aac ttc gtt gaa agc atc atc aac ctg  1104
Asp Ile Gly Phe Ala Ala Tyr Asn Phe Val Glu Ser Ile Ile Asn Leu
        355                 360                 365 ttc cag gtt gtt cac aac tct tac aac cgc ccg gcg cat gca tct agc  1152
Phe Gln Val Val His Asn Ser Tyr Asn Arg Pro Ala His Ala Ser Ser
    370                 375                 380 gga ggt ggc tct agc ggt gga ggc tgt                              1179
Gly Gly Gly Ser Ser Gly Gly Gly Cys
385                 390

<210> SEQ ID NO 86
<211> LENGTH: 393
<212> TYPE: PRT
<213> ORGANISM: Artificial sequence
<220> FEATURE:
<223> OTHER INFORMATION: Corynephage omega: DT380gsC

<400> SEQUENCE: 86

| | | | | | | | | | | | | | | |
|---|---|---|---|---|---|---|---|---|---|---|---|---|---|---|
| Met | Gly | Ala | Asp | Asp | Val | Val | Asp | Ser | Ser | Lys | Ser | Phe | Val | Met | Glu |
| 1 | | | | 5 | | | | | 10 | | | | | 15 | |
| Asn | Phe | Ser | Ser | Tyr | His | Gly | Thr | Lys | Pro | Gly | Tyr | Val | Asp | Ser | Ile |
| | | | 20 | | | | | 25 | | | | | 30 | | |
| Gln | Lys | Gly | Ile | Gln | Lys | Pro | Lys | Ser | Gly | Thr | Gln | Gly | Asn | Tyr | Asp |
| | | | 35 | | | | 40 | | | | | 45 | | | |
| Asp | Asp | Trp | Lys | Gly | Phe | Tyr | Ser | Thr | Asp | Asn | Lys | Tyr | Asp | Ala | Ala |
| | 50 | | | | | 55 | | | | | 60 | | | | |
| Gly | Tyr | Ser | Val | Asp | Asn | Glu | Asn | Pro | Leu | Ser | Gly | Lys | Ala | Gly | Gly |
| 65 | | | | | 70 | | | | | 75 | | | | | 80 |
| Val | Val | Lys | Val | Thr | Tyr | Pro | Gly | Leu | Thr | Lys | Val | Leu | Ala | Leu | Lys |
| | | | | 85 | | | | | 90 | | | | | 95 | |
| Val | Asp | Asn | Ala | Glu | Thr | Ile | Lys | Lys | Glu | Leu | Gly | Leu | Ser | Leu | Thr |
| | | | 100 | | | | | 105 | | | | | 110 | | |
| Glu | Pro | Leu | Met | Glu | Gln | Val | Gly | Thr | Glu | Glu | Phe | Ile | Lys | Arg | Phe |
| | | 115 | | | | | 120 | | | | | 125 | | | |
| Gly | Asp | Gly | Ala | Ser | Arg | Val | Val | Leu | Ser | Leu | Pro | Phe | Ala | Glu | Gly |
| | 130 | | | | | 135 | | | | | 140 | | | | |
| Ser | Ser | Ser | Val | Glu | Tyr | Ile | Asn | Asn | Trp | Glu | Gln | Ala | Lys | Ala | Leu |
| 145 | | | | | 150 | | | | | 155 | | | | | 160 |
| Ser | Val | Glu | Leu | Glu | Ile | Asn | Phe | Glu | Thr | Arg | Gly | Lys | Arg | Gly | Gln |
| | | | | 165 | | | | | 170 | | | | | 175 | |
| Asp | Ala | Met | Tyr | Glu | Tyr | Met | Ala | Gln | Ala | Cys | Ala | Gly | Asn | Arg | Val |
| | | | 180 | | | | | 185 | | | | | 190 | | |
| Arg | Arg | Ser | Val | Gly | Ser | Ser | Leu | Ser | Cys | Ile | Asn | Leu | Asp | Trp | Asp |
| | | 195 | | | | | 200 | | | | | 205 | | | |
| Val | Ile | Arg | Asp | Lys | Thr | Lys | Thr | Lys | Ile | Glu | Ser | Leu | Lys | Glu | His |
| | 210 | | | | | 215 | | | | | 220 | | | | |
| Gly | Pro | Ile | Lys | Asn | Lys | Met | Ser | Glu | Ser | Pro | Asn | Lys | Thr | Val | Ser |
| 225 | | | | | 230 | | | | | 235 | | | | | 240 |
| Glu | Glu | Lys | Ala | Lys | Gln | Tyr | Leu | Glu | Glu | Phe | His | Gln | Thr | Ala | Leu |
| | | | | 245 | | | | | 250 | | | | | 255 | |
| Glu | His | Pro | Glu | Leu | Ser | Glu | Leu | Lys | Thr | Val | Thr | Gly | Thr | Asn | Pro |
| | | | 260 | | | | | 265 | | | | | 270 | | |
| Val | Phe | Ala | Gly | Ala | Asn | Tyr | Ala | Ala | Trp | Ala | Val | Asn | Val | Ala | Gln |
| | | 275 | | | | | 280 | | | | | 285 | | | |
| Val | Ile | Asp | Ser | Glu | Thr | Ala | Asp | Asn | Leu | Glu | Lys | Thr | Thr | Ala | Ala |
| | 290 | | | | | 295 | | | | | 300 | | | | |
| Leu | Ser | Ile | Leu | Pro | Gly | Ile | Gly | Ser | Val | Met | Gly | Ile | Ala | Asp | Gly |
| 305 | | | | | 310 | | | | | 315 | | | | | 320 |
| Ala | Val | His | His | Asn | Thr | Glu | Glu | Ile | Val | Ala | Gln | Ser | Ile | Ala | Leu |
| | | | | 325 | | | | | 330 | | | | | 335 | |
| Ser | Ser | Leu | Met | Val | Ala | Gln | Ala | Ile | Pro | Leu | Val | Gly | Glu | Leu | Val |
| | | | 340 | | | | | 345 | | | | | 350 | | |
| Asp | Ile | Gly | Phe | Ala | Ala | Tyr | Asn | Phe | Val | Glu | Ser | Ile | Ile | Asn | Leu |
| | | 355 | | | | | 360 | | | | | 365 | | | |
| Phe | Gln | Val | Val | His | Asn | Ser | Tyr | Asn | Arg | Pro | Ala | His | Ala | Ser | Ser |
| | 370 | | | | | 375 | | | | | 380 | | | | |
| Gly | Gly | Gly | Ser | Ser | Gly | Gly | Cys | | | | | | | | |
| 385 | | | | | 390 | | | | | | | | | | |

<210> SEQ ID NO 87

<211> LENGTH: 522
<212> TYPE: PRT
<213> ORGANISM: Artificial sequence
<220> FEATURE:
<223> OTHER INFORMATION: Corynephage omega: DT387(V7A)IL2

<400> SEQUENCE: 87

```
Met Gly Ala Asp Asp Val Ala Asp Ser Ser Lys Ser Phe Val Met Glu
1               5                   10                  15
Asn Phe Ser Ser Tyr His Gly Thr Lys Pro Gly Tyr Val Asp Ser Ile
            20                  25                  30
Gln Lys Gly Ile Gln Lys Pro Lys Ser Gly Thr Gln Gly Asn Tyr Asp
        35                  40                  45
Asp Asp Trp Lys Gly Phe Tyr Ser Thr Asp Asn Lys Tyr Asp Ala Ala
    50                  55                  60
Gly Tyr Ser Val Asp Asn Glu Asn Pro Leu Ser Gly Lys Ala Gly Gly
65                  70                  75                  80
Val Val Lys Val Thr Tyr Pro Gly Leu Thr Lys Val Leu Ala Leu Lys
                85                  90                  95
Val Asp Asn Ala Glu Thr Ile Lys Lys Glu Leu Gly Leu Ser Leu Thr
            100                 105                 110
Glu Pro Leu Met Glu Gln Val Gly Thr Glu Glu Phe Ile Lys Arg Phe
        115                 120                 125
Gly Asp Gly Ala Ser Arg Val Val Leu Ser Leu Pro Phe Ala Glu Gly
    130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                165                 170                 175
Asp Ala Met Tyr Glu Tyr Met Ala Gln Ala Cys Ala Gly Asn Arg Val
            180                 185                 190
Arg Arg Ser Val Gly Ser Ser Leu Ser Cys Ile Asn Leu Asp Trp Asp
        195                 200                 205
Val Ile Arg Asp Lys Thr Lys Thr Lys Ile Glu Ser Leu Lys Glu His
    210                 215                 220
Gly Pro Ile Lys Asn Lys Met Ser Glu Ser Pro Asn Lys Thr Val Ser
225                 230                 235                 240
Glu Glu Lys Ala Lys Gln Tyr Leu Glu Glu Phe His Gln Thr Ala Leu
                245                 250                 255
Glu His Pro Glu Leu Ser Glu Leu Lys Thr Val Thr Gly Thr Asn Pro
            260                 265                 270
Val Phe Ala Gly Ala Asn Tyr Ala Ala Trp Ala Val Asn Val Ala Gln
        275                 280                 285
Val Ile Asp Ser Glu Thr Ala Asp Asn Leu Glu Lys Thr Thr Ala Ala
    290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
            340                 345                 350
Asp Ile Gly Phe Ala Ala Tyr Asn Phe Val Glu Ser Ile Ile Asn Leu
        355                 360                 365
Phe Gln Val Val His Asn Ser Tyr Asn Arg Pro Ala Tyr Ser Pro Gly
    370                 375                 380
```

-continued

```
His Lys Thr His Ala Pro Thr Ser Ser Thr Lys Thr Gln Leu
385                 390                 395                 400

Gln Leu Glu His Leu Leu Leu Asp Leu Gln Met Ile Leu Asn Gly Ile
            405                 410                 415

Asn Asn Tyr Lys Asn Pro Lys Leu Thr Arg Met Leu Thr Phe Lys Phe
            420                 425                 430

Tyr Met Pro Lys Lys Ala Thr Glu Leu Lys His Leu Leu Gln Cys Leu
            435                 440                 445

Glu Glu Glu Leu Lys Pro Leu Glu Glu Val Leu Asn Leu Ala Gln Ser
            450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
            485                 490                 495

Ala Asp Glu Thr Ala Thr Ile Val Glu Phe Leu Asn Arg Trp Ile Thr
            500                 505                 510

Phe Cys Gln Ser Ile Ile Ser Thr Leu Thr
            515                 520

<210> SEQ ID NO 88
<211> LENGTH: 522
<212> TYPE: PRT
<213> ORGANISM: Artificial sequence
<220> FEATURE:
<223> OTHER INFORMATION: Corynephage omega: DT387(D8S)IL2

<400> SEQUENCE: 88

Met Gly Ala Asp Asp Val Val Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
```

```
                    225                 230                 235                 240
        Glu Glu Lys Ala Lys Gln Tyr Leu Glu Phe His Gln Thr Ala Leu
                        245                 250                 255
        Glu His Pro Glu Leu Ser Glu Leu Lys Thr Val Thr Gly Thr Asn Pro
                    260                 265                 270
        Val Phe Ala Gly Ala Asn Tyr Ala Ala Trp Ala Val Asn Val Ala Gln
                    275                 280                 285
        Val Ile Asp Ser Glu Thr Ala Asp Asn Leu Glu Lys Thr Thr Ala Ala
                    290                 295                 300
        Leu Ser Ile Leu Pro Gly Ile Gly Ser Val Met Gly Ile Ala Asp Gly
        305                 310                 315                 320
        Ala Val His His Asn Thr Glu Glu Ile Val Ala Gln Ser Ile Ala Leu
                        325                 330                 335
        Ser Ser Leu Met Val Ala Gln Ala Ile Pro Leu Val Gly Glu Leu Val
                        340                 345                 350
        Asp Ile Gly Phe Ala Ala Tyr Asn Phe Val Glu Ser Ile Ile Asn Leu
                        355                 360                 365
        Phe Gln Val Val His Asn Ser Tyr Asn Arg Pro Ala Tyr Ser Pro Gly
            370                 375                 380
        His Lys Thr His Ala Pro Thr Ser Ser Thr Lys Lys Thr Gln Leu
        385                 390                 395                 400
        Gln Leu Glu His Leu Leu Leu Asp Leu Gln Met Ile Leu Asn Gly Ile
                        405                 410                 415
        Asn Asn Tyr Lys Asn Pro Lys Leu Thr Arg Met Leu Thr Phe Lys Phe
                        420                 425                 430
        Tyr Met Pro Lys Lys Ala Thr Glu Leu Lys His Leu Leu Gln Cys Leu
                        435                 440                 445
        Glu Glu Glu Leu Lys Pro Leu Glu Glu Val Leu Asn Leu Ala Gln Ser
                    450                 455                 460
        Lys Asn Phe His Leu Arg Pro Arg Asp Leu Ile Ser Asn Ile Asn Val
        465                 470                 475                 480
        Ile Val Leu Glu Leu Lys Gly Ser Glu Thr Thr Phe Met Cys Glu Tyr
                        485                 490                 495
        Ala Asp Glu Thr Ala Thr Ile Val Glu Phe Leu Asn Arg Trp Ile Thr
                    500                 505                 510
        Phe Cys Gln Ser Ile Ile Ser Thr Leu Thr
                    515                 520

<210> SEQ ID NO 89
<211> LENGTH: 522
<212> TYPE: PRT
<213> ORGANISM: Artificial sequence
<220> FEATURE:
<223> OTHER INFORMATION: Corynephage omega: DT387(D8E)IL2

<400> SEQUENCE: 89

Met Gly Ala Asp Asp Val Val Glu Ser Ser Lys Ser Phe Val Met Glu
1               5                   10                  15

Asn Phe Ser Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr As

```
Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Phe Ile Lys Arg Phe
            115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
            420                 425                 430

Tyr Met Pro Lys Lys Ala Thr Glu Leu Lys His Leu Leu Gln Cys Leu
        435                 440                 445

Glu Glu Glu Leu Lys Pro Leu Glu Val Leu Asn Leu Ala Gln Ser
450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
```

```
                   500             505             510
Phe Cys Gln Ser Ile Ile Ser Thr Leu Thr
            515                 520

<210> SEQ ID NO 90
<211> LENGTH: 522
<212> TYPE: PRT
<213> ORGANISM: Artificial sequence
<220> FEATURE:
<223> OTHER INFORMATION: Corynephage omega: DT387(V29A)IL2

<400> SEQUENCE: 90

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn

```
Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
    370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
            420                 425                 430

Tyr Met Pro Lys Lys Ala Thr Glu Leu Lys His Leu Leu Gln Cys Leu
        435                 440                 445

Glu Glu Glu Leu Lys Pro Leu Glu Glu Val Leu Asn Leu Ala Gln Ser
450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
                500                 505                 510

Phe Cys Gln Ser Ile Ile Ser Thr Leu Thr
            515                 520

<210> SEQ ID NO 91
<211> LENGTH: 522
<212> TYPE: PRT
<213> ORGANISM: Artificial sequence
<220> FEATURE:
<223> OTHER INFORMATION: Corynephage omega: DT387(I290A)IL2

<400> SEQUENCE: 91

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys T

```
Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
        210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ala Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr His Ala Pro Thr Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
            420                 425                 430

Tyr Met Pro Lys Lys Ala Thr Glu Leu Lys His Leu Leu Gln Cys Leu
        435                 440                 445

Glu Glu Glu Leu Lys Pro Leu Glu Glu Val Leu Asn Leu Ala Gln Ser
450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
            500                 505                 510

Phe Cys Gln Ser Ile Ile Ser Thr Leu Thr
        515                 520

<210> SEQ ID NO 92
<211> LENGTH: 522
<212> TYPE: PRT
<213> ORGANISM: Artificial sequence
<220> FEATURE:
<223> OTHER INFORMATION: Corynephage omega: DT387(D291E)IL2

<400> SEQUENCE: 92

Met Gly Ala Asp Asp Val Val Asp Ser Ser Lys Ser Phe Val Met Glu
1               5                   10                  15

Asn Phe Ser Ser Tyr His Gly Thr Lys Pro G

-continued

```
                 35                  40                  45
Asp Asp Trp Lys Gly Phe Tyr Ser Thr Asp Asn Lys Tyr Asp Ala Ala
 50                  55                  60
Gly Tyr Ser Val Asp Asn Glu Asn Pro Leu Ser Gly Lys Ala Gly Gly
 65                  70                  75                  80
Val Val Lys Val Thr Tyr Pro Gly Leu Thr Lys Val Leu Ala Leu Lys
                 85                  90                  95
Val Asp Asn Ala Glu Thr Ile Lys Lys Glu Leu Gly Leu Ser Leu Thr
                100                 105                 110
Glu Pro Leu Met Glu Gln Val Gly Thr Glu Glu Phe Ile Lys Arg Phe
                115                 120                 125
Gly Asp Gly Ala Ser Arg Val Val Leu Ser Leu Pro Phe Ala Glu Gly
                130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                165                 170                 175
Asp Ala Met Tyr Glu Tyr Met Ala Gln Ala Cys Ala Gly Asn Arg Val
                180                 185                 190
Arg Arg Ser Val Gly Ser Ser Leu Ser Cys Ile Asn Leu Asp Trp Asp
                195                 200                 205
Val Ile Arg Asp Lys Thr Lys Thr Lys Ile Glu Ser Leu Lys Glu His
                210                 215                 220
Gly Pro Ile Lys Asn Lys Met Ser Glu Ser Pro Asn Lys Thr Val Ser
225                 230                 235                 240
Glu Glu Lys Ala Lys Gln Tyr Leu Glu Glu Phe His Gln Thr Ala Leu
                245                 250                 255
Glu His Pro Glu Leu Ser Glu Leu Lys Thr Val Thr Gly Thr Asn Pro
                260                 265                 270
Val Phe Ala Gly Ala Asn Tyr Ala Ala Trp Ala Val Asn Val Ala Gln
                275                 280                 285
Val Ile Glu Ser Glu Thr Ala Asp Asn Leu Glu Lys Thr Thr Ala Ala
                290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
                340                 345                 350
Asp Ile Gly Phe Ala Ala Tyr Asn Phe Val Glu Ser Ile Ile Asn Leu
                355                 360                 365
Phe Gln Val Val His Asn Ser Tyr Asn Arg Pro Ala Tyr Ser Pro Gly
    370                 375                 380
His Lys Thr His Ala Pro Thr Ser Ser Ser Thr Lys Lys Thr Gln Leu
385                 390                 395                 400
Gln Leu Glu His Leu Leu Leu Asp Leu Gln Met Ile Leu Asn Gly Ile
                405                 410                 415
Asn Asn Tyr Lys Asn Pro Lys Leu Thr Arg Met Leu Thr Phe Lys Phe
                420                 425                 430
Tyr Met Pro Lys Lys Ala Thr Glu Leu Lys His Leu Leu Gln Cys Leu
                435                 440                 445
Glu Glu Glu Leu Lys Pro Leu Glu Glu Val Leu Asn Leu Ala Gln Ser
450                 455                 460
```

```
Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
            500                 505                 510

Phe Cys Gln Ser Ile Ile Ser Thr Leu Thr
        515                 520
```

<210> SEQ ID NO 93
<211> LENGTH: 522
<212> TYPE: PRT
<213> ORGANISM: Artificial sequence
<220> FEATURE:
<223> OTHER INFORMATION: Corynephage omega: DT387(V7AV29A)IL2

<400> SEQUENCE: 93

```
Met Gly Ala Asp Asp Val Ala Asp Ser Lys Ser Phe Val Met Glu
1               5                   10                  15

Asn Phe Ser Ser Tyr His Gly Thr Lys Pro Gly Tyr Ala Asp Ser Ile
                20                  25                  30

Gln Lys Gly Ile Gln Lys Pro Lys Ser Gly Thr Gln Gly Asn T

```
305                 310                 315                 320
Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
            370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
                420                 425                 430

Tyr Met Pro Lys Lys Ala Thr Glu Leu Lys His Leu Leu Gln Cys Leu
            435                 440                 445

Glu Glu Glu Leu Lys Pro Leu Glu Glu Val Leu Asn Leu Ala Gln Ser
450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
                500                 505                 510

Phe Cys Gln Ser Ile Ile Ser Thr Leu Thr
            515                 520

<210> SEQ ID NO 94
<211> LENGTH: 522
<212> TYPE: PRT
<213> ORGANISM: Artificial sequence
<220> FEATURE:
<223> OTHER INFORMATION: Corynephage omega: DT387(V7AV29AD291E)IL2

<400> SEQUENCE: 94

Met Gly Ala Asp Asp Val Ala Asp Ser Ser Lys Ser Phe Val Met Glu
1               5                   10                  15

Asn Phe Ser Ser Tyr His Gly Thr Lys Pro Gly Tyr Ala Asp Ser Ile
                20                  25                  30

Gln L

Ser Val Glu Leu Glu Ile Asn Phe Thr Arg Gly Lys Arg Gly Gln
            165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
            195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
            245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
            275                 280                 285

Val Ile Glu Ser Glu Thr Ala Asp Asn Leu Glu Lys Thr Thr Ala Ala
            290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
            325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
            370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
            405                 410                 415

Asn Asn Tyr Lys Asn Pro Lys Leu Thr Arg Met Leu Thr Phe Lys Phe
            420                 425                 430

Tyr Met Pro Lys Lys Ala Thr Glu Leu Lys His Leu Leu Gln Cys Leu
            435                 440                 445

Glu Glu Glu Leu Lys Pro Leu Glu Glu Val Leu Asn Leu Ala Gln Ser
            450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
            485                 490                 495

Ala Asp Glu Thr Ala Thr Ile Val Glu Phe Leu Asn Arg Trp Ile Thr
            500                 505                 510

Phe Cys Gln Ser Ile Ile Ser Thr Leu Thr
            515                 520

<210> SEQ ID NO 95
<211> LENGTH: 522
<212> TYPE: PRT
<213> ORGANISM: Artificial sequence
<220> FEATURE:
<223> OTHER INFORMATION: Corynephage omega: DT387(D8SV29A)IL2

<400> SEQUENCE: 95

```
Met Gly Ala Asp Asp Val Val Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
                35                  40                  45

Asp Asp Trp Lys Gly Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
                115                 120                 125

Gly Asp Gly Ala Ser Arg Val Val Leu Ser Leu Pro Phe Ala Glu Gly
        130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
                195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
            420                 425                 430
```

Tyr Met Pro Lys Lys Ala Thr Glu Leu Lys His Leu Leu Gln Cys Leu
            435                 440                 445

Glu Glu Glu Leu Lys Pro Leu Glu Glu Val Leu Asn Leu Ala Gln Ser
        450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
            500                 505                 510

Phe Cys Gln Ser Ile Ile Ser Thr Leu Thr
            515                 520

<210> SEQ ID NO 96
<211> LENGTH: 522
<212> TYPE: PRT
<213> ORGANISM: Artificial sequence
<220> FEATURE:
<223> OTHER INFORMATION: Corynephage omega: DT387(V7SV29A)IL2

<400> SEQUENCE: 96

Met Gly Ala Asp Asp Val Ser Asp Ser Ser Lys Ser Phe Val Met Glu
1               5                   10                  15

Asn Phe Ser Ser Tyr His Gly Thr Lys Pro Gly Tyr Ala Asp Ser Ile
                20                  25                  30

Gln Lys G

```
Val Phe Ala Gly Ala Asn Tyr Ala Ala Trp Ala Val Asn Val Ala Gln
    275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
    370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
            420                 425                 430

Tyr Met Pro Lys Lys Ala Thr Glu Leu Lys His Leu Leu Gln Cys Leu
                435                 440                 445

Glu Glu Glu Leu Lys Pro Leu Glu Glu Val Leu Asn Leu Ala Gln Ser
    450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
            500                 505                 510

Phe Cys Gln Ser Ile Ile Ser Thr Leu Thr
    515                 520

<210> SEQ ID NO 97
<211> LENGTH: 522
<212> TYPE: PRT
<213> ORGANISM: Artificial sequence
<220> FEATURE:
<223> OTHER INFORMATION: Corynephage omega: DT387(D8EV29A)IL2

<400> SEQUENCE: 97

Met Gly Ala Asp Asp Val Val Glu Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly

```
                115                 120                 125
Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
                180                 185                 190

Arg Arg Ser Val Gly Ser Ser Leu Ser Cys Ile Asn Leu Asp Trp Asp
                195                 200                 205

Val Ile Arg Asp Lys Thr Lys Thr Lys Ile Glu Ser Leu Lys Glu His
                210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
                260                 265                 270

Val Phe Ala Gly Ala Asn Tyr Ala Ala Trp Ala Val Asn Val Ala Gln
                275                 280                 285

Val Ile Asp Ser Glu Thr Ala Asp Asn Leu Glu Lys Thr Thr Ala Ala
                290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
                420                 425                 430

Tyr Met Pro Lys Lys Ala Thr Glu Leu Lys His Leu Leu Gln Cys Leu
                435                 440                 445

Glu Glu Glu Leu Lys Pro Leu Glu Glu Val Leu Asn Leu Ala Gln Ser
                450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
                500                 505                 510

Phe Cys Gln Ser Ile Ile Ser Thr Leu Thr
                515                 520
```

<210> SEQ ID NO 98
<211> LENGTH: 522

<212> TYPE: PRT
<213> ORGANISM: Artificial sequence
<220> FEATURE:
<223> OTHER INFORMATION: Corynephage omega: DAB389(V7AV29AI290A)IL2

<400> SEQUENCE: 98

```
Met Gly Ala Asp Asp Val Ala Asp Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Ph

```
                385                 390                 395                 400
Gln Leu Glu His Leu Leu Asp Leu Gln Met Ile Leu Asn Gly Ile
                    405                 410                 415

Asn Asn Tyr Lys Asn Pro Lys Leu Thr Arg Met Leu Thr Phe Lys Phe
                420                 425                 430

Tyr Met Pro Lys Lys Ala Thr Glu Leu Lys His Leu Leu Gln Cys Leu
            435                 440                 445

Glu Glu Glu Leu Lys Pro Leu Glu Glu Val Leu Asn Leu Ala Gln Ser
        450                 455                 460

Lys Asn Phe His Leu Arg Pro Arg Asp Leu Ile Ser Asn Ile Asn Val
465                 470                 475                 480

Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
            500                 505                 510

Phe Cys Gln Ser Ile Ile Ser Thr Leu Thr
            515                 520

<210> SEQ ID NO 99
<211> LENGTH: 442
<212> TYPE: PRT
<213> ORGANISM: Artificial sequence
<220> FEATURE:
<223> OTHER INFORMATION: Corynephage omega: DT387(V29A)EGF

<400> SEQUENCE: 99

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Ala Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Ph

Glu Glu Lys Ala Lys Gln Tyr Leu Glu Phe His Gln Thr Ala Leu
            245                 250                 255

Glu His Pro Glu Leu Ser Glu Leu Lys Thr Val Thr Gly Thr Asn Pro
        260                 265                 270

Val Phe Ala Gly Ala Asn Tyr Ala Ala Trp Ala Val Asn Val Ala Gln
            275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
        370                 375                 380

His Lys Thr His Ala Asn Ser Asp Ser Glu Cys Pro Leu Ser His Asp
385                 390                 395                 400

Gly Tyr Cys Leu His Asp Gly Val Cys Met Tyr Ile Glu Ala Leu Asp
                405                 410                 415

Lys Tyr Ala Cys Asn Cys Val Val Gly Tyr Ile Gly Glu Arg Cys Gln
            420                 425                 430

Tyr Arg Asp Leu Lys Trp Trp Glu Leu Arg
            435                 440

<210> SEQ ID NO 100
<211> LENGTH: 442
<212> TYPE: PRT
<213> ORGANISM: Artificial sequence
<220> FEATURE:
<223> OTHER INFORMATION: Corynephage omega: DT387(D291E)EGF

<400> SEQUENCE: 100

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp As

```
Ser Val Glu Leu Glu Ile Asn Phe Glu Thr Arg Gly Lys Arg Gly Gln
            165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
            195                 200                 205

Val Ile Arg Asp Lys Thr Lys Thr Lys Ile Glu Ser Leu Lys Glu His
            210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
            245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
            275                 280                 285

Val Ile Glu Ser Glu Thr Ala Asp Asn Leu Glu Lys Thr Thr Ala Ala
            290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
            325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
            370                 375                 380

His Lys Thr His Ala Asn Ser Asp Ser Glu Cys Pro Leu Ser His Asp
385                 390                 395                 400

Gly Tyr Cys Leu His Asp Gly Val Cys Met Tyr Ile Glu Ala Leu Asp
            405                 410                 415

Lys Tyr Ala Cys Asn Cys Val Val Gly Tyr Ile Gly Glu Arg Cys Gln
            420                 425                 430

Tyr Arg Asp Leu Lys Trp Trp Glu Leu Arg
            435                 440

<210> SEQ ID NO 101
<211> LENGTH: 442
<212> TYPE: PRT
<213> ORGANISM: Artificial sequence
<220> FEATURE:
<223> OTHER INFORMATION: Corynephage omega: DT387(D8EV29A)EGF

<400> SEQUENCE: 101

Met Gly Ala Asp Asp Val Val Glu Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
```

```
                    85                  90                  95
Val Asp Asn Ala Glu Thr Ile Lys Lys Glu Leu Gly Leu Ser Leu Thr
                100                 105                 110

Glu Pro Leu Met Glu Gln Val Gly Thr Glu Glu Phe Ile Lys Arg Phe
            115                 120                 125

Gly Asp Gly Ala Ser Arg Val Leu Ser Leu Pro Phe Ala Glu Gly
        130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr His Ala Asn Ser Asp Ser Glu Cys Pro Leu Ser His Asp
385                 390                 395                 400

Gly Tyr Cys Leu His Asp Gly Val Cys Met Tyr Ile Glu Ala Leu Asp
                405                 410                 415

Lys Tyr Ala Cys Asn Cys Val Val Gly Tyr Ile Gly Glu Arg Cys Gln
            420                 425                 430

Tyr Arg Asp Leu Lys Trp Trp Glu Leu Arg
        435                 440

<210> SEQ ID NO 102
<211> LENGTH: 442
<212> TYPE: PRT
<213> ORGANISM: Artificial sequence
<220> FEATURE:
<223> OTHER INFORMATION: Corynephage omega: DT387(V7SV29A)EGF

<400> SEQUENCE: 102

Met Gly Ala Asp Asp Val Ser Asp Ser Ser Lys Ser Phe Val Met Glu
1               5                   10                  15
```

```
Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
50                      55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
            115                 120                 125

Gly Asp Gly Ala Ser Arg Val Val Leu Ser Leu Pro Phe Ala Glu Gly
            130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
            275                 280                 285

Val Ile Asp Ser Glu Thr Ala Asp Asn Leu Glu Lys Thr Thr Ala Ala
            290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
            370                 375                 380

His Lys Thr His Ala Asn Ser Asp Ser Glu Cys Pro Leu Ser His Asp
385                 390                 395                 400

Gly Tyr Cys Leu His Asp Gly Val Cys Met Tyr Ile Glu Ala Leu Asp
                405                 410                 415

Lys Tyr Ala Cys Asn Cys Val Val Gly Tyr Ile Gly Glu Arg Cys Gln
            420                 425                 430

Tyr Arg Asp Leu Lys Trp Trp Glu Leu Arg
```

<210> SEQ ID NO 103
<211> LENGTH: 442
<212> TYPE: PRT
<213> ORGANISM: Artificial sequence
<220> FEATURE:
<223> OTHER INFORMATION: Corynephage omegaa: DT387(V7AV29A)EGF

<400> SEQUENCE: 103

| | | | | | | | | | | | | | | |
|---|---|---|---|---|---|---|---|---|---|---|---|---|---|---|
| Met | Gly | Ala | Asp | Asp | Val | Ala | Asp | Ser | Ser | Lys | Ser | Phe | Val | Met | Glu |
| 1 | | | | 5 | | | | | 10 | | | | | 15 | |
| Asn | Phe | Ser | Ser | Tyr | His | Gly | Thr | Lys | Pro | Gly | Tyr | Ala | Asp | Ser | Ile |
| | | | 20 | | | | | 25 | | | | | 30 | | |
| Gln | Lys | Gly | Ile | Gln | Lys | Pro | Lys | Ser | Gly | Thr | Gln | Gly | Asn | Tyr | Asp |
| | | 35 | | | | | 40 | | | | | 45 | | | |
| Asp | Asp | Trp | Lys | Gly | Phe | Tyr | Ser | Thr | Asp | Asn | Lys | Tyr | Asp | Ala | Ala |
| | 50 | | | | | 55 | | | | | 60 | | | | |
| Gly | Tyr | Ser | Val | Asp | Asn | Glu | Asn | Pro | Leu | Ser | Gly | Lys | Ala | Gly | Gly |
| 65 | | | | | 70 | | | | | 75 | | | | | 80 |
| Val | Val | Lys | Val | Thr | Tyr | Pro | Gly | Leu | Thr | Lys | Val | Leu | Ala | Leu | Lys |
| | | | | 85 | | | | | 90 | | | | | 95 | |
| Val | Asp | Asn | Ala | Glu | Thr | Ile | Lys | Lys | Glu | Leu | Gly | Leu | Ser | Leu | Thr |
| | | | 100 | | | | | 105 | | | | | 110 | | |
| Glu | Pro | Leu | Met | Glu | Gln | Val | Gly | Thr | Glu | Glu | Phe | Ile | Lys | Arg | Phe |
| | | 115 | | | | | 120 | | | | | 125 | | | |
| Gly | Asp | Gly | Ala | Ser | Arg | Val | Val | Leu | Ser | Leu | Pro | Phe | Ala | Glu | Gly |
| | 130 | | | | | 135 | | | | | 140 | | | | |
| Ser | Ser | Ser | Val | Glu | Tyr | Ile | Asn | Asn | Trp | Glu | Gln | Ala | Lys | Ala | Leu |
| 145 | | | | | 150 | | | | | 155 | | | | | 160 |
| Ser | Val | Glu | Leu | Glu | Ile | Asn | Phe | Glu | Thr | Arg | Gly | Lys | Arg | Gly | Gln |
| | | | | 165 | | | | | 170 | | | | | 175 | |
| Asp | Ala | Met | Tyr | Glu | Tyr | Met | Ala | Gln | Ala | Cys | Ala | Gly | Asn | Arg | Val |
| | | | 180 | | | | | 185 | | | | | 190 | | |
| Arg | Arg | Ser | Val | Gly | Ser | Ser | Leu | Ser | Cys | Ile | Asn | Leu | Asp | Trp | Asp |
| | | 195 | | | | | 200 | | | | | 205 | | | |
| Val | Ile | Arg | Asp | Lys | Thr | Lys | Thr | Lys | Ile | Glu | Ser | Leu | Lys | Glu | His |
| | 210 | | | | | 215 | | | | | 220 | | | | |
| Gly | Pro | Ile | Lys | Asn | Lys | Met | Ser | Glu | Ser | Pro | Asn | Lys | Thr | Val | Ser |
| 225 | | | | | 230 | | | | | 235 | | | | | 240 |
| Glu | Glu | Lys | Ala | Lys | Gln | Tyr | Leu | Glu | Glu | Phe | His | Gln | Thr | Ala | Leu |
| | | | | 245 | | | | | 250 | | | | | 255 | |
| Glu | His | Pro | Glu | Leu | Ser | Glu | Leu | Lys | Thr | Val | Thr | Gly | Thr | Asn | Pro |
| | | | 260 | | | | | 265 | | | | | 270 | | |
| Val | Phe | Ala | Gly | Ala | Asn | Tyr | Ala | Ala | Trp | Ala | Val | Asn | Val | Ala | Gln |
| | | 275 | | | | | 280 | | | | | 285 | | | |
| Val | Ile | Asp | Ser | Glu | Thr | Ala | Asp | Asn | Leu | Glu | Lys | Thr | Thr | Ala | Ala |
| | 290 | | | | | 295 | | | | | 300 | | | | |
| Leu | Ser | Ile | Leu | Pro | Gly | Ile | Gly | Ser | Val | Met | Gly | Ile | Ala | Asp | Gly |
| 305 | | | | | 310 | | | | | 315 | | | | | 320 |
| Ala | Val | His | His | Asn | Thr | Glu | Glu | Ile | Val | Ala | Gln | Ser | Ile | Ala | Leu |
| | | | | 325 | | | | | 330 | | | | | 335 | |
| Ser | Ser | Leu | Met | Val | Ala | Gln | Ala | Ile | Pro | Leu | Val | Gly | Glu | Leu | Val |
| | | | 340 | | | | | 345 | | | | | 350 | | |
| Asp | Ile | Gly | Phe | Ala | Ala | Tyr | Asn | Phe | Val | Glu | Ser | Ile | Ile | Asn | Leu |
| | | 355 | | | | | 360 | | | | | 365 | | | |

```
Phe Gln Val Val His Asn Ser Tyr Asn Arg Pro Ala Tyr Ser Pro Gly
    370                 375                 380

His Lys Thr His Ala Asn Ser Asp Ser Glu Cys Pro Leu Ser His Asp
385                 390                 395                 400

Gly Tyr Cys Leu His Asp Gly Val Cys Met Tyr Ile Glu Ala Leu Asp
                405                 410                 415

Lys Tyr Ala Cys Asn Cys Val Val Gly Tyr Ile Gly Arg Cys Gln
                420                 425                 430

Tyr Arg Asp Leu Lys Trp Trp Glu Leu Arg
            435                 440

<210> SEQ ID NO 104
<211> LENGTH: 442
<212> TYPE: PRT
<213> ORGANISM: Artificial sequence
<220> FEATURE:
<223> OTHER INFORMATION: Corynephage omega: DT387(D8EV29AD291E)EGF

<400> SEQUENCE: 104

Met Gly Ala Asp Asp Val Ala Glu Ser Ser Lys Ser Phe Val Met Glu
1               5                   10                  15

Asn Phe Ser Ser Tyr His Gly Thr Lys Pro Gly Tyr Ala Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Gly Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285
```

```
Val Ile Glu Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr His Ala Asn Ser Asp Ser Glu Cys Pro Leu Ser His Asp
385                 390                 395                 400

Gly Tyr Cys Leu His Asp Gly Val Cys Met Tyr Ile Glu Ala Leu Asp
                405                 410                 415

Lys Tyr Ala Cys Asn Cys Val Val Gly Tyr Ile Gly Glu Arg Cys Gln
            420                 425                 430

Tyr Arg Asp Leu Lys Trp Trp Glu Leu Arg
        435                 440
```

<210> SEQ ID NO 105
<211> LENGTH: 442
<212> TYPE: PRT
<213> ORGANISM: Artificial sequence
<220> FEATURE:
<223> OTHER INFORMATION: Corynephage omega: DT387(D8SV29A)EGF

<400> SEQUENCE: 105

```
Met Gly Ala Asp Asp Val Val Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
```

-continued

```
                210                 215                 220
Gly Pro Ile Lys Asn Lys Met Ser Glu Ser Pro Asn Lys Thr Val Ser
225                 230                 235                 240

Glu Glu Lys Ala Lys Gln Tyr Leu Glu Phe His Gln Thr Ala Leu
                245                 250                 255

Glu His Pro Glu Leu Ser Glu Leu Lys Thr Val Thr Gly Thr Asn Pro
                260                 265                 270

Val Phe Ala Gly Ala Asn Tyr Ala Ala Trp Ala Val Asn Val Ala Gln
                275                 280                 285

Val Ile Asp Ser Glu Thr Ala Asp Asn Leu Glu Lys Thr Thr Ala Ala
                290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
                370                 375                 380

His Lys Thr His Ala Asn Ser Asp Ser Glu Cys Pro Leu Ser His Asp
385                 390                 395                 400

Gly Tyr Cys Leu His Asp Gly Val Cys Met Tyr Ile Glu Ala Leu Asp
                405                 410                 415

Lys Tyr Ala Cys Asn Cys Val Val Gly Tyr Ile Gly Glu Arg Cys Gln
                420                 425                 430

Tyr Arg Asp Leu Lys Trp Trp Glu Leu Arg
                435                 440

<210> SEQ ID NO 106
<211> LENGTH: 25
<212> TYPE: PRT
<213> ORGANISM: Artificial sequence
<220> FEATURE:
<223> OTHER INFORMATION: Synthetic construct: Signal sequence

<400> SEQUENCE: 106

Met Ser Arg Lys Leu Phe Ala Ser Ile Leu Ile Gly Ala Leu Leu Gly
1               5                   10                  15

Ile Gly Ala Pro Pro Ser Ala His Ala
                20                  25

<210> SEQ ID NO 107
<211> LENGTH: 536
<212> TYPE: PRT
<213> ORGANISM: Artificial sequence
<220> FEATURE:
<223> OTHER INFORMATION: Corynephage omega: Native DT with inserted
      initiator met

<400> SEQUENCE: 107

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
        35                  40                  45
```

```
Asp Asp Trp Lys Gly Phe Tyr Ser Thr Asp Asn Lys Tyr Asp Ala Ala
 50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
                100                 105                 110

Glu Pro Leu Met Glu Gln Val Gly Thr Glu Phe Ile Lys Arg Phe
                115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
                180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
        210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
                260                 265                 270

Val Phe Ala Gly Ala Asn Tyr Ala Ala Trp Ala Val Asn Val Ala Gln
                275                 280                 285

Val Ile Asp Ser Glu Thr Ala Asp Asn Leu Glu Lys Thr Thr Ala Ala
                290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
                420                 425                 430

Val Leu Leu Pro Thr Ile Pro Gly Lys Leu Asp Val Asn Lys Ser Lys
                435                 440                 445

Thr His Ile Ser Val Asn Gly Arg Lys Ile Arg Met Arg Cys Arg Ala
                450                 455                 460

Ile Asp Gly Asp Val Thr Phe Cys Arg Pro Lys Ser Pro Val Tyr Val
465                 470                 475                 480
```

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
                500                 505                 510

Leu Gly Tyr Gln Lys Thr Val Asp His Thr Lys Val Asn Ser Lys Leu
            515                 520                 525

Ser Leu Phe Phe Glu Ile Lys Ser
    530                 535

<210> SEQ ID NO 108
<211> LENGTH: 1881
<212> TYPE: DNA
<213> ORGANISM: Artificial sequence
<220> FEATURE:
<223> OTHER INFORMATION: Corynephage omega: Trucked Native DT sequence

<400> SEQUENCE: 108
aagcttagct agctttcccc atgtaaccaa tctatcaaaa aagggcattg atttcagagc      60
acccttataa ttaggatagc tttacctaat tattttatga gtcctggtaa ggggatacgt     120
tgtgagcaga aaactgtttg cgtcaatctt aataggggcg ctactgggga tagggggcccc   180
accttcagcc catgcaggcg ctgatgatgt tgttgattct tctaaatctt ttgtgatgga    240
aaacttttct tcgtaccacg ggactaaacc tggttatgta gattccattc aaaaaggtat    300
acaaaagcca aaatctggta cacaaggaaa ttatgacgat gattggaaag gttttatag    360
taccgacaat aaatacgacg ctgcgggata ctctgtagat aatgaaaacc cgctctctgg    420
aaaagctgga ggcgtggtca agtgacgta tccaggactg acgaaggttc tcgcactaaa    480
agtggataat gccgaaacta ttaagaaaga gttaggttta agtctcactg aaccgttgat    540
ggagcaagtc ggaacggaag agtttatcaa aaggttcggt gatggtgctt cgcgtgtagt    600
gctcagcctt cccttcgctg aggggagttc tagcgttgaa tatattaata actgggaaca    660
ggcgaaagcg ttaagcgtag aacttgagat taattttgaa acccgtggaa aacgtggcca    720
agatgcgatg tatgagtata tggctcaagc ctgtgcagga atcgtgtca ggcgatcagt    780
aggtagctca ttgtcatgca taaatcttga ttgggatgtc ataagggata aaactaagac    840
aaagatagag tctttgaaag agcatggccc tatcaaaaat aaaatgagcg aaagtcccaa    900
taaaacagta tctgaggaaa aagctaaaca atacctagaa gaatttcatc aaacggcatt    960
agagcatcct gaattgtcag aacttaaaac cgttactggg accaatcctg tattcgctgg   1020
ggctaactat gcggcgtggg cagtaaacgt tgcgcaagtt atcgatagcg aaacagctga   1080
taatttggaa aagacaactg ctgctctttc gatacttcct ggtatcggta gcgtaatggg   1140
cattgcagac ggtgccgttc accacaatac agaagagata gtggcacaat caatagcttt   1200
atcgtcttta atggttgctc aagctattcc attggtagga gagctagttg atattggttt   1260
cgctgcatat aattttgtag agagtattat caatttattt caagtagttc ataattcgta   1320
taatcgtccc gcgtattctc cggggcataa aacgcaacca tttcttcatg acgggtatgc   1380
tgtcagttgg aacactgttg aagattcgat aatccgaact ggttttcaag gggagagtgg   1440
gcacgacata aaaattactg ctgaaaatac cccgcttcca atcgcgggtg tcctactacc   1500
gactattcct ggaagctgg acgttaataa gtccaagact catatttccg taaatggtcg   1560
gaaaataagg atgcgttgca gagctataga cggtgatgta acttttttgtc gccctaaatc   1620
tcctgtttta gttggtaatg gtgtgcatgc gaatcttcac gtggcatttc acagaagcag   1680
ctcggagaaa attcattcta atgaaatttc gtcggattcc ataggcgttc ttgggtacca   1740

```
gaaaacagta gatcacacca aggttaattc taagctatcg ctattttttg aaatcaaaag   1800
ctgaaaggta gtggggtcgt gtgctggtaa gccgaacggt tccggaatgg cgctatagta   1860
tgcacaggta gagcagaatt c                                              1881
```

```
<210> SEQ ID NO 109
<211> LENGTH: 108
<212> TYPE: DNA
<213> ORGANISM: Artificial sequence
<220> FEATURE:
<223> OTHER INFORMATION: Synthetic construct: changes in various DT
      variants
<220> FEATURE:
<221> NAME/KEY: CDS
<222> LOCATION: (1)..(108)

<400> SEQUENCE: 109 atg ggc gct gat gat gtt gtt gat tct tct aaa tct ttt gtg atg gaa    48
Met Gly Ala Asp Asp Val Val Asp Ser Ser Lys Ser Phe Val Met Glu
1               5                   10                  15 aac

```
<210> SEQ ID NO 112
<211> LENGTH: 36
<212> TYPE: PRT
<213> ORGANISM: Artificial sequence
<220> FEATURE:
<223> OTHER INFORMATION: Synthetic construct: changes in various DT
      variants

<400> SEQUENCE: 112

Met Gly Ala Asp Asp Val Ala Ser Ser Lys Ser Phe Val Met Glu
1               5                   10                  15

Asn Phe Ser Ser Tyr His Gly Thr Lys Pro Gly Tyr Ala Asp Ser Ile
            20                  25                  30

Gln Lys Gly Ile
        35

<210> SEQ ID NO 113
<211> LENGTH: 108
<212> TYPE: DNA
<213> ORGANISM: Artificial sequence
<220> FEATURE:
<223> OTHER INFORMATION: Synthetic Construct: changes in various DT
      variants
<220> FEATURE:
<221> NAME/KEY: CDS
<222> LOCATION: (1)..(108)

<400> SEQUENCE: 113 atg ggc gct gat gat gtt tct gaa tct tct aaa tct ttt gtg atg gaa      48
Met Gly Ala Asp Asp Val Ser Glu Ser Ser Lys Ser Phe Val Met Glu
1               5                   10                  15 aac ttt tct tcg tac cac ggg act aaa cct ggt tat gta gat tcc att      96
Asn Phe Ser Ser Tyr His Gly Thr Lys Pro Gly Tyr Val Asp Ser Ile
            20                  25                  30 caa aaa ggt ata                                                     108
Gln Lys Gly Ile
        35

<210> SEQ ID NO 114
<211> LENGTH: 36
<212> TYPE: PRT
<213> ORGANISM: Artificial sequence
<220> FEATURE:
<223> OTHER INFORMATION: Synthetic Construct: changes in various DT
      variants

<400> SEQUENCE: 114

Met Gly Ala Asp Asp Val Ser Glu Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile
        35

<210> SEQ ID NO 115
<211> LENGTH: 54
<212> TYPE: DNA
<213> ORGANISM: Artificial sequence
<220> FEATURE:
<223> OTHER INFORMATION: Synthetic Construct: changes in various DT
      variants
<220> FEATURE:
<221> NAME/KEY: CDS
<222> LOCATION: (1)..(54)

<400> SEQUENCE: 115 gca gta aac gtt gct cag gtt atc gat agc gaa act gct gat aac ctg     48
```

```
Ala Val Asn Val Ala Gln Val Ile Asp Ser Glu Thr Ala Asp Asn Leu
1               5                   10                  15 gaa aaa                                                                    54
Glu Lys <210> SEQ ID NO 116
<211> LENGTH: 18
<212> TYPE: PRT
<213> ORGANISM: Artificial sequence
<220> FEATURE:
<223> OTHER INFORMATION: Synthetic Construct: changes in various DT
      variants

<400> SEQUENCE: 116

Ala Val Asn Val Ala Gln Val Ile Asp Ser Glu Thr Ala Asp Asn Leu
1               5                   10                  15

Glu Lys

<210> SEQ ID NO 117
<211> LENGTH: 54
<212> TYPE: DNA
<213> ORGANISM: Artificial sequence
<220> FEATURE:
<223> OTHER INFORMATION: Synthetic Construct: changes in various DT
      variants
<220> FEATURE:
<221> NAME/KEY: CDS
<222> LOCATION: (1)..(54)

<400> SEQUENCE: 117 gca gta aac gtt gct cag gtt atc gaa agc gaa act gct gat aac ctg          48
Ala Val Asn Val Ala Gln Val Ile Glu Ser Glu Thr Ala Asp Asn Leu
1               5                   10                  15 gaa aaa                                                                    54
Glu Lys <210> SEQ ID NO 118
<211> LENGTH: 18
<212> TYPE: PRT
<213> ORGANISM: Artificial sequence
<220> FEATURE:
<223> OTHER INFORMATION: Synthetic Construct: changes in various DT
      variants

<400> SEQUENCE: 118

Ala Val Asn Val Ala Gln Val Ile Glu Ser Glu Thr Ala Asp Asn Leu
1               5                   10                  15

Glu Lys

<210> SEQ ID NO 119
<211> LENGTH: 54
<212> TYPE: DNA
<213> ORGANISM: Artificial sequence
<220> FEATURE:
<223> OTHER INFORMATION: Synthetic Construct: changes in various DT
      variants
<220> FEATURE:
<221> NAME/KEY: CDS
<222> LOCATION: (1)..(54)

<400> SEQUENCE: 119 gca gta aac gtt gct cag gtt atc tct agc gaa act gct gat aac ctg          48
Ala Val Asn Val Ala Gln Val Ile Ser Ser Glu Thr Ala Asp Asn Leu
1               5                   10                  15 gaa aaa                                                                    54
Glu Lys
```

```
<210> SEQ ID NO 120
<211> LENGTH: 18
<212> TYPE: PRT
<213> ORGANISM: Artificial sequence
<220> FEATURE:
<223> OTHER INFORMATION: Synthetic Construct: changes in various DT
      variants

<400> SEQUENCE: 120

Ala Val Asn Val Ala Gln Val Ile Ser Ser Glu Thr Ala Asp Asn Leu
1               5                   10                  15

Glu Lys
```

DIPHTHERIA TOXIN VARIANT

CROSS REFERENCE TO RELATED APPLICATIONS

This application is a continuation application of U.S. application Ser. No. 10/995,338 filed Nov. 24, 2004, now U.S. Pat. No. 7,585,942; which claims the benefit under 35 USC §119 (e) to U.S. Application Ser. No. 60/524,615 filed Nov. 25, 2003, now abandoned. The disclosure of each of the prior applications is considered part of and is incorporated by reference in the disclosure of this application.

BACKGROUND OF THE INVENTION

1. Field of the Invention

The present invention is directed to methods and compositions of modified variants of diphtheria toxin (hereinafter "DT") that reduce binding to vascular endothelium or vascular endothelial cells, therefore, reduce the incidence of Vascular Leak Syndrome (hereinafter "VLS").

2. Background Information

Vascular Leak Syndrome is primarily observed in patients receiving protein fusion toxin or recombinant cytokine therapy. VLS can manifest as hypoalbuminemia, weight gain, pulmonary edema and hypotension. In some patients receiving immunotoxins and fusion toxins, myalgia and rhabdomyolysis result from VLS as a function of fluid accumulation in the muscle tissue or the cerebral microvasculature [Smallshaw et al., *Nat. Biotechnol.* 21(4):387-91 (2003)]. VLS has occurred in patients treated with immunotoxins containing ricin A chain, saporin, pseudomonas exotoxin A and DT. All of the clinical testing on the utility of targeted toxins, immunotoxins and recombinant cytokines reported that VLS and VLS-like effects were observed in the treatment population. VLS occurred in approximately 30% of patients treated with $DAB_{389}IL-2$ [(Foss et al., *Clin Lymphoma* 1(4):298-302 (2001), Figgitt et al., *Am J Clin Dermatol*, 1(1):67-72 (2000)]. $DAB_{389}IL-2$, is interchangeable referred to in this application as DT387-IL2, is a protein fusion toxin comprised of the catalytic (C) and transmembrane (T) domains of DT (the DT toxophore), genetically fused to interleukin 2 (IL-2) as a targeting ligand. [Williams et al., *Protein Eng.*, 1:493-498 (1987); Williams et al., *J. Biol. Chem.*, 265:11885-11889 (1990); Williams et al., *J. Biol. Chem.*, 265 (33):20673-20677, Waters et al., *Ann. New York Acad. Sci.*, 30(636):403-405, (1991); Kiyokawa et al., *Protein Engineering*, 4(4):463-468 (1991); Murphy et al., *In Handbook of Experimental Pharmacology*, 145:91-104 (2000)]. VLS has also been observed following the administration of IL-2, growth factors, monoclonal antibodies and traditional chemotherapy. Severe VLS can cause fluid and protein extravasation, edema, decreased tissue perfusion, cessation of therapy and organ failure. [Vitetta et al., *Immunology Today*, 14:252-259 (1993); Siegall et al., *Proc. Natl. Acad. Sci.*, 91(20):9514-9518 (1994); Baluna et al., *Int. J. Immunopharmacology*, 18(6-7): 355-361 (1996); Baluna et al., *Immunopharmacology*, 37(2-3): 117-132 (1997); Bascon, *Immunopharmacology*, 39(3): 255 (1998)].

Reduction or elimination of VLS as a side effect would represent a significant advancement as it would improve the "risk benefit ratio" of protein therapeutics, and in particular, the immunotoxin and fusion toxin subclasses of protein therapeutics. (Baluna et al., *Int. J. Immunopharmacology*, 18(6-7): 355-361 (1996); Baluna et al., *Immunopharmacology*, 37(No. 2-3): 117-132 (1997); Bascon, *Immunopharmacology*, 39(3): 255 (1998). The ability to develop fusion proteins, single chain molecules comprised of a cytotoxin and unique targeting domain (scfv antibodies in the case of immunotoxins) could facilitate the development of the therapeutic agents for autoimmune diseases, such as rheumatoid arthritis and psoriasis transplant rejection and other non-malignant medical indications. (Chaudhary et al., *Proc. Natl. Acad. Sci. USA*, 87(23):9491-9494 (1990); Frankel et al., *In Clinical Applications of Immunotoxins Scientific Publishing Services*, Charleston S.C., (1997), Knechtle et al., *Transplantation*, 15(63):1-6 (1997); Knechtle et al., *Surgery*, 124(2): 438-446 (1998); LeMaistre, *Clin. Lymphoma*, 1:S37-40 (2000); Martin et al., *J. Am. Acad. Dermatol*, 45(6):871-881, 2001)). $DAB_{389}IL-2$ (ONTAK) is currently the only FDA approved protein fusion toxin and employs a DT toxophore and the cytokine interleukin 2 (IL-2) to target IL-2 receptor bearing cells and is approved for the treatment of cutaneous T-cell lymphoma (CTCL). (Figgitt et al., *Am. J. Clin. Dermatol*, 1(1):67-72 (2000); Foss, *Clin. Lymphoma*, 1(4):298-302 (2001); Murphy et al., *In Bacterial Toxins: Methods and Protocols*, Hoist O, ed, Humana Press, Totowa, N.J., pp. 89-100 (2000)). A number of other toxophores, most notably ricin toxin and pseudomonas exotoxin A, have been employed in developing both immuntoxins and fusion toxins; however, these molecules have not successfully completed clinical trials and all exhibit VLS as a pronounced side effect (Kreitman, *Adv. Pharmacol*, 28:193-219 (1994); Puri et al., *Cancer Research*, 61:5660-5662 (1996); Pastan, *Biochim Biophys Acta.*, 24:1333(2):C1-6 (1997); Frankel et al., *Supra* (1997); Kreitman et al., *Current Opin. Inves. Drugs*, 2(9): 1282-1293 (2001)).

VLS arises from protein-mediated damage to the vascular endothelium. In the case of recombinant proteins, immunotoxins and fusion toxins, the damage is initiated by the interaction between therapeutic proteins and vascular endothelial cells. Lindstrom et al. provided evidence that ricin toxin A had direct cytotoxic effects on human umbilical vein vascular epithelial cells but that these effects were not mediated by fibronectin (Lindstrom et al., *Blood*, 90(6):2323-34 (1997); Lindstrom et al., *Methods Mol. Biol*, 166:125-35 (2001)). Baluna et al. postulated that the interaction disrupts fibronectin mediated cell-to-cell interactions resulting in the breakdown of vascular integrity, and Baluna further suggested that in the toxin ricin, the interaction is mediated by a conserved three amino acid motif, (x)D(y), where x is L, I, G or V and y is V, L or S (Baluna et al., *Int. J. Immunopharmacology*, 18(6-7):355-361 (1996); Baluna et al., *Proc. Natl. Acad. Sci. USA*, 30:96(7):3957-3962, (1999); Baluna et al., *Exp Cell Res.*, 58(2):417-24 (2000)). It was reported that one of the VLS motifs found in ricin toxin, the 'LDV' motif, essentially mimics the activity of a subdomain of fibronectin which is required for binding to the integrin receptor. Integrins mediate cell-to-cell and cell-to-extracellular matrix interactions (ECM). Integrins function as receptors for a variety of cell surface and extracellular matrix proteins including fibronectin, laminin, vitronectin, collagen, osteospondin, thrombospondin and von Willebrand factor. Integrins play a significant role in the development and maintenance of vasculature and influence endothelial cell adhesiveness during angiogenesis. Further, it is reported that the ricin 'LDV' motif can be found in a rotavirus coat protein, and this motif is important for cell binding and entry by the virus. (Coulson, et al., *Proc. Natl. Acad. Sci. USA*, 94(10):5389-5494 (1997)). Thus, it appears to be a direct link between endothelial cell adhesion, vascular stability and the VLS motifs which mediate ricin binding to human vascular endothelial cells (HUVECs) and vascular leak.

Mutant dgRTAs were constructed in which this motif was removed by conservative amino acid substitution, and these mutants illustrated fewer VLS effects in a mouse model (Smallshaw et al. *Nat. Biotechnol.*, 21(4):387-91 (2003)). However, the majority of these constructs yielded dgRTA mutants that were not as cytotoxic as wild type ricin toxin, suggesting that significant and functionally critical structural changes in the ricin toxophore resulted from the mutations. It should also be noted that no evidence was provided to suggest that the motifs in dgRTA mediated HUVEC interactions and VLS in any other protein. Studies revealed that the majority of the mutant dgRTAs were much less effective toxophores and no evidence was provided to suggest that fusion toxins could be assembled using these variant toxophores.

DT is composed of three domains: the catalytic domain; transmembrane domain; and the receptor binding domain (Choe et al. *Nature*, 357:216-222 (1992)). Native DT is targeted to cells that express heparin binding epidermal growth factor-like receptors (Naglish et al., *Cell*, 69:1051-1061 (1992)). The first generation targeted toxins were initially developed by chemically cross-linking novel targeting ligands to toxins such as DT or mutants of DT deficient in cell binding (e.g. CRM45). (Cawley, *Cell* 22:563-570 (1980); Bacha et al., *Proc. Soc. Exp. Biol. Med.*, 181(1):131-138 (1986); Bacha et al., *Endocrinology*, 113(3):1072-1076 (1983); Bacha et al., *J. Biol. Chem.*, 258(3):1565-1570 (1983)). The native cell binding domain or a cross-linked ligand that directs the DT toxophore to receptors on a specific class of receptor-bearing cells must possess intact catalytic and translocation domains. (Cawley et al., *Cell*, 22:563-570 (1980); vanderSpek et al., *J. Biol. Chem.*, 5:268(16):12077-12082 (1993); vanderSpek et al., *J. Biol. Chem.*, 7(8):985-989 (1994); vanderSpek et al., *J. Biol. Chem.*, 7(8)985-989 (1994); Rosconi, *J. Biol. Chem.*, 10; 277(19):16517-161278 (2002)). These domains are critical for delivery and intoxification of the targeted cell following receptor internalization (Greenfield et al, *Science*, 238(4826)536-539 (1987)). Once the toxin, toxin conjugate or fusion toxin has bound to the cell surface receptor the cell internalizes the toxin bound receptor via endocytic vesicles. As the vesicles are processed they become acidified and the translocation domain of the DT toxophore undergoes a structural reorganization which inserts the 9 transmembrane segments of the toxin into the membrane of the endocytic vesicle. This event triggers the formation of a productive pore through which the catalytic domain of the toxin is threaded. Once translocated the catalytic domain which possess the ADP-ribosyltransferase activity is released into the cytosol of the targeted cell where it is free to poison translation thus effecting the death of the cell (reviewed in vanderSpek et al., *Methods in Molecular Biology*, Bacterial Toxins: methods and Protocols, 145:89-99, Humana press, Totowa, N.J., (2000)).

Chemical cross-linking or conjugation results in a variety of molecular species representing the reaction products, and typically only a small fraction of these products are catalytically and biologically active. In order to be biologically active, the reaction products must be conjugated in manner that does not interfere with the innate structure and activity of the catalytic and translocation domains in the toxophore. Resolution of the active or highly active species from the inactive species is not always feasible as the reaction products often possess similar biophysical characteristics, including for example size, charge density and relative hydrophobicity. It is noteworthy that isolation of large amounts of pure clinical grade active product from chemically crosslinked toxins is not typically economically feasible for the production of pharmaceutical grade product for clinical trials and subsequent introduction to clinical marketplace. To circumvent this issue, a genetic DT-based protein fusion toxin in which the native DT receptor-binding domain was genetically replaced with melanocyte-stimulating hormone as a surrogate receptor-targeting domain was created (Murphy et al, *PNAS*, 83:8258-8262 (1986)). This approach was used with human IL-2 as a surrogate targeting ligand to create $DAB_{486}IL-2$ that was specifically cytotoxic only to those cells that expressed the high-affinity form of the IL-2 receptor (Williams et al., *Protein Eng.*, 1:493-498 (1987)). Subsequent studies of $DAB_{486}IL-2$ indicated that truncation of 97 amino acids from the DT portion of the molecule resulted in a more stable, more cytotoxic version of the DL-2 receptor targeted toxin, $DAB_{389}IL-2$ (Williams et al., *J. Biol. Chem.*, 265:11885-889 (1990)). The original constructs (the 486 forms) still possessed a portion of the native DT cell binding domain. The $DAB_{389}$ amino acid residue version contains the C and T domains of DT with the DT portion of the fusion protein ending in a random coil between the T domain and the relative receptor binding domain. A number of other targeting ligands have since been genetically fused to this DT toxophore, $DAB_{389}$. (vanderSpek et al., *Methods in Molecular Biology, Bacterial Toxins:Methods and Protocols.*, 145:89-99, Humana Press, Totowa, N.J. (2000)). Similar approaches have now been employed with other bacterial proteins and genetic fusion toxins are often easier to produce and purify.

SUMMARY OF THE INVENTION

The present invention provides compositions of modified variants of DT that reduce binding to vascular endothelium or vascular endothelial cells, and therefore, reduce the incidence of Vascular Leak Syndrome.

One aspect of the present invention relates to a composition comprising a polypeptide toxophore from a DT, said polypeptide toxophore comprising amino acid residues 7-9, 29-31 and 290-292 of SEQ ID NO:4, wherein at least one amino acid in said amino acid residues 7-9, 29-31 or 290-292 of SEQ ID NO:4 has been substituted or deleted.

Another aspect of the present invention relates to a fusion protein comprising a modified DT mutant or fragment and a non-DT fragment.

Another aspect of the present invention relates to the use of a modified DT or a fusion protein carrying such modified DT for the treatment of diseases, such as cancer.

Yet another aspect of the present invention relates to a method of making a modified DT fragment having a reduced binding activity to human vascular endothelial cells (HUVEC) and having a reduced induction of Vascular Leak Syndrome (VLS).

BRIEF DESCRIPTION OF THE DRAWINGS

FIG. 1 is a schematic diagram of DT387. The positions of the (x)D(y) motifs of the toxophore which are implicated in VLS are indicated by triangles and listed below in the table of proposed DT387 and corresponding $DAB_{389}IL2$ (hereinafter "DT387IL2") mutants. The flexible linker sterically enhances disulfide bond formation between the C-terminal cysteine residue and a Sulfo-LC SPDP modified targeting ligand.

FIG. 3 shows the nucleic acid and amino acid sequence changes in various DT variants.

DETAILED DESCRIPTION OF THE INVENTION

Figure 2:
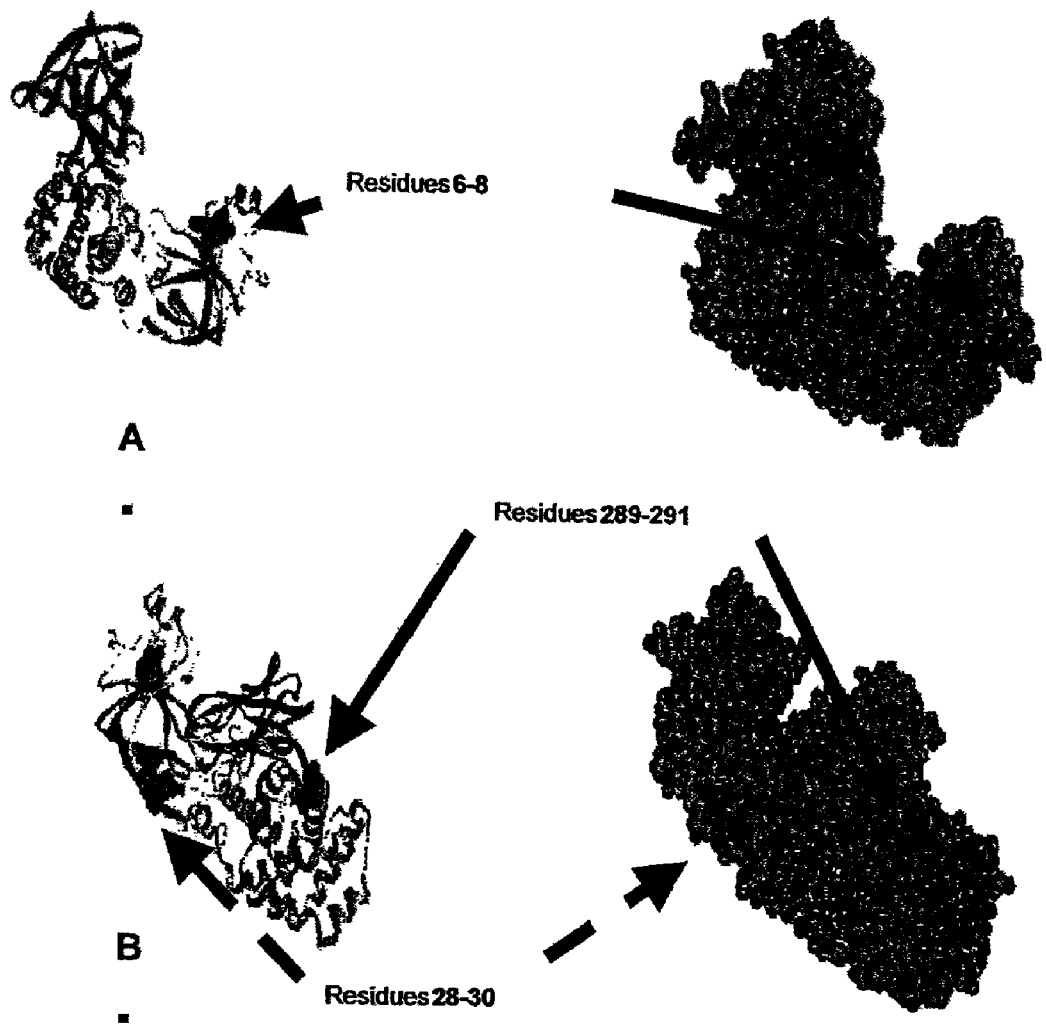
FIG. 2 is a ribbon diagram and space filling model of native DT showing the presence of (x)D(y) motifs implicated in VLS.

The primary objective of the present invention is to provide compositions comprising modified variants of DT that reduce binding to vascular endothelium or vascular endothelial cells, and therefore, reduce the incidence of Vascular Leak Syndrome (hereinafter "VLS"). The second objective of the present invention is to provide methods of making such modified variants of DT that reduce binding to vascular endothelium or vascular endothelial cells. The third objective of the present invention is to provide methods of treating various diseases, such as cancer, by using modified variants of DT or by using a fusion protein comprising modified variants of DT and non-DT protein.

One aspect of the present invention relates to genetically modified molecules of diphtheria toxin (DT) having reduced binding to human vascular endothelial cells (HUVECs). These modified DT molecules are hereinafter referred to as "DT variants." The invention specifically relates to DT variants having one or more conservative changes within the (x)D(y) motifs of the DT molecule, i.e., at residues 6-8 (VDS), residues 28-30 (VDS), and residues 289-291 (IDS) of the native DT sequence (SEQ ID NO:1), or at residues 7-9 (VDS), residues 29-31 (VDS), and residues 290-292 (IDS) of the SEQ ID NO:4. Since the (x)D(y) motifs are referred to as "VLS motifs," the DT variants with modified (x)D(y) motif are sometimes referred to as "VLS-modified DT molecules."

Conservative changes are defined as those amino acid substitutions which permit the alteration of the native sequence within these regions but do not impair the cytotoxicity of the toxophore. These conservative changes would not include those that regenerate the VDS/IDS sequences responsible for mediating the interaction with endothelial cells. Such non-native recombinant sequences therefore comprise a novel series of mutants that maintain the native function of the unique domains of diphtheria toxin while significantly decreasing their ability to interact with vascular endothelial cells.

In one embodiment, the DT variants of the present invention contain at least one conservative change within one of the (x)D(y) motifs of the DT molecule, i.e., within residues 6-8 (VDS), residues 28-30 (VDS), and residues 289-291 (IDS) of SEQ ID NO: 1 to eliminate motifs that are associated with VLS and thereby reduce the clinical adverse effects commonly associated with this syndrome. The DT variants of the present invention, however, are as effective and efficient as DT387 in their ability to facilitate the delivery of its catalytic domain to the cytosol of targeted eukaryotic cells when incorporated into protein fusion toxins. DT387 (SEQ ID NO:4) is a truncated DT protein comprising amino acid residues 1-386 (SEQ ID NO:2) of the native DT protein including the catalytic domain and the translocation domain.

In another embodiment, in addition to the modification in the (x)D(y) motifs, the DT variants may further comprise a deletion or substitution of 1 to 30 amino acids of SEQ ID NO:4, preferably 1 to 10 amino acids, most preferably 1-3 amino acids.

To produce DT variants with a modified (x)D(y) sequence, one could delete or substitute another amino acid for the aspartic acid (D), or insert one or more amino acids at or adjacent to its position. Any amino acid that may replace the (D) residue in the sequence as a consequence of a deletion or mutation event must retain the ability to effectively deliver the catalytic domain of DT to a targeted cell within the context of a fusion protein, and not reconstitute an intact VLS motif.

Alternatively the (x) residue could be deleted, substituted, or moved by the insertion of one or more amino acids, to remove the (x)D(y) sequence. Any amino acid that may replace the (x) residue in the sequence as a consequence of the deletion or mutation event should preferably not be leucine (L), isoleucine (I), glycine (G) or valine (V). The (y) residue could be deleted, substituted, or moved by the insertion of one or more amino acids, to remove the (x)D(y) sequence. Any amino acid that may replace the (y) residue in the sequence as a consequence of the deletion or mutation event should preferably not be valine (V), leucine (L) or serine (S).

In a preferred embodiment, the DT variants of the present invention contain at least one of the mutations selected from the group of V7A, V7S, D8S, D8E, V29A, I290A, D291S, and D291E. It should be noted that the first amino acid residue of mature processed native DT protein corresponds to the second amino acid residue of the DT variants (recombinant expression requires insertion of met residue). Accordingly, residues 6-8 (VDS), 28-30 (VDS) and 289-291 (IDS) of the native DT correspond to residues 7-9, 29-31, and 290-292 of the DT variants.

In another preferred embodiment, the DT variants of the present invention contain a double mutation selected from the group of V7AV29A, V7SV29A, D8SV29A, D8SD291S, D8EV29A, and V29AD291E.

In another preferred embodiment, the DT variants of the present invention contain a triple mutation selected from the group of V7AV29AD291E and V7AV29AI290A.

In yet another preferred embodiment, the DT variants comprise an amino acid sequence recited in one of SEQ ID NOs: 28-38. It is conceivable that other residues that are positioned in the physical region, three-dimensional space, or vicinity of the HUVEC binding site and/or the (x)D(y) motif may be mutated or altered to abrogate, reduce, or eliminate VLS. The amino acids targeted for mutation in the flanking regions include amino acids on or near the surface of a native DT protein. The alteration may remove or substitute a charged residue in the region of a (x)D(y) motif, which may negate or reverse the charge in a particular area on the surface of the protein. The alteration may also change size and/or hydrophilic nature of an amino acid in the physical region, space or vicinity of the (x)D(y) sequence or active site of a protein.

In certain aspects, mutagenesis of nucleic acids encoding peptides, polypeptides or proteins may be used to produce the desired mutations in the (x)D(y) and flanking sequences of the DT variants. Mutagenesis may be conducted by any means disclosed herein or known to one of ordinary skill in the art.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation [(Cunningham et al., *Science,* 2:244 (4908): 1081-5 (1989)].

As specific amino acids may be targeted, site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the mutation site being traversed. Typically, a primer of about 17 to 25 nucleotides in length is preferred, with about 5 to 10 residues on both sides of the junction of the sequence being altered.

In general, the technique of site-specific mutagenesis is well known in the art. Briefly, a bacteriophage vector that will produce a single stranded template for oligonucleotide directed PCR mutagenesis is employed. These phage vectors, typically M13, are commercially available and their use is generally well known to those skilled in the art Similarly, double stranded plasmids are also routinely employed in site directed mutagenesis, which eliminates the step of transferring the gene of interest from a phage to a plasmid. Synthetic oligonucleotide primers bearing the desired mutated sequence are used to direct the in vitro synthesis of modified (desired mutant) DNA from this template and the heteroduplex DNA used to transform competent *E. Coli* for the growth selection and identification of desired clones. Alternatively, a pair of primers may be annealed to two separate strands of a double stranded vector to simultaneously synthesize both corresponding complementary strands with the desired mutation(s) in a PCR reaction.

In one embodiment, the Quick Change site-directed mutagenesis method using plasmid DNA templates as described by Sugimoto et al. is employed (Sugimoto et al, *Annal Biochem.,* 179(2):309-311 (1989)). PCR amplification of the plasmid template containing the insert target gene of insert is achieved using two synthetic oligonucleotide primers containing the desired mutation. The oligonucleotide primers, each complementary to opposite strands of the vector, are extended during temperature cycling by mutagenesis-grade Pfu Turbo DNA polymerase. On incorporation of the oligonucleotide primers, a mutated plasmid containing staggered nicks is generated. Amplified un-methylated products are treated with Dpn I to digest methylated parental DNA template and select for the newly synthesized DNA containing mutations. Since DNA isolated from most *E. Coli* strains is dam methylated, it is susceptible to Dpn I digestion, which is specific for methylated and hemimethylated DNA. The reaction products are transformed into high efficiency strains of *E. coli* to obtain plasmids containing the desired mutants.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants. These basic techniques, the protocols for sequence determination, protein expression and analysis are incorporated by reference to citations in this specification and are generally accessible to those reasonably skilled in the art within *Current Protocols in Molecular Biology* (Fred M. Ausubel, Roger Brent, Robert E. Kingston, David D. Moore, J. G. Seidman, John A. Smith, Kevin Struhl, Editors John Wiley and Sons Publishers (1989)).

The present invention also provides DT fusion proteins. A DT fusion protein contains a DT-related polypeptide (e.g., a DT variant of the present invention) and a non-DT polypeptide fused in-frame to each other. The DT-related polypeptide corresponds to all or a portion of DT variant having reduced binding to human vascular endothelial cells. In one embodiment, a DT fusion protein comprises at least one portion of a DT variant sequence recited in one of SEQ ID NOs: 11-27.

Preferably, a DT-fusion protein of the present invention is produced by standard recombinant DNA techniques. For example, DNA fragments coding for the different polypeptide sequences are ligated together in-frame in accordance with conventional techniques, for example, by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence.

A peptide linker sequence may be employed to separate the DT-related polypeptide from non-DT polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the DT-related polypeptide and non-DT polypeptide; and (3) the lack of hydrophobic or charged residues that might react with the polypeptide functional epitopes. Preferred peptide linker sequences contain gly, asn and ser residues. Other near neutral amino acids, such as thr and ala, may also be used in the linker sequence. Amino acid sequences which may be usefully employed as linkers include those disclosed in Maratea et al., *Gene*, 40:39-46, 1985; Murphy et al., *Proc. Natl. Acad. Sci. USA*, 83:8258-8262, 1986; U.S. Pat. No. 4,935,233 and U.S. Pat. No. 4,751,180. The linker sequence may generally be from 1 to about 50 amino acids in length. Linker sequences are not required when the DT-related polypeptide and non-DT polypeptide have non-essential N-terminal amino acid regions that can be used to separate the functional domains and prevent steric interference. For example, DT389/DT387-linker has a sequence of SEQ ID NO:5, DT380-linker has sequence of SEQ ID NO:6. The non-DT polypeptides can be any polypeptide.

In one embodiment, the non-DT polypeptide is a cell-specific binding ligand. The specific-binding ligands used in the invention can contain an entire ligand, or a portion of a ligand which includes the entire binding domain of the ligand, or an effective portion of the binding domain. It is most desirable to include all or most of the binding domain of the ligand molecule.

Specific-binding ligands include but not limited to: polypeptide hormones, chimeric toxins, e.g., those made using the binding domain of α-MSH, can selectively bind to melanocytes, allowing the construction of improved DT-MSH chimeric toxins useful in the treatment of melanoma. (Murphy, J. R., Bishai, W., Miyanohara, A., Boyd, J., Nagle, S., *Proc. Natl. Acad. Sci. U.S.A.,* 83(21):8258-8262 (1986)). Other specific-binding ligands which can be used include insulin, somatostatin, interleukins I and HI, and granulocyte colony stimulating factor. Other useful polypeptide ligands having cell-specific binding domains are follicle stimulating hormone (specific for ovarian cells), luteinizing hormone (specific for ovarian cells), thyroid stimulating hormone (specific for thyroid cells), vasopressin (specific for uterine cells, as well as bladder and intestinal cells), prolactin (specific for breast cells), and growth hormone (specific for certain bone cells). Specific-binding ligands which can be used include cytokines. Examples of cytokines include, but are not limited to, IL-1, IL-2, IL-3, IL-4, EL-5, IL-6, IL-7, IL-8, IL-9, IL-10, IL-11, IL-12, IL-13, IL-14, IL-15, P-interferon, α-interferon (INF α), INFγ, angiostatin, thrombospondin, endostatin, METH-1, METH-2, GM-CSF, G-CSF, M-CSF, tumor necrosis factor (TNF), SVEGF, TGFβ, Flt3 and B-cell growth factor. IL-2 is of particular importance because of its role in allergic reactions and autoimmune diseases such as systemic lupus erythmatosis (SLE), involving activated T cells. DT fusion protein made using B-cell growth factor can be used as immunosuppressant reagents which kill proliferating B-cells, which bear B-cell growth factor receptors, and which are involved in hypersensitivity reactions and organ rejection. Other preferred cytokines include Substance P (Benoliel et al., *Pain,* 79(2-3):243-53 (1999)), VEGF (Hotz et al., *J Gastrointest Surg.,* 6(2):159-66 (2002)), IL3 (Jo et al., *Protein Exp Purif.* 33(1):123-33 (2004)) and GMCSF (Frankel et al., *Clin Cancer Res,* 8(5):1004-13 (2002)). VLS modified DT fusion toxins using these ligands are useful in treating cancers or other diseases of the cell type to which there is specific binding.

For a number of cell-specific ligands, the region within each such ligand in which the binding domain is located is now known. Furthermore, recent advances in solid phase polypeptide synthesis enable those skilled in this technology to determine the binding domain of practically any such ligand, by synthesizing various fragments of the ligand and testing them for the ability to bind to the class of cells to be labeled. Thus, the chimeric genetic fusion toxins of the invention need not include an entire ligand, but rather may include only a fragment of a ligand which exhibits the desired cell-binding capacity. Likewise, analogs of the ligand or its cell-binding region having minor sequence variations may be synthesized, tested for their ability to bind to cells, and incorporated into the hybrid molecules of the invention. Other potential ligands include antibodies (generally monoclonal) or antigen-binding, single-chain analogs of monoclonal antibodies, where the antigen is a receptor or other moiety expressed on the surface of the target cell membrane. The antibodies most useful are those against tumors; such antibodies are already well-known targeting agents used in conjunction with covalently bound cytotoxins. In the present invention, the anti-tumor antibodies (preferably not the whole antibody, but just the Fab portion) are those which recognize a surface determinant on the tumor cells and are internalized in those cells via receptor-mediated endocytosis; antibodies which are capped and shed will not be as effective.

Another aspect of the present invention pertains to vectors containing a polynucleotide encoding a DT variant or a DT fusion protein. One type of vector is a "plasmid," which includes a circular double-stranded DNA loop into which additional DNA segments can be ligated. In the present specification, "plasmid" and "vector" can be used interchangeably as the plasmid is the most commonly used form of vector. However, the invention is intended to include such other forms of vectors, such as expression vectors, and gene delivery vectors.

The expression vectors of the invention comprise a polynucleotide encoding DT variant or a DT fusion protein in a form suitable for expression of the polynucleotide in a host cell. The expression vectors generally have one or more regulatory sequences, selected on the basis of the host cells to be used for expression, which is operatively linked to the polynucleotide sequence to be expressed. It will be appreciated by those skilled in the art that the design of the expression vector can depend on such factors as the choice of the host cell to be transformed, the level of expression of protein desired, and the like. The expression vectors of the invention can be introduced into host cells to produce proteins or peptides, including fusion proteins or peptides, encoded by polynucleotides as described herein (e.g., a DT variant or a DT fusion protein, and the like).

The expression vectors of the present invention can be designed for expression of a DT variant or a DT fusion protein in prokaryotic or eukaryotic cells. It should be noted that the presence of a single DT molecule inside an eukaryotic cell would kill the cell. Specifically, the toxin binds to EF-tu which is required for translation and ribosylation. Accordingly, DT can only be expressed in cells with modified EF-tu that is no longer recognized by DT. (see, e.g., Liu et al., *Protein Expr Purif.,* 30:262-274 (2003); Phan et al., *J. Biol. Chem.,* 268(12):8665-8 (1993); Chen et al., *Mol. Cell Biol,* 5(12):3357-60 (1985); Kohne et al., Somat *Cell Mol Genet.,* 11 (5):421-31 (1985); Moehring et al., *Mol. Cell Biol.,* 4(4):642-50 (1984)). In addition, a DT variant or a DT fusion protein can be expressed in bacterial cells such as *E. coli* [Bishai et al., *J Bacteriol* 169(11):5140-51 (1987)]. Consideration must be given to the expression and activity of the types and levels of host protease expression, and this is dependent upon the cleavage site present in the engineered DT toxophore. The innate expression host protease expression profile could negatively impact the yields of DT fusion toxin produced [Bishai et al., *Supra* (1987)]. To the degree that this requisite cleavage site can be altered to modulate the cell selectivity of resultant fusion proteins, it is envisioned that such cleavage site mutants could be in VLS-modified toxophores (Gordon et al., *Infect Immun*, 63(1):82-7 (1995); Gordon et al., *Infect Immun*, 62(2):333-40 (1994); Vallera et al., *J Natl. Cancer Inst.*, 94:597-606 (2002); Abi-Habib et al., *Blood.*, 104(7):2143-8 (2004)]. Alternatively, the expression vector can be transcribed and translated in vitro.

The present invention further provides gene delivery vehicles for the delivery of polynucleotides to cells, tissue, or a mammal for expression. For example, a polynucleotide sequence of the present invention can be administered either locally or systemically in a gene delivery vehicle. These constructs can utilize viral or non-viral vector approaches in in vivo or ex vivo modality. Expression of such coding sequences can be induced using endogenous mammalian or heterologous promoters. Expression of the coding sequence in vivo can be either constitutive or regulated. The invention includes gene delivery vehicles capable of expressing the contemplated polynucleotides including viral vectors. For example, Qiao et al., developed a system employing PG13 packaging cells produce recombinant retroviruses carrying a DT fragment which kills cancer cell and provides a method for using DT as component a suicide vector. Qiao et al., *J. Virol.* 76(14):7343-8 (2002).

Expressed DT-mutants and DT-fusion proteins can be tested for their functional activity. Methods for testing DT activity are well-known in the art. For example, the VLS effect of DT-mutants and DT-fusion proteins can be tested in HUVECs as described in Example 2. The ribosyltransferase activity of DT variants or DT-fusion proteins can be tested by the ribosyltransferase assay described in Example 3. The cytotoxicity of DT variants or DT-fusion proteins can be tested as described in Examples 4-5.

DT-mutants and DT-fusion proteins having reduced binding to HUVECs while maintaining the cytotoxicity can be used for the treatment of various cancers, including, but not limited to breast cancer, colon-rectal cancer, lung cancer, prostate cancer, skin cancer, osteocarcinoma, or liver cancer and others.

In an exemplary embodiment, the VLS modified DT fusion toxins of the invention are administered to a mammal, e.g., a human, suffering from a medical disorder, e.g., cancer, or non-malignant conditions characterized by the presence of a class of unwanted cells to which a targeting ligand can selectively bind.

The pharmaceutical composition can be administered orally or by intravenously. For example, intravenous now possible by cannula or direct injection or via ultrasound guided fine needle. Mishra (Mishra et al., *Expert Opin. Biol*, 3(7):1173-1180 (2003)) provides for intratumoral injection.

The term "therapeutically effective amount" as used herein, is that amount achieves at least partially a desired therapeutic or prophylactic effect in an organ or tissue. The amount of a modified DT necessary to bring about prevention and/or therapeutic treatment of the disease is not fixed per se. The amount of VLS modified DT fusion toxin administered will vary with the type of disease, extensiveness of the disease, and size of species of the mammal suffering from the disease. Generally, amounts will be in the range of those used for other cytotoxic agents used in the treatment of cancer, although in certain instances lower amounts will be needed because of the specificity and increased toxicity of the VLS-modified DT fusion toxins. In certain circumstances and as can be achieved by currently available techniques for example (cannulae or convection enhanced delivery, selective release) attempts to deliver enhanced locally elevated fusion toxin amounts to specific sites may also be desired. (Laske et al., *J Neurosurg.*, 87:586-5941(997); Laske et al., *Nature Medicine*, 3:1362-1368 (1997), Rand et al., *Clin. Cancer Res.*, 6:2157-2165 (2000); Engebraaten et al., *J. Cancer,* 97:846-852 (2002), Prados et al, *Proc. ASCO*, 21:69b (2002), Pickering et al., *J Clin Invest,* 91(2):724-9 (1993)).

The invention is further directed to pharmaceutical compositions comprising a DT variant or DT-fusion protein described hereinabove and a pharmaceutically acceptable carrier.

As used herein the language "pharmaceutically acceptable carrier" is intended to include any and all solvents, solubilizers, stabilizers, absorbents, bases, buffering agents, lubricants, controlled release vehicles, diluents, emulsifying agents, humectants, lubricants, dispersion media, coatings, antibacterial or antifungal agents, isotonic and absorption delaying agents, compatible with pharmaceutical administration. The use of such media and agents for pharmaceutically active substances is well-known in the art. See e.g., A.H. Kibbe Handbook of Pharmaceutical Excipients, 3rd ed. Pharmaceutical Press London, UK (2000). Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, or glycerine; propylene glycol or other synthetic solvents; antibacterial agents such as benzyl alcohol or methyl parabens; antioxidants such as ascorbic acid or sodium bisulfate; chelating agents such as emylene-diarninetetracetic acid; buffers such as acetates, citrates or phosphates and agents for the adjustment of tonicity such as sodium chloride or dextrose pH which can be adjusted with acids or bases, such as hydrochloric acid or sodium hydroxide. The parenteral preparation can be enclosed in ampoules, disposable syringes or multiple dose vials made of glass or plastic.

Mainly if not exclusively this pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. Prolonged absorption of the injectable compositions can be brought about by including in the composition an agent which delays absorption (e.g. aluminum monostearate or gelatin), however, any stabilizer or additive posited by this disclosure envisioned for use in protein fusion toxin delivery will be compatible with protein based therapeutics.

Sterile injectable solutions can be prepared by incorporating the active ingredient (e.g., a viral or non viral vector) in the required amount in an appropriate solvent with one or a combination of ingredients enumerated above, as required, followed by filtered sterilization. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation are vacuum drying and freeze drying which yields a powder of the active ingredient plus any additional desired ingredient from a previously sterile-filtered solution thereof.

Toxicity and therapeutic efficacy of such ingredient can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to noncancerous and otherwise healthy cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration arrange that includes the IC50 (i.e., the concentration of the test compound which achieves a half-maximal inhibition of symptoms) as determined in cell culture and as presented below examples 4-5. Such information can be used to more accurately determine useful doses in humans. Levels in plasma may be measured, for example, by high performance liquid chromatography. The pharmaceutical compositions can be included in a container, pack, or dispenser together with instructions for administration.

The present invention is further illustrated by the following examples which should not be construed as limiting. The contents of all references, patents and published patent applications cited throughout this application, as well as the Figures and Tables, are incorporated herein by reference.

EXAMPLE 1

Construction, Expression and Purification of DT Variant and DT-Fusion Proteins

1(a) Construction of DT Variant and DT-Fusion Proteins

A truncated DT-based toxophore comprising a methionine residue at the N-terminus, amino acid residues 1 through 386 (SEQ ID NO:2) of the native DT (now residues 2-387 in the truncated toxophore), and two additional amino acids residues His and Ala at the C-terminal was constructed. The inclusion of the His and Ala residues was resulted from additional nucleotide sequences introduced during the cloning process. This construct is designated as DT387 (SEQ ID NO:4). A schematic diagram of DT387 is shown in FIG. 1 which is equivalent to the DAB389 construct described by Williams et al. with the exception that codon was altered and optimized for E. Coli rather than C. diphtheria. A similar construct containing amino acid residues 1 through 379 of the native DT, with a methionine residue at the N-terminal, was also constructed, which was designated was DT380 (SEQ ID NO:3). A DT380 variant with a linker and caboxy terminal cysteine was used to determine the effects of VLS mutations on ribosyltransferase activities and to determine propensity to induce VLS as a function of HUVEC binding.

As shown in FIG. 2, native DT contains three (x)D(y) motifs at residues 6-8 (VDS), residues 28-30 (VDS), and residues 289-291 (IDS). (The number of the residues in the genetic constructs is +1 with respect to native DT). Briefly, site directed mutagenesis was employed to alter the (x)D(y) motif in DT387. A Stratagene Quickchange mutagenesis kit was used to construct the mutations. Oligonucleotide primers were designed to alter encoding residues within the (x)D(y) motif implicated in VLS.

Table 1 provides a list of all the DT mutants that were created, expressed in E. coli, partially purified (not to absolute homogeneity) and tested for cytotoxicity. The corresponding nucleic acid and amino acid sequence changes are shown in FIG. 3. The mutants were tested in the context of protein fusion toxin genetically fused to sequences encoding either human interleukin 2 or human epidermal growth factor.

TABLE 1

Mutant DT Toxophores

| SINGLE MUTANT | SEQ ID NOs |
| --- | --- |
| DT387(V7A) | 28 |
| DT387 (D8S) | 29 |
| DT387 (AD8) | 44 |
| DT387 (V7S) | 30 |
| DT387 (D8E) | 31 |
| DT387 (V29A) | 32 |
| DT387 (V290A) | 33 |
| DT387 (D291E) | 34 |

| DOUBLE MUTANT | SEQ ID NO |
| --- | --- |
| DT387(V7A, V29A) | 35 |
| DT387(V7S, V29A) | 36 |
| DT387(D8E, V29A) | 37 |
| DT387(D8S, V29A) | 38 |
| DT387(V29A, D291E) | 39 |

| TRIPLE MUTANT | SEQ ID NO |
| --- | --- |
| DT387(V7A, V29A, I290A) | 40 |
| DT387(V7A, V29A, D291E) | 41 |

A number of DT-fusion proteins were also expressed and purified. These proteins and their corresponding DT counterparts are listed in Table 2.

TABLE 2

DT-fusion proteins and control proteins.

| Fusion proteins | SEQ ID NO |
| --- | --- |
| DT387EGF/DAB389 EGF | 7 |
| DT387 linker EGF/DAB389 linker EGF | 8 |
| DT387IL2/DAB389IL-2 | 9 |
| DT387 linker IL2/DAB389 linker IL2 | 10 |
| DT387(V7A) linkerIL2 | 11 |
| DT387(D8S) linker IL2 | 12 |
| DT387(D8E) linker IL2 | 13 |

TABLE 2-continued

DT-fusion proteins and control proteins.

| | SEQ ID NO |
|---|---|
| DT387(V29A) linker IL2 | 14 |
| DT387(I290A) linker IL2 | 15 |
| DT387(D291E) linker IL2 | 16 |
| DT387(V7AV29A) linker IL2 | 17 |
| DT387(V7AV29AD291E) linker IL2 | 18 |
| DT387(D8SV29A) linker IL2 | 19 |
| DT387(V7SV29A) linker IL2 | 42 |
| DT387(D8EV29A) linker IL2 | 43 |
| DAB389(V7AV29AI290A) linker IL2 | 20 |
| DT387(V29A) linker EGF | 21 |
| DT387(D291E) linker EGF | 22 |
| DT387(D8EV29A) linker EGF | 23 |
| DT387(V7SV29A) linker EGF | 24 |
| DT387(V7AV29A) linker EGF | 25 |
| DT387(D8EV29AD291E) linker EGF | 26 |
| DT387(D8SV29A) linker EGF | 27 |
| DT387(V7A)IL2 | 46 |
| DT387(D8S)IL2 | 47 |
| DT387(D8E)IL2 | 48 |
| DT387(V29A)IL2 | 49 |
| DT387(I290A)IL2 | 50 |
| DT387(D291E)IL2 | 51 |
| DT387(V7AV29A)IL2 | 52 |
| DT387(V7AV29AD291E)IL2 | 53 |
| DT387(D8SV29A) IL2 | 54 |
| DT387(V7SV29A) IL2 | 55 |
| DT387(D8EV29A) IL2 | 56 |
| DAB389(V7AV29AI290A) IL2 | 57 |
| DT387(V29A) EGF | 58 |
| DT387(D291E) EGF | 59 |
| DT387(D8EV29A) EGF | 60 |
| DT387(V7SV29A) EGF | 61 |
| DT387(V7AV29A) EGF | 62 |
| DT387(D8EV29AD291E) EGF | 63 |
| DT387(D8SV29A) EGF | 64 |
| Corresponding DT counterparts | |
| DT387/DAB389 | 4 |

1(b) Expression and Purification of DT Variants and DT-Fusion Proteins

Figure 4A:
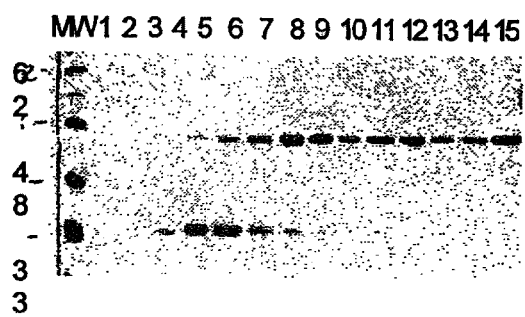
FIG. 4A shows analysis of DT387 toxophore yield by Coomassie.
Figure 4B:
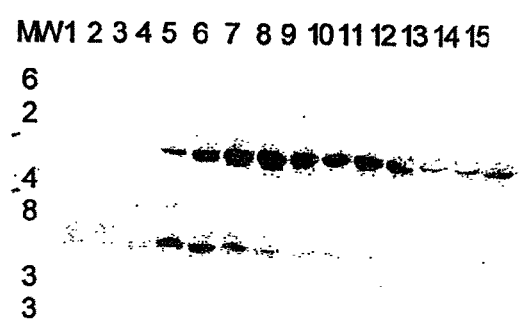
FIG. 4B shows analysis of DT387 toxophore yield by Western Blot.

Plasmid constructs encoding truncated DT protein, DT mutants, and DT-fusion protein were transformed into *E. coli* HMS174 (DE3) cells. *E. coli* HMS174 is a protease-deficient strain in which over-expression of recombinant proteins can be achieved. Induction of the recombinant protein expression was obtained by addition of isopropylthiogalactosidase (ITPG) to *E. coli* HMS174. Following incubation, the bacterial cells were harvested by centrifugation and lysed, and the recombinant protein was further purified from inclusion body preparations as described by Murphs and vanderSpek, *Methods in Molecular Biology, Bacterial Toxins methods and protocols*, 145:89-99 Humana press, Totowa, N.J. (2000). The crude protein preparations were contaminated with endotoxin levels of between $2.5 \times 10^4$ and $2.5 \times 10^5$ EU/ml. It was necessary to remove endotoxins from the protein preparations to assure that effects on HUVECs are from VLS and not due to the presence of the endotoxins. Endotoxin was removed to <250 EU/ml by passage over an ion-exchange resin. As shown in FIG. 4, separation of breakdown products from full-length material also occurred during the ion-exchange chromatography. After another final purification over ion exchange resin endotoxin was reduced to <25 EU/ml and the toxophore was tested for VLS as a function of HUVEC cell binding in vitro. FIG. 4 is the analysis of DT387 toxophore yield by Coomassie and Western Blot. Samples from pilot production process described above resolved by SDS Polyacrylamide Gel Electrophoresis (PAGE). Samples 7 through 13 elute from column with less than 250 EU/ml [initial levels >25,000 EU/ml] and as essentially pure DT toxophore. Molecular weight standards are indicated (kDa). An anti-DT antibody was used for the Western blot.

Some of the constructs are more difficult to express and purify. Mutations that result in stable constructs with adequate expression that do not affect ribosyltransferase activity of the DT387 toxophore were subsequently tested for targeted cytotoxicity in the corresponding VLS modified DT-EGF and VLS modified DT-IL-2 protein fusion toxins (Examples 4 and 5 respectively).

As described in more detail in Examples 2-4, DT387, VLS modified DT387EGF and DT387EL-2 have been used to distinguish between effects of the VLS mutations on catalytic activity, VLS activity and effective delivery of the targeted protein fusion toxins to the cytosol of target cells.

EXAMPLE 2

Binding of DT Toxophores to HUVEC In Vitro

Human vascular endothelial cells were maintained in EGM media (obtained from Cambrex, Walkersville, Md.). Subconfluent early passage cells were seeded at equivalent cell counts onto plastic cover slips. Purified, endotoxin free wild type DT toxophore and mutants DT38(V7AV29A)gscys and DT380(D8SD291 S)gscys were labeled with the fluorescent tag F-150 (Molecular Probes, Eugene, Oreg.) through chemical conjugation. HUVECs were incubated with equivalent amounts of the labeled toxophores. The media was then aspirated, the cells washed and then, fixed and prepared for analysis. Examination of the cells on cover slips from different treatment groups permitted the analysis of the number of cells labeled by the fluorescent toxophore. No targeting ligand was present on the toxophore, and consequently, the level of HUVEC interaction was using a fluorescent microscope and comparing the number of cells labeled from at least ten independent fields, different coverslips or different slids. DAPI stain was used to localize cells, particularly in the case of the mutant constructs as cell labeling was not readily apparent. 4'-6-Diamidino-2-phenylindole (DAPI) is known to form fluorescent complexes with natural double-stranded DNA, as such DAPI is a useful tool in various cytochemical investigation. When DAPI binds to DNA, its fluorescence is strongly enhanced. Thus, DAPI serves as a method of labeling cell nuclei. In contrast, cells treated with F-150DT toxophore were easily observed. To facilitate that quantification of the mutant DT toxophore constructs the signal intensity and change in background signal were also increased.

Figure 5A:
FIGS. 5A and 5B show representative photomicrographs illustrating the levels of fluorescence between wild type DT toxophore mediated HUVEC staining (FIG. 5A) and VLS modified HUVEC staining (FIG. 5B).
Figure 5B:
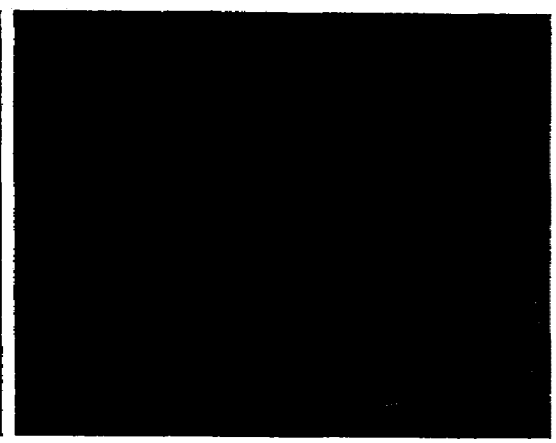
Figure 6:
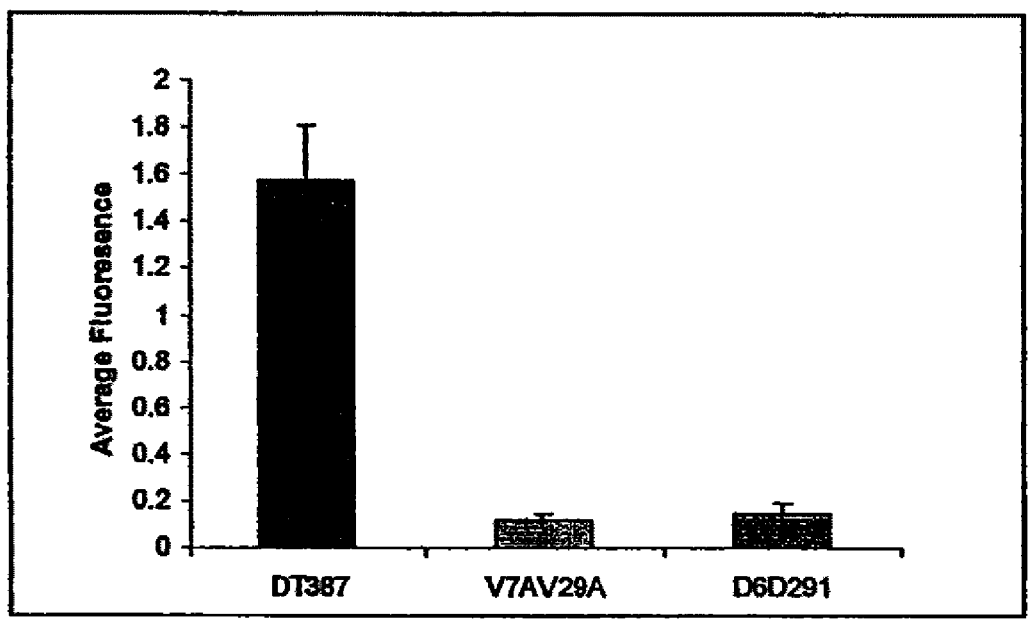
FIG. 6 illustrates HUVEC binding to DT387 and VLS modified DT387 toxophores.

FIGS. 5A and 5B show representative photomicrographs illustrating the levels of fluorescence between wild type DT toxophore mediated HUVEC staining and VLS modified HUVEC staining. There is a discernable difference in the number of cells labeled and the intensity of the labeled cells using the native DT toxophore molecule versus the VLS modified molecules. As shown in FIG. 6, this change in labeling accounts for the greater than ten fold decrease in average fluorescence observed when a VLS modified DT toxophore is employed to label HUVECs.

EXAMPLE 3

VLS Mutants Retain ADP-Ribosyltransferase Activity

Ribosome inactivating protein toxins such as diphtheria toxin catalyze the covalent modification elongation factor tu (EF-tu). Ribosylation of a modified histidine residue in EF-tu halts protein systhesis at the ribosome and results in cell death. Ribosyltransferase assays to determine catalytic activity of the DT387 mutants are performed in 50 mM Tris-Cl, pH8.0, 25 mM EDTA, 20 mM Dithiothreitol, 0.4 mg/ml purified elongation factor tu, and 1.0 pM [$^{32}$P]-NAD$^+$ (10 mCml, 1000 Ci·mmol, Amersham-Pharmacia). The purified mutant proteins are tested in a final reaction volume of 40 µl. The reactions are performed in 96 well, V-bottom microtiter plates (Linbro) and incubated at room temperature for an hour. Proteins are precipitated by addition of 200 µl 10% TCA and collected on glass fiber filters, and radioactivity dis etermined by standard protocols.

Figure 7:
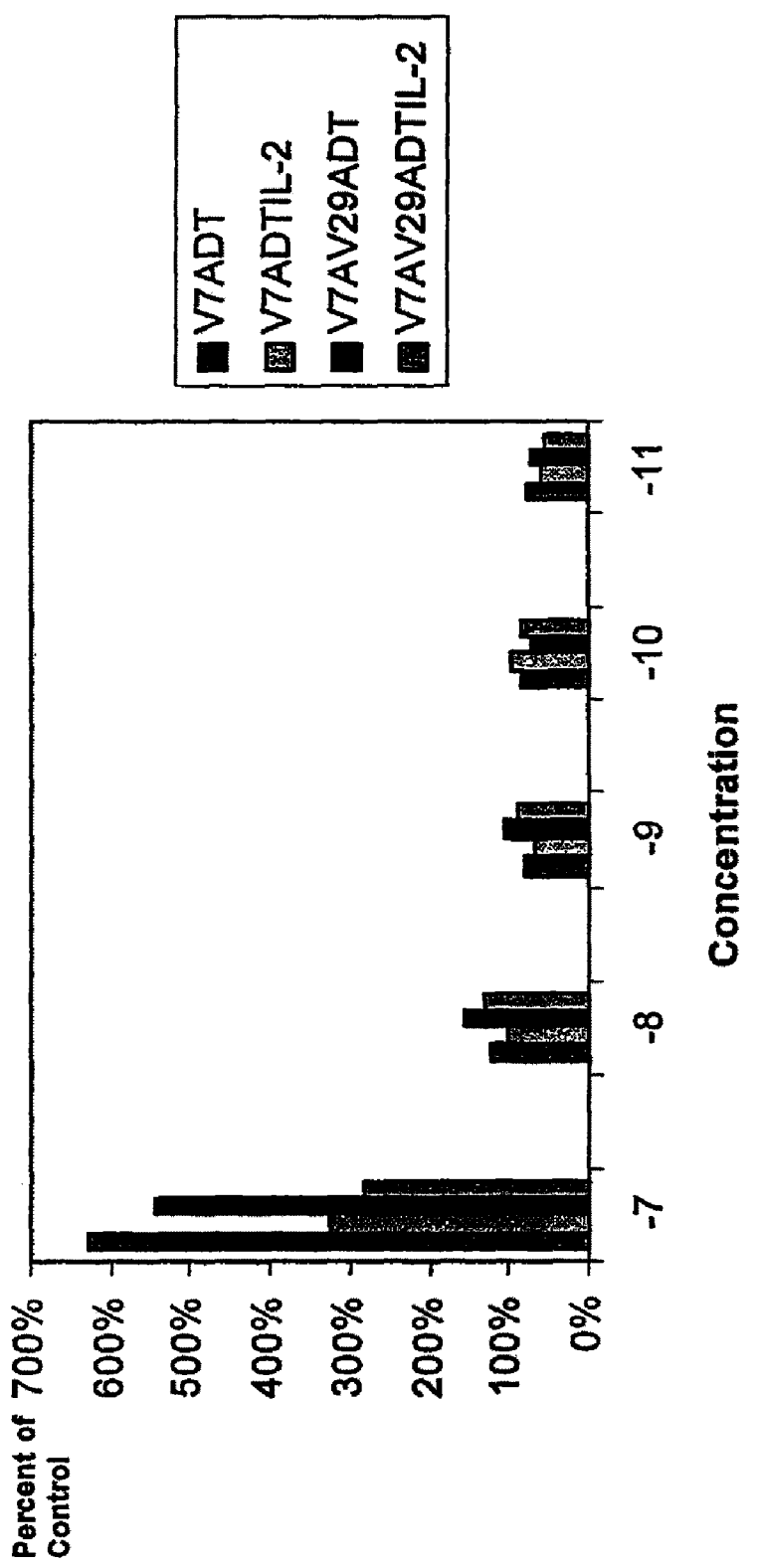
FIG. 7 is a diagram showing the ADP ribosyltransferase activity of certain DT mutants. ADP ribosyltransferase assay in which the activity of alanine substitute VLS modified DT toxphores or DT387IL2 fusion proteins were compared to fragment A of native DT.

As shown in FIG. 7, DT mutants DT387(V7A), DT387 (V7A)linkerIL-2, DT387(V7AV29A), and DT387 (V7AV29A)linkerIL-2 exhibited ADP ribosyltransferase activity that was equivalent or higher than that exhibited by fragment A of native DT.

EXAMPLE 4

VLS Mutants Suitable for DT-Fusion Proteins-VLS-Modified DTEGF

The ability to create, express and obtain selective receptor-specific fusion toxins using VLS modified DT-based toxophores is central to the disclosure. Proteins expressed from gene fusions between the modified toxophore and a specific targeting ligand allow the development of fusion toxins that can be used as research tools, as in vitro components of developing cell therapies and in vivo as therapeutics.

Cells integrate a variety of signals required for the maintenance of homeostasis and normal tissue function. These signals include soluble factors liberated by adjacent cells, regional tissue-specific factors and signals from remote sites with an organism. These signals can take the form of proteins, cytokines, hormones, peptides, enzymes, metabolites or small signaling molecules. The target cells express receptors specific to these signaling molecules and these receptors are critical for the appropriate reception and integration of these signals. Diseases such as cancer are often characterized by aberrant signaling and some signals have been shown to stimulate proliferation and differentiation of the malignant cells. The Epidermal Growth Factor, or EGF is a peptide cytokine that plays a variety of roles in the body including a role as a proliferation factor for cells bearing the EGF receptor or receptors capable of binding EGF. Inappropriate signaling through EGF receptors has been implicated in a number of tumors including breast cancer, squamous cell cancer of the head and neck, pancreatic cancer and glioblastoma. In the case of glioblastoma, patients often exhibit a rearrangement of the gene encoding the EGF receptor in tumor tissue. The rearrangement is typically associated with a dramatic over-expression of this growth factor receptor on the cancerous cells. This differential expression of EGF receptor on tumor cells makes it possible to direct an EGF diphtheria toxin protein fusion toxin to these cancerous cells and selectively ablate them from the patient. (Shaw, et al., *Jour. Biol. Chem.*, 266:21118-21124 (1991)) EGF signaling has also been implicated in the establishment of new blood vessel formation are process known as angiogenesis. Angiogenesis is important in the development of a number of tumors and thus, DTEGF fusion toxin could be employed to prevent angiogeneisis in solid tumors and reduce its size or prevent its development. Thus a VLS-modified DTEGF would have clinical utility and could be used to treat a number of diseases characterized by aberrant EGF receptor expression.

In addition there are circumstances in which normally appropriate EGF signaling is undesirable and the use of a DTEGF fusion toxin under these circumstance could be clinically useful. For example, as described by Pickering et al "smooth muscle cell proliferation in arteries is a common event after balloon angioplasty and bypass surgery and it is associated with vascular narrowing". DTEGF can be utilized to prevent smooth muscle cell proliferation and it can be locally applied to prevent vascular narrowing. (Pickering et al., *J Clin Invest* 91(2):724-9 (1993)).

To determine if the modified VLS DT-based toxophore described above could be employed to create viable, active fusion toxins, VLS-modified DT387linkerEGF fusion toxins were created and tested. Plasmids encoding VLS-modified toxophores were used as starting vectors and an in-frame insertion of the nucleotide sequence encoding EGF was inserted to create VLS-modified DTE387linkerEGF fusion proteins.

The fusion proteins were expressed essentially as described above. Induction of mutant DT387linker EGF fusion protein expression was obtained by addition of isopropylthiogalactosidase (ITPG) to *E. coli* HMS174 (DE3). *E. coli* HMS174 is a protease-deficient strain in which over-expression of recombinant proteins can be achieved. Following incubation, the bacterial cells were harvested by centrifugation, the DTEGF bacterial pellets were homogenized in 20 ml, ice cold, STET buffer (50 mM Tris-Cl, pH 8.0, 10 mM EDTA, 8% glucose, 5% Triton X-100). Lysozyme was added to 25 µg/ml and the bacteria were incubated on ice for 1 hour. The preparation was homogenized and then subjected to centrifugation at 6000×g for 30 minutes to 4° C. The resulting pellet was resuspended in 20 ml of STET and homogenized and the centrifugation step repeated. The final pellet was resuspended in 5 ml 7M GuHCl, 50 mM Tris-Cl, pH 8.0, homogenized and centrifuged, 6000×g, 30 minutes, 4° C. The supernatant was used in refolding assays.

The supernatant protein concentration was 5 mg/ml and refolding was performed at final concentrations of 0.4 mg/ml and 0.08 mg/ml. Refolding was assessed using a Pro-Matrix protein refolding kit from Pierce. (Pierce Biotechnology Inc., Rockford, Ill.) The refolding conditions are shown in Table 3.

TABLE 3

Folding conditions in Pierce Pro-Matric refolding kit used to determine optimal refolding conditions for VLS-modified DT387linker EGF fusion proteins produced in *E. coli*.

| Tubes | GuHCl (M) | L-Arginine (M) | GSG (mM) | GSSG (mM) |
| --- | --- | --- | --- | --- |
| 1 + 10 | 0 | 0 | 2 | 0.2 |
| 2 + 11 | 0 | 0.4 | 2 | 0.4 |
| 3 + 12 | 0 | 0.8 | 1 | 1 |
| 4 + 13 | 0.5 | 0 | 2 | 0.4 |
| 5 + 14 | 0.5 | 0.4 | 1 | 1 |
| 6 + 15 | 0.5 | 0.8 | 2 | 0.2 |
| 7 + 16 | 1.0 | 0 | 1 | 1 |
| 8 + 17 | 1.0 | 0.4 | 2 | 0.2 |
| 9 + 18 | 1.0 | 0.8 | 2 | 0.4 |

Figure 8:
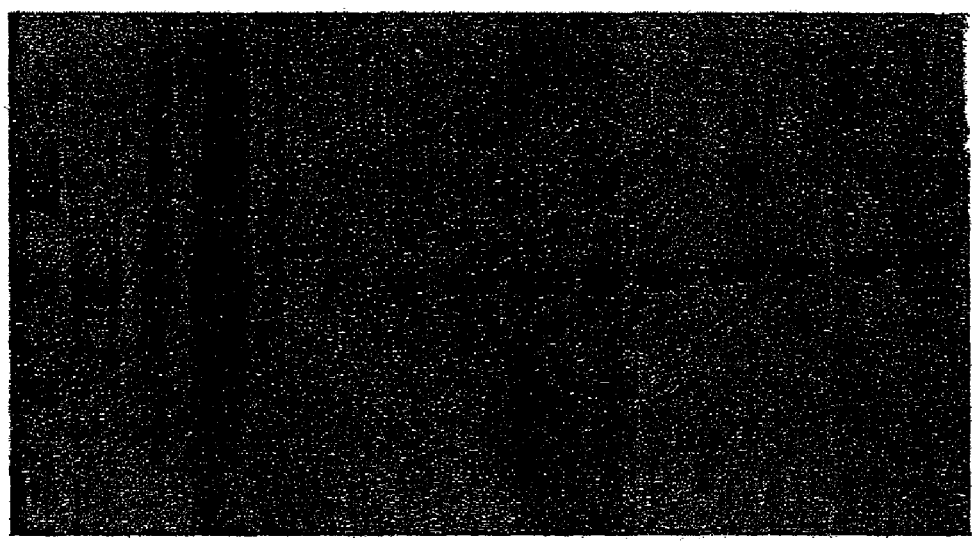
FIG. 8 depicts an example of Coomassie stained SDS-PAGE analysis of crude and purified refolded samples of DT387EGF fusion protein (DT387(D8EV29A)EGF). Tubes 1-9 not depicted.

Tubes 1-9 had a final concentration of $1.6 \times 10^{-6}$ M and tubes 10-18 had a final concentration of $8 \times 10^{-6}$ M DT387 (D8EV29A)linker EGF. The tubes were incubated overnight at 4° C. and 1 µl volumes were assayed the next day for cytotoxicity on U87MG glioblastoma cells (Glioblastoma cells have been shown to express EGF receptors ((Frankel et al., *Clin Cancer Res.*, 8(5): 1004-13 (2002)). The samples were also analyzed by gel electrophoresis to assure no degradation had occurred during refolding (FIG. 8).

Figure 9:
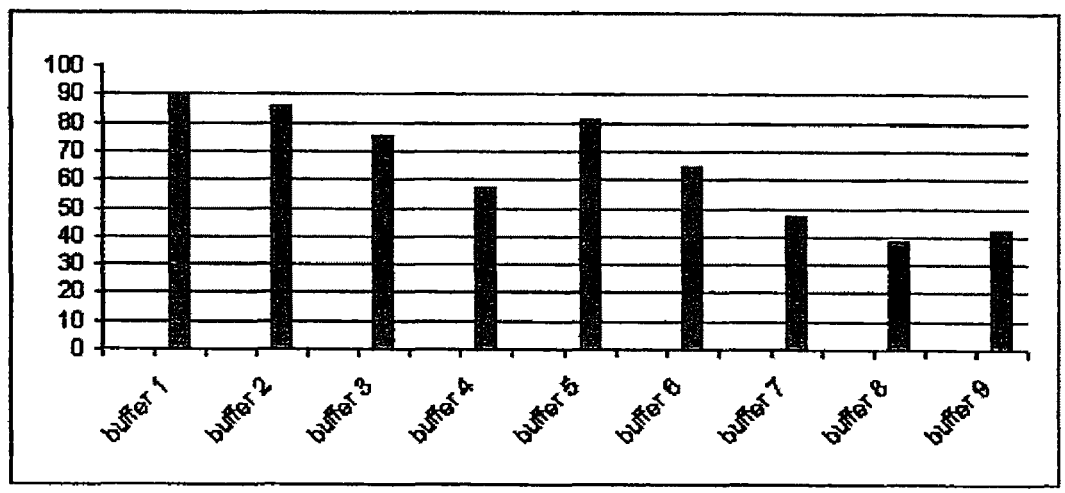
FIG. 9 is a diagram showing the cytotoxicity of $8 \times 10^{-9}$ M DT387(D8EV29A)linker EGF in EGF receptor positive U87MG glioblastoma cells under refolding buffer conditions 1-9.
Figure 10:
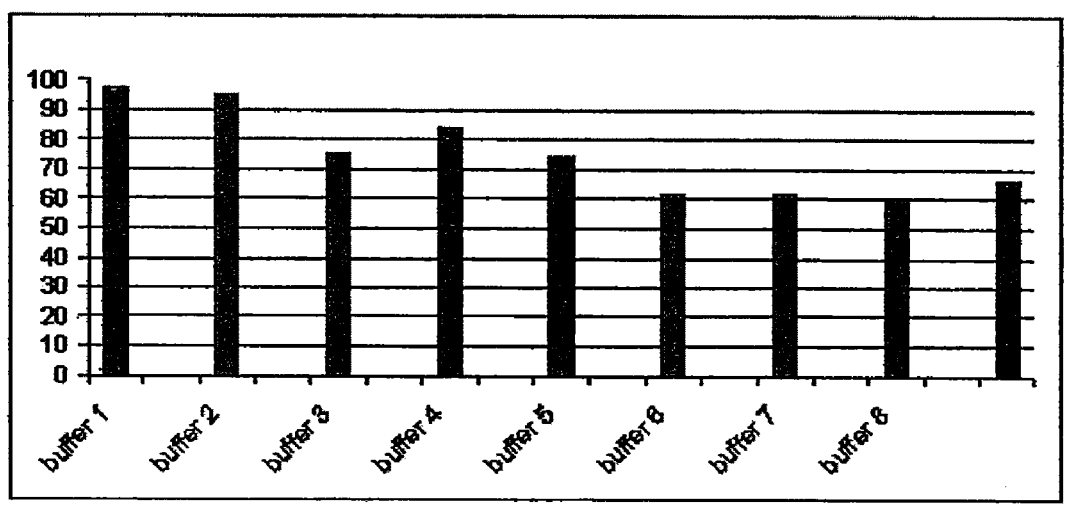
FIG. 10 is a diagram showing the cytotoxicity of $4 \times 10^{-8}$ M DT387(D8EV29A)linkerEGF in U87MG cells under refolding buffer conditions 10-18.

Samples of VLS-modified fusion toxins (shown here VLS-modified DT387(D8EV29S)linker EGF and DT387EGF were purified through the inclusion body step, denatured and subjected to refolding under a variety of conditions. Samples were then dialysed to remove any residual contaminants from the refolding conditions and tested for activity in cytotoxicity assays against U87MG EGF-receptor-bearing cells. These preparations are still considered crude and were used only to compare conditions which resulted in enhanced activity relative to standard refolding conditions and fusion toxins created using the native DT toxophore [in the context of an EGF fusion toxin DTEGF]. FIG. 9 shows the results for cytotoxicity assays of samples 1-9, using protein concentration of DT387(D8EV29A)linker EGF of $8 \times 10^{-9}$ M. FIG. 10 depicts the results for tubes 10-18 in which the protein concentration of DT387(D8EV29A)linker EGF employed were higher ($4 \times 10^{-8}$ M). Refolding to an actively cytotoxic form was more efficient when the lower concentrations of DT387 (D8EV29A)linker EGF fusion toxin were employed. Buffer conditions 4, 6 and 8 were chosen for further refinement.

New preparations of DT387EGF and DT387(D8EV29A) linker EGF were prepared as described above. The final, denatured supernatants were refolded in buffers 4, 6 or 8, (see Table 3), at lower protein concentrations. After refolding, the samples were dialyzed against corresponding refolding buffers, without GuHCl, permitting higher concentrations of fusion toxin to be tested. The results indicate that the $IC_{50S}$ for DT387EGF ranged from $8 \times 10^{-10}$ M to $1.5 \times 10^{-9}$ M for the buffers tested. Buffer 8 appeared to yield the most productive protein. The same holds true for refolding of the DT387 (D8EV29A)linker EGF mutant.

Figure 11:
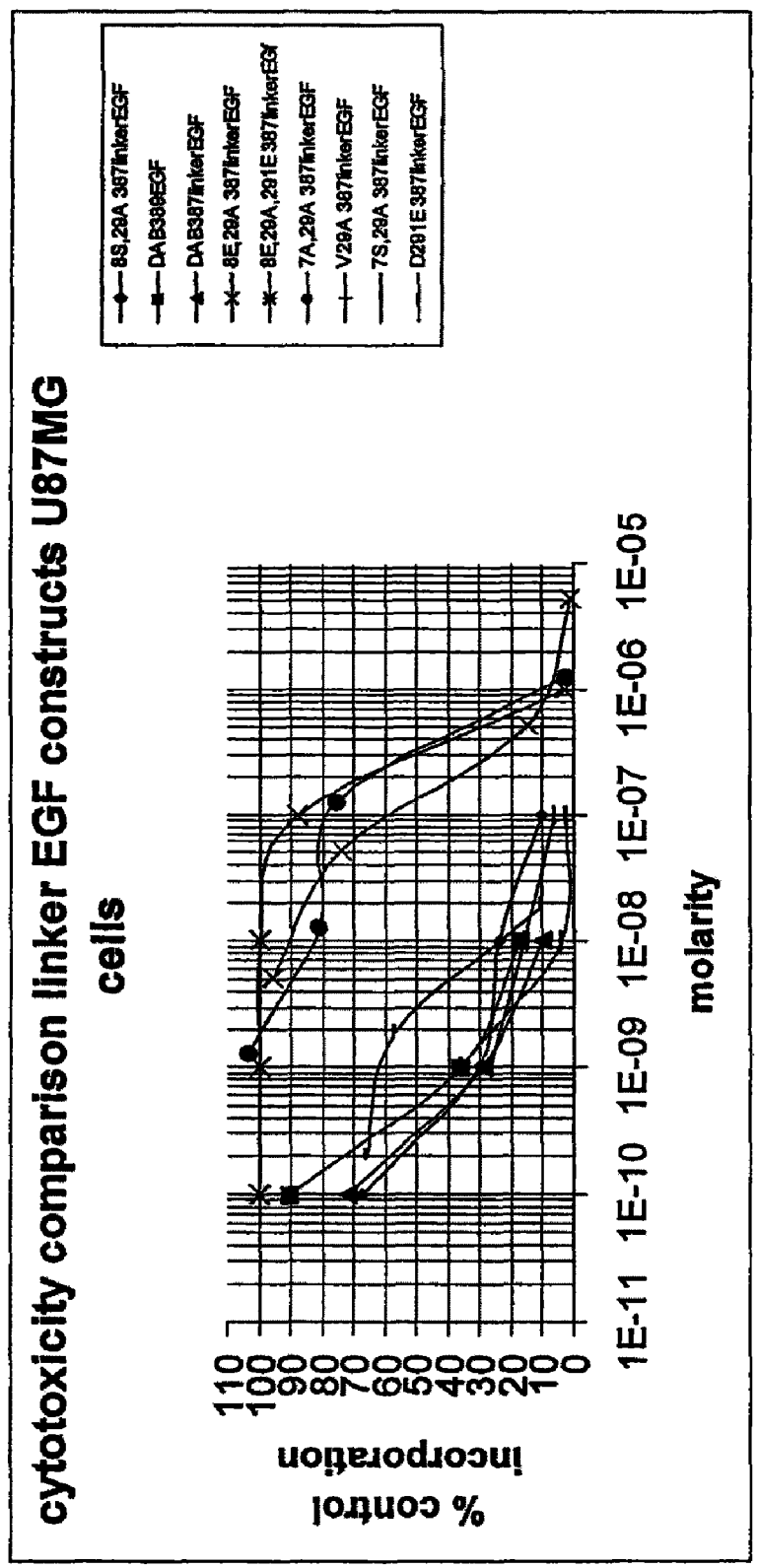
FIG. 11 is a diagram showing the cytotoxicity of DT389EGF and VLS modified DT387linkerEGF fusion proteins, DT387linkerEGF, DT387(D8E, V29A)linker EGF, DEF, DT387(D8S, V29A)linkerEGF, DT387(D8E, V29A, D291 E)linkerEGF, DT387(V7A, V29A)linkerEGF, DT387 (V29A)linkerEGF, DT387(V7S, V29A)linkerEGF, DT387 (D291E)linker IL2 in U87MG cell.

Other VLS-modified DT387EGF fusion proteins were also tested for their cytotoxicity in EGF-receptor-positive U87MG glioblastoma cells. As shown in FIG. 11, the EGF fusion toxins created with VLS modifications that exhibit the greatest selective toxicity against EGF-receptor-bearing cell are DT387(V7SV29A)linker EGF, DT387(D291E)linker EGF, DT387(V29A)linker EGF. These EGF fusion toxins display IC 50s comparable to cGMP prepared DT387linker EGF and DT 387linker EGF prepared under conditions identical to those used to express, refold and purify the VLS-modified DT387linker EGF fusion toxins. Thus, the VLS modified DT-based toxophores can be employed to create novel DT-based fusion toxins.

Figure 12:
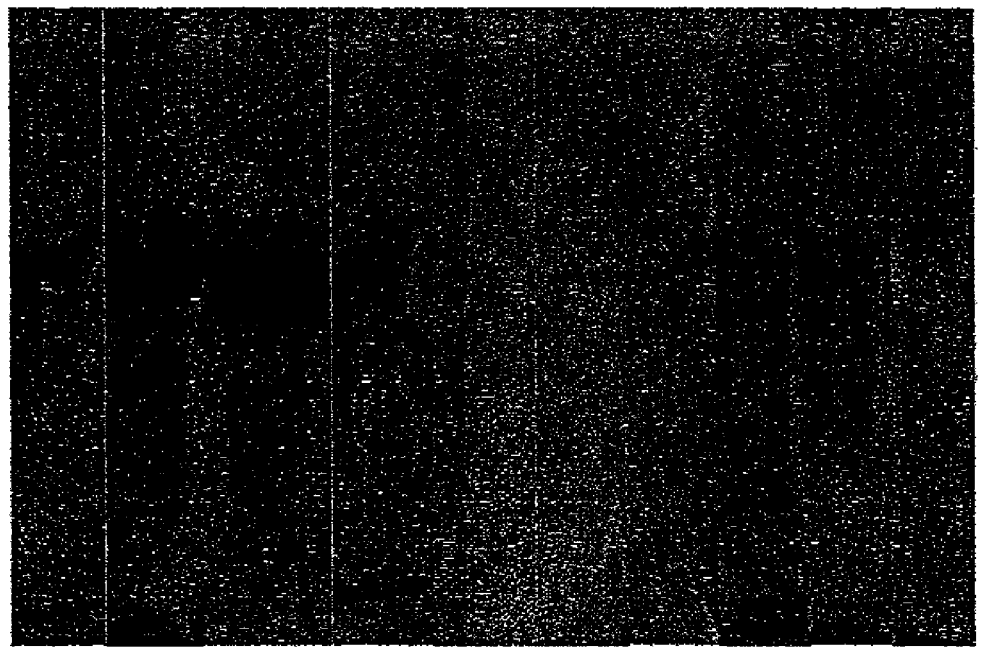
FIG. 12 is a Coomassie stained SDS-PAGE gel showing the level of purity for the VLS-modified DT387EGF fusion protein tested in FIG. 11.

FIG. 12 is a Coomassie stained SDS-PAGE gel showing the level of purity for the VLS-modified DT387linker EGF fusion protein tested in FIG. 11. Several additional species are apparent on the gel and the variation of expression levels can be observed. Resolution of these species by both anion exchange chromatography and sizing yielded fusion preparations that were homogenous and exhibited higher specific toxicity. This presumably was a function of the relatively purity of the active species versus the total protein concentration used to determine $IC_{50S}$.

EXAMPLE 5

VLS Mutants Suitable for DT-Fusion Protein-VLS Modified DTIL-2

1(a) Cytoxocity Assays on Crude Extracts of DT387Linker EL-2 VLS Mutants.

The DT387 construct was initially used to demonstrate that VLS-modified toxophores could be chemically coupled to a number of targeting ligands and yield functional targeted toxins. The large-scale production of targeted toxins following chemical conjugation, however, was not a commercially viable enterprise and the advent of single chain fusions toxins as exemplified by DT387linker IL-2 circumvents the scale-up purification problems typically encountered in the development of conjugate toxins. Fusion toxins, however, do present challenges in that the single chain molecules must be purified into an active, appropriately folded form capable of effective delivery of the catalytic domain of the toxin to targeted cells. Thus, the site-directed changes in VLS modified DT387 and DT387linker IL-2 might not yield functional molecules or molecules that can be readily refolded into active fusion toxins. To confirm the effects of the engineered changes, a number of VLS modified DT387IL-2 fusion toxins were produced and tested in cytotoxicity assays.

Conservative amino acid substitutions in the C and T domains of DT have been created. To determine that the changes do not yield inactive toxophores incapable of producing fusion toxins, cytotoxicity assays were performed. Readily apparent patterns have emerged which dictate the type of amino acid substitutions that can be accepted at each of the three VLS motifs within DT. Results indicate that mutations of the VLS sequences present at amino acid residues 7-9 or 290-292 of the DT toxophore resulted in less binding to human umbilical vein cell monolayers in culture. Some constructs demonstrated low levels of expression. Consequently additional VLS mutants were developed including: V7S, D8E, D8S and D291E.

The cytotoxicities of crude extracts of wild type $DAB_{389}IL-2$, two of the VLS mutants and a control were assayed as indicated. The results are reported as a percentage of control incorporation (no toxin added to cells).

Figure 13:
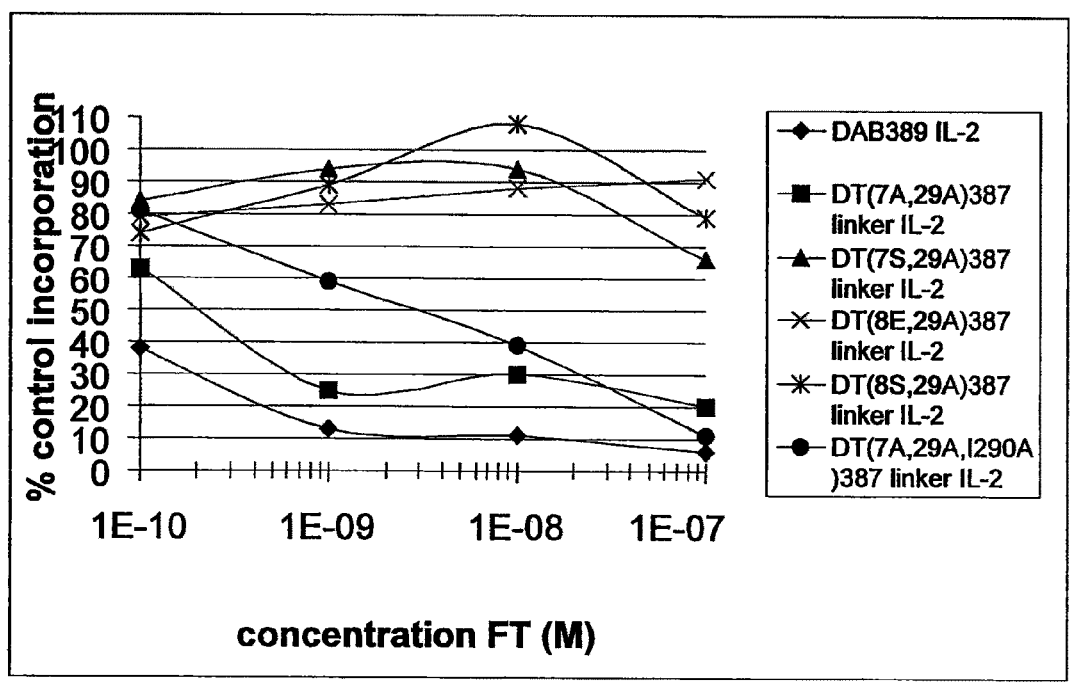
FIG. 13 is a diagram showing the cytotoxicity of DT387IL2, DT387(D8S, V29A)linkerIL2, DT387(V7A, V29A, D291 E)linkerIL2, DT387(V7A)linkerIL2, DT387 (V7S, V29A)linkerIL2, DT387(D8E, V29A)linkerIL2 in IL-2 receptor positive HUT102/6TG cells.

These mutants were incorporated alone or in combination (D8S, V29A and V7A, V29A, 1290A variants) into DT387linker IL-2 and have been tested as partially purified extracts in cytotoxicity assays and results indicate they are cytotoxic when compared to the negative control, DAB389linker EGF control, (which contains a targeting ligand to a receptor not expressed on HUT102/6TG cells) and DAB389linker IL-2. All VLS modified mutant toxophore fusion toxins were compared to DAB389linker IL-2 produced and tested at similar levels of purity and concentration. The triple mutant, DT387(V7A, V29A, D291E)linker IL-2 was expressed in full-length form, despite the valine to alanine change at position 7, and was also cytotoxic. FIG. 13 shows the representative results of a cytotoxicity assay using DT387linker IL-2, DT387(D8SV29A)linker IL-2, DT387, DT387(V7AV29A)linker IL2, DT387(V7AV29AI290A) linker IL2, DT387(V7SV29A)linker IL2, and DT387 (D8EV29A)linker IL2.

Cytotoxicity assays are performed using HUT102/6TG cells, a human HTLV1 transformed T-cell line that expresses high affinity Interleukin-2 receptors. HUT102/6TG cells are maintained in RPMI 1640 (Gibco) media supplemented with 10% fetal bovine serum, 2 mM glutamine, 50 IU/ml penicillin and 50 μg/ml streptomycin. The cells are seeded at a density of $5 \times 10^4$/well into 96 well, V-microtiter plates. The fusion protein toxins are typically added to the wells in molarities ranging from $10^{-7}$ M down to $10^{-12}$ M. Final volume in the wells is 200 μl. The plates are incubated for 18 hours, at 37° C. in a 5% $CO_2$ environment. The plates are subjected to centrifugation to pellet the cells, the media removed and replaced with 200 μl leucine-free, minimal essential medium containing 1.0 μCi/ml[$^{14}$C] leucine (<280 mCi/mmol, Amersham-Pharmacia) and 21 mM glutamine, 50 IU/ml penicillin and 50 μg/ml streptomycin. The cells are pulsed for 90 minutes and then the plates subjected to centrifugation to pellet the cells. The supernatant is removed and the cells are lysed in 60 μl, 0.4 M KOH followed by a 10 minute incubation at room temperature. 140 μl of 10% TCA is then added to each well and another 10 minute, room temperature incubation is performed. The precipitated proteins are collected on glass fiber filters using a "PHD cell harvester" and the incorporated radioactivity is determined using standard methods. The results are reported as a percentage of control (no fusion protein added to inhibit protein synthesis) [$^{14}$C]-leucine incorporation.

Figure 14:
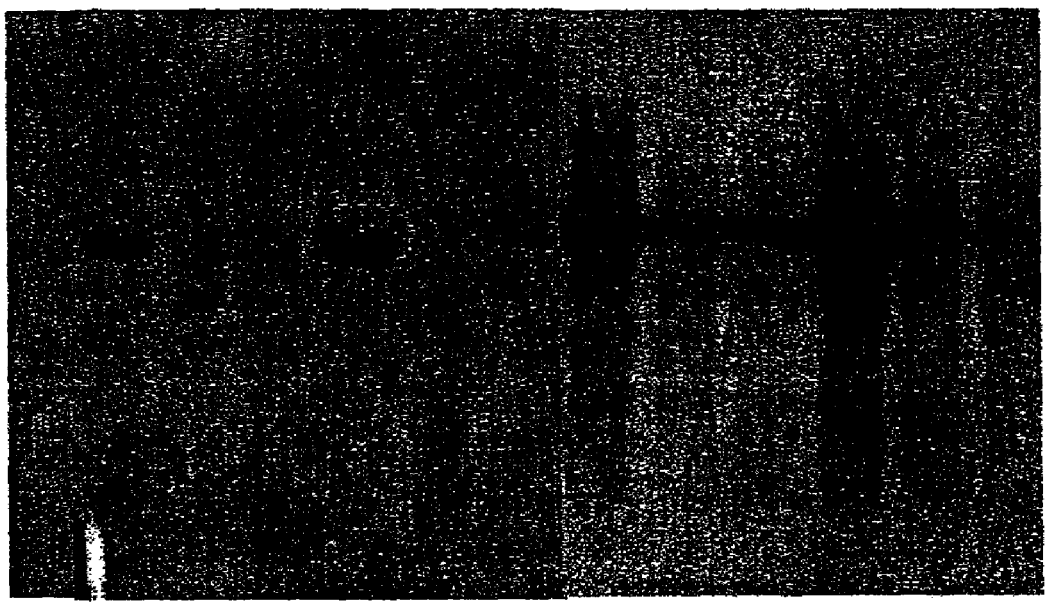
FIG. 14 and is a Coomassie stained SDS-PAGE gel and Western blot showing the level of purity for the VLS-modified DT387linkerIL2 fusion proteins tested in FIG. 13.

Pharmaceutical grade GMP purified $DAB_{389}IL$-2 produced from *E. Coli* typically yields an $IC_{50}$ of between $5\times10^{-11}$ M to $1\times10^{-12}$ M. Partially purified toxins exhibit activity between 10-100 fold lower in partially purified non-homogenous extracts. Pharmaceutical grade toxins are purified to homogeneity and the active fractions of refolded fusion toxins are used as biologically active drug. In the example above we utilize a moderate through put analysis to determine the receptor specific cytotoxicity of partially purified VLS modified DT-IL-2 fusion toxins and compared them to the activity of similarly purified $DAB_{389}IL$-2. These assays demonstrate comparable activity of the VLS modified DT387linker BL-2 fusion to $DAB_{389}IL$-2. It should be noted that the calculation of specific cytotoxicity was based upon the total amount of protein in the samples of partially fusion toxin. For assays equimolar concentrations of fusion toxins were tested. As shown below in panel FIG. 14 panels A and B each fusion toxins construct displayed patterns on 10% SDS PAGE and Western (anti diphtheria toxin) analysis. In FIG. 14, A is coomassie stained gel of partially purified inclusion body preparations. Lane 1, molecular weight markers; lane 2, $DAB_{389}IL$-2; lane 3, DT387(V7AV29A)linker IL-2, lane 4, DT387(V7S, V29A)linker IL-2, lane 5, DT387(D8E, V29A) linker EL-2; lane 6, DT387(D8S, V29A) linker IL-2; lane 7, DT387(V7A, V29A, D291E) linker IL-2. B is corresponding Western blot with horse anti-DT first antibody and rabbit anti-horse secondary antibody. The relative amounts of non-fusion toxins protein in each sample could artificially alter the $IC_{50}$ of any given construct. That is, the presence of non full length, or non fusion toxin protein in the samples used in this analysis could potentially account for small differences in $IC_{50}$.

The cytotoxicity data clearly demonstrate that the modifications that reduce HUVEC binding can be employed to create functional DTIL-2 fusion toxins.

Purified $DAB_{389}$ IL-2 produced in *E. coli* typically yields an $IC_{50}$ of between $5\times10^{-11}$ M to $1\times10^{-12}$ M. In the example above, a moderate through put cytotoxicity assay was used to analyze crude purifications of VLS modified DT-IL-2 fusion toxins and compared them to the activity of similarly purified DT387linkerIL-2. Insert figure for comparison of relative purity of IL2 fusion toxins in this assay.

It should be noted that there is one (x)D(y) motif in IL-2 located at residues 19-21 (LDL). The contribution of IL-2 to VLS can be determined by modifying the (x)D(y) motif in the IL-2 and test the modified protein using the cytotoxicity assay described above. [For example, using VLS-modified DT mutants derived from both DT387 and DT387linker IL-2, it is possible to distinguish between effects of the VLS mutations on catalytic activity, VLS activity and effective delivery of the targeted toxin to the cytosol of target cells]. The comparison between VLS-modified DT mutants of DT387 and DT387linker EL2 will also separate the effects of VLS sequences of the toxophore alone from the EL-2 targeting ligand present in DT387linkerIL-2.

Table 4 summarizes the $IC_{50S}$ of VLS-modified DT mutants. Mutants not tested are indicated by "n.t." Primary screening of mutants was performed following expression and crude primary inclusion body purification. Complete purification was not performed and the VLS modified toxophores have all been tested in the context of at least one fusion toxin (EGF receptor or IL-2 receptor targeted) and compared to DT387 based parental fusion toxin expressed and prepared to a similar level of purification.

TABLE 4

$IC_{50S}$ of VLS-modified DT mutants

| SINGLE MUTANT | DOUBLE MUTANT | TRIPLE MUTANT |
|---|---|---|
| DT387 (V7A) >$10^{-7}$ | DT387 (V7A, V29A) >$10^{-7}$ | DT387 (V7A, V29A, D291E) >$10^{-7}$ |
| DT387 (D8S) $2 \times 10^{-8}$ | DT387 (V7S, V29A) $2 \times 10^{-8}$ | |
| DT387 (ΔD8) >$10^{-7}$ | DT387 (D8S, V29A) $2.5 \times 10^{-10}$ | |
| DT387 (V29A) $2 \times 10^{-10}$ | DT387 (D8S, D291S) n.t | |
| | DT387 (D8E, V29A) $5 \times 10^{-9}$ | |
| | DT387 (V29A, D291E) $2 \times 10^{-9}$ | |

The $IC_{50S}$ were determined in the cytotoxicity assay as described in Examples 4 and 5, $IC_{50S}$ for DT387linker EGF and DT387linker IL-2 were found to be in a similar range from $5\times10^{-9}$ to $1\times10^{-10}$ M. The cytotoxicity of both the parental DAB 389-based fusion toxins and VLS-modified DT387 fusion toxins increased with increasing levels of purification. For example pharmaceutical grade DAB289EGF exhibits an $IC_{50}$ of $4.5\times10^{-11}$ M in these assays whereas crude inclusion body preparations of DT387(V29A)linker EGF exhibit an $IC_{50}$ of $2\times10^{-10}$ M.

Among the VLS-modified DT387 toxophore constructs tested thus far, DT387(V29A) and DT387(D8S, V29A) appear to maintain cytotoxicity comparable to wild type. The DT387(D8S) single mutant was not as cytotoxic as the corresponding double mutant indicating the additional change to V29A helped stabilize the molecule.

The preferred embodiments of the compounds and methods of the present invention are intended to be illustrative and not limiting. Modifications and variations can be made by persons skilled in the art in light of the above teachings specifically those that may pertain to alterations in the DT toxophore surrounding the described VLS sequences that could result in reduced HUVEC binding while maintaining near native functionally with respect to the ability to use as a DT toxophore in protein fusion toxin constructions. It is also conceivable to one skilled in the art that the present invention can be used for other purposes, including, for example, the delivery of other novel molecules to a selected cell population. It is envisioned that the present invention would be employed under those circumstances in which amounts of DT toxophore would be used to deliver such agents in a clinical setting or in settings where it would be desirable to reduce as much as possible the potential for VLS. In this setting the catalytic domain or some portion thereof would be replaced, or rendered inactive and fused with the desired agent or molecule. Acid sensitive or protease sensitive cleavage sites could be inserted between the remnant of the catalytic domain and the desired agent or molecule. Agents or molecules that might be coupled to VLS modified DT toxophore such as disclosed herein include but are not limited to; peptides or protein fragments, nucleic acids, ogligonucleotides, acid insensitive proteins, glycoproteins, proteins or novel chemical entities that required selective delivery. Therefore, it should be understood that changes may be made in the particular embodiments disclosed which are within the scope of what is described as defined by the appended claims.

What is claimed is:

1. An isolated polypeptide comprising amino acid residues 1-380 of SEQ ID NO:4, wherein the polypeptide comprises amino acid substitution at position V29 of SEQ ID NO:4, and, optionally with at least one amino acid substitution or deletion made within the regions selected from the group consisting of residues 7-9, 29-31 and 290-292, and wherein said DT variant has cytotoxicity comparable to that of a DT molecule having a sequence of SEQ ID NO:4.

2. The polypeptide of claim 1, wherein the polypeptide has reduced binding activity to human vascular endothelial cells (HUVECs) compared to a polypeptide comprising an amino acid sequence as recited in SEQ ID NO:4 without substitutions.

3. The polypeptide of claim 1, wherein the polypeptide comprises a substitution at amino acid residue V29 selected from V29A, V29D or V29I.

4. The polypeptide of claim 3, wherein the substitution is V7A, V7S, D8E, D8S, I290A, D291E, or D291S or any combination thereof.

5. The isolated polypeptide of claim 1, further comprising a protein selected from the group consisting of EGF, IL-1, IL-2, IL-3, IL-4, IL-5, IL-6, IL-7, IL-8, IL-9, IL-10, IL-11, IL-12, IL-13, IL-14, IL-15, INFa, INFy, GM-CSF, G-CSF, M-CSF, TNF, EGF, VEGF, Ephrin, BFGF, and TGF.

6. The isolated polypeptide of claim 5, selected from the group consisting of EGF, IL-1, IL-2, IL-3, and IL-7.

7. The isolated polypeptide of claim 3, wherein the substitutions are selected from the group consisting of V7AV29A and V7SV29A.

8. The isolated polypeptide of claim 3, wherein the substitutions are V7V29D291 or V7V29I290.

9. The isolated polypeptide of claim 3, wherein the substitutions are V7AV29AI290A or V7AV29AD291E.

10. A composition comprising the isolated polypeptide of claim 1 in a pharmaceutically acceptable carrier.

11. The isolated polypeptide of claim 1, further comprising a linker peptide moiety of SEQ ID NO:6.

12. The isolated polypeptide of claim 11, wherein the linker peptide moiety comprises non-charged amino acid residues.

13. The isolated polypeptide of claim 11, as set forth in SEQ ID NO:5.

14. The isolated polypeptide of claim 13, further comprising EGF on the C-terminus of the protein.

15. An isolated polypeptide comprising amino acid residues 1-380 of SEQ ID NO:4, wherein the polypeptide comprises a substitution at amino acid residue V29 of SEQ ID NO:4 selected from V29A, V29D or V29I, and, optionally with at least one amino acid substitution or deletion made within the regions selected from the group consisting of residues 7-9, 29-31 and 290-292, and wherein said DT variant has cytotoxicity comparable to that of a DT molecule having a sequence of SEQ ID NO:4.

* * * * *